(12) United States Patent
Cogan et al.

(10) Patent No.: US 8,859,814 B2
(45) Date of Patent: Oct. 14, 2014

(54) ALPHA-SUBSTITUTED N-SULFONYL GYLCINE AMIDES ANTAGONISTS OF CCR10, COMPOSITIONS CONTAINING THE SAME AND METHODS FOR USING THEM

(75) Inventors: Derek Cogan, Sandy Hook, CT (US); Alexander Heim-Riether, Newtown, CT (US); Wang Mao, Milford, CT (US); Craig Andrew Miller, Norwalk, CT (US); Philip Dean Ramsden, Woodbury, CT (US); Lana Louise Smith Keenan, Poughquag, NY (US); Roger John Snow, Danbury, CT (US); Jiang-Ping Wu, Danbury, CT (US); Yu Yang, Clark, NJ (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 685 days.

(21) Appl. No.: 12/992,766

(22) PCT Filed: May 14, 2009

(86) PCT No.: PCT/US2009/043907
§ 371 (c)(1),
(2), (4) Date: Mar. 29, 2011

(87) PCT Pub. No.: WO2009/142984
PCT Pub. Date: Nov. 26, 2009

(65) Prior Publication Data
US 2011/0275612 A1  Nov. 10, 2011

Related U.S. Application Data

(60) Provisional application No. 61/055,213, filed on May 22, 2008.

(51) Int. Cl.

| | | |
|---|---|---|
| *C07C 303/00* | (2006.01) | |
| *C07C 307/00* | (2006.01) | |
| *C07C 309/00* | (2006.01) | |
| *C07C 311/00* | (2006.01) | |
| *C07C 241/00* | (2006.01) | |
| *C07C 241/02* | (2006.01) | |
| *C07D 211/00* | (2006.01) | |
| *C07D 211/68* | (2006.01) | |
| *C07D 211/80* | (2006.01) | |
| *C07D 213/02* | (2006.01) | |
| *C07D 217/00* | (2006.01) | |
| *C07D 209/04* | (2006.01) | |
| *C07D 231/00* | (2006.01) | |
| *C07D 277/60* | (2006.01) | |

(Continued)

(52) U.S. Cl.
CPC ............ *C07C 311/19* (2013.01); *C07D 211/22* (2013.01); *C07D 403/12* (2013.01); *C07D 217/06* (2013.01); *C07D 295/185* (2013.01); *C07D 513/04* (2013.01); *C07D 487/04* (2013.01); *C07D 211/70* (2013.01); *C07D 401/14* (2013.01); *C07D 209/08* (2013.01); *C07D 211/62* (2013.01); *C07D 211/16* (2013.01); *C07D 409/12* (2013.01); *C07D 413/12* (2013.01); *C07C 311/44* (2013.01); *C07D 407/12* (2013.01); *C07D 401/12* (2013.01)
USPC ............... 564/90; 564/80; 544/336; 546/139; 546/189; 546/193; 548/152; 548/356.1; 548/469

(58) Field of Classification Search
USPC ............... 564/80, 90; 544/336; 546/139, 189, 546/193; 548/152, 356.1, 469
See application file for complete search history.

(56) References Cited

U.S. PATENT DOCUMENTS

| | | | | |
|---|---|---|---|---|
| 5,663,174 | A | * | 9/1997 | Dumont .................... 514/253.05 |
| 6,680,329 | B2 | * | 1/2004 | Altenburger et al. ......... 514/318 |
| 2011/0124578 | A1 | * | 5/2011 | Eissenstat et al. ............ 514/21.1 |

FOREIGN PATENT DOCUMENTS

| | | | |
|---|---|---|---|
| WO | WO 9746553 | A1 * | 12/1997 |
| WO | 2008008374 | A2 | 1/2008 |

(Continued)

OTHER PUBLICATIONS

Cho et al. "Asymmetric Synthesis of Unnatural L-Amino Acids Using Thermophilic Aromatic L-Amino Acid Transaminase" Biothechnology and Bioprocess Engineering, 2006, vol. 11, pp. 299-305.*

(Continued)

*Primary Examiner* — Kendra D Carter
(74) *Attorney, Agent, or Firm* — Michael P. Morris; Edward S. Lazer

(57) ABSTRACT

Disclosed is a compound of formula (I). Wherein $R_1$, $R_2$Ar and Cy are as defined herein, or a pharmaceutically acceptable salt thereof. Also disclosed are pharmaceutical compositions of the compound of formula (I), methods of making the compounds of formula I, and methods of using the compounds of formula (I) to treat a disorder associated with activation of CCR10.

(I)

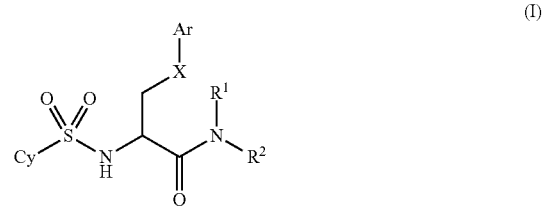

4 Claims, No Drawings

| (51) | Int. Cl. | |
|---|---|---|
| | C07D 277/62 | (2006.01) |
| | C07D 211/22 | (2006.01) |
| | C07D 403/12 | (2006.01) |
| | C07D 217/06 | (2006.01) |
| | C07D 295/185 | (2006.01) |
| | C07D 513/04 | (2006.01) |
| | C07D 487/04 | (2006.01) |
| | C07D 211/70 | (2006.01) |
| | C07D 401/14 | (2006.01) |
| | C07D 209/08 | (2006.01) |
| | C07D 211/62 | (2006.01) |
| | C07C 311/19 | (2006.01) |
| | C07D 211/16 | (2006.01) |
| | C07D 409/12 | (2006.01) |
| | C07D 413/12 | (2006.01) |
| | C07C 311/44 | (2006.01) |
| | C07D 407/12 | (2006.01) |
| | C07D 401/12 | (2006.01) |

(56) References Cited

FOREIGN PATENT DOCUMENTS

WO    2009052078 A1    4/2009
WO    2009142984 A1    11/2009

OTHER PUBLICATIONS

International Search Report for corresponding PCT Application PCT/US2009/043907 mailed on Sep. 9, 2009.

G. Wagner, et al.: "Synthese von 4-(4-Amidino-phenyl)-2arylsulfonylaminobuttersäureamid en" Die Pharmazie, vol. 37, No. 1, Jan. 1982, pp. 13-16, XP002540948 Govi Verlag, Eschborn, DE ISSN: 0031-7144.

H. Vieweg, et al.: "Synthese von alfa-(4- Amidinophenyl)-2-arylsulfonylaminobuttersäure-amielen" Die Pharmazie, vol. 38, No. 1, Jan. 1983, pp. 22-24, XP002540947 Govt Verlag, Eschborn, DE ISSN: 0031-7144.

\* cited by examiner

ALPHA-SUBSTITUTED N-SULFONYL GYLCINE AMIDES ANTAGONISTS OF CCR10, COMPOSITIONS CONTAINING THE SAME AND METHODS FOR USING THEM

BACKGROUND OF THE INVENTION

1. Field of the Invention

This invention relates to substituted amides that are useful as inhibitors of CCR10 activity and are thus useful for treating a variety of diseases and disorders that are mediated or sustained through the activity of CCR10 including inflammatory skin diseases, allergic asthma and melanoma. This invention also relates to pharmaceutical compositions comprising these compounds, methods of using these compounds in the treatment of various diseases and disorders, processes for preparing these compounds and intermediates useful in these processes.

2. Brief Description of the Art

Chemokine receptors play an important role in mediating tissue specific recruitment of leukocytes to sites of inflammation. Within the blood there is a subset of memory T cells that preferentially homes to the skin. This subset is defined by expression of the cutaneous lymphocyte antigen (CLA), a lectin, which binds to E-selectin on dermal endothelial cells and promotes trafficking. Although the subset of CLA-expressing cells constitutes only 10-15% of the circulating T cell pool, these cells are found in abundance within several inflammatory skin lesions, for example, psoriasis, contact sensitivity and allergic dermatitis.

Recent studies have revealed that CLA+ memory cells also express the chemokine receptor CCR10 and that cells expressing CCR10 are enriched in inflammatory skin lesions. One ligand for this receptor, CCL27, is also markedly upregulated at these sites suggesting that this chemokine receptor may participate in mediating the tissue-specific trafficking of CLA+ memory T cells. Within the skin, expression of CCR10 has been reported on CLA+ T cells, melanocytes, fibroblasts, and microvascular endothelial cells. CCL27 expression has been shown to be tightly regulated with abundant expression in the epidermis, predominantly by keratinocytes.

There is evidence in both humans and in rodents that the CCR10-CCL27 interaction plays an important role in the trafficking of inflammatory T cell subsets to skin lesions (J. Morales et al., Proc Natl Acad Sci USA, 1999, 96: 14470-14475; B. Homey et al., J Immunol 2000; 164: 3465-3470; B. Homey et al., Nature Medicine, 2002; 8: 157-165). By histological analysis, it is clear that, in addition to the increase in epidermal expression of CCL27 observed in psoriatic and atopic dermatitis biopsies, there is also expanded expression of CCL27 into the dermal layer as well. Further, endothelial cells within the vasculature of these lesions also display CCL27, though they are negative for CCL27 message, suggesting that keratinocyte derived CCL27 can be captured by endothelial cells and presented to circulating leukocytes. Accompanying these changes in the skin is a marked increase in the recruitment of lymphocytes that co-express CLA and CCR10. Consistent with the role of CCL27 in skin inflammation, IL-1 beta and TNF alpha treatment of cultured keratinocytes induces expression of CCL27.

Cutaneous application of nickel, in nickel-allergic humans, led to the up-regulated expression of CCL27 and the subsequent recruitment of CCR10+ lymphocytes. Thus, these stud ies provide temporal support for the role of CCL27 in attracting CCR10+ cells. Furthermore, in vivo proof of concept has been shown (B. Homey et al., ibid, 2002) in wild-type mice where treatment with a function blocking antibody against CCL27 clearly diminished recruitment and swelling in both DNFB-induced and ovalbumin DTH models of dermatitis. These authors also demonstrated the ability of cutaneous injection of CCL27 to promote local lymphocyte trafficking and inflammation, thus providing proof of concept using both ligand and antibody in relevant animal models. Consistent with its ascribed in vivo role, CCL27 induces calcium flux in CCR10+ cells and mediates the selective chemotaxis of CLA+ CCR10+ lymphocytes in vitro.

Studies, such as those described above, suggest that antagonism of the interaction between CCR10 and its skin derived ligand CCL27 could therefore be of benefit in the treatment of inflammatory skin diseases by blocking the entry and activation of T cells within the skin. One indication for a CCR10 antagonist would be psoriasis. The rationale is based on histological studies of receptor/ligand expression in humans with psoriasis and proof of concept studies in animal models of skin inflammation. From analysis of normal and diseased skin samples, it is clear that the expression of CCR10 is highly regulated and restricted primarily to a subset of skin homing (CLA+) lymphocytes, dermal endothelial cells, and dermal fibroblasts. In addition, CCL27, a ligand for CCR10, is also expressed in keratinocytes. In normal skin, CCL27 is expressed by keratinocytes in the basal layers of the epidermis. However, in the skin of atopic dermatitis and psoriasis patients this ligand is upregulated with expression extending to the suprabasal layers of the epidermis and histological staining also evident on the dermal microvasculature. The enhanced expression of CCL27 is accompanied by an increased presence of CCR10+ lymphocytes. Finally the proof of concept studies described above demonstrated that a function blocking antibody directed against CCL27 blocked trafficking of lymphocytes and swelling in two murine models of dermatitis.

Based on the pattern of expression for both CCR10 and CCL27 and the above proof of concept studies, CCR10 may also be a promising target for treatment of contact sensitivity and allergic dermatitis. It has been shown recently that CCL27 is increased in the sera of patients with systemic sclerosis (Hayakawa et al., Rheumatol, 2005, 44: 873) and in the dermis of UV-induced cutaneous SLE (systemic lupus erythematosus) lesions (Meller et al. 2005, Arthritis Rheum 52: 1504). Therefore, systemic sclerosis and cutaneous SLE could also be additional indications. In addition, inflammation of the respiratory tract in a murine model of allergic asthma is associated with CCL28 and CCR10 expression suggesting that inhibition of CCR10 activity may also be useful in treatment of allergic asthma (English et al., Immunol Lett. 2006, 03(2):92-100).

Antagonism of CCR10 may also be beneficial for the treatment of melanoma. In a mouse model of melanoma metastasis, it has been demonstrated that melanoma lines expressing CCR10 form tumors more readily than matched CCR10 deficient melanomas and that a blocking antibody against CCL27 can block the growth of these CCR10+ melanoma cells in vivo. These observations, coupled with the finding that many human melanomas express CCR10, provide the rationale for considering this as a further indication (Murakami et al., J Exp Med, 2003, 198: 1337).

BRIEF SUMMARY OF THE INVENTION

In a general aspect, the present invention is directed to the compounds of the formula I:

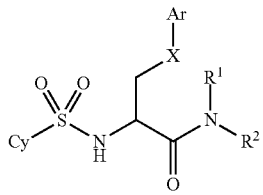

I wherein Ar, Cy, $R^1$, $R^2$, and X are as defined herein, as well as the tautomers thereof, and salts thereof. It has been found that the compounds of formula I have valuable pharmacological properties, particularly an inhibiting activity of CCR10 activity.

In another aspect, the present invention is directed to a method of inhibiting CCR10 activity in an individual comprising administering to the individual a therapeutically effective amount of a compound of formula I, or a pharmaceutically acceptable salt thereof.

In another aspect, the present invention is directed to a method of treating a disease or disorder associated with the activation of CCR10 comprising administering to an individual a therapeutically effective amount of a compound of formula I, or a pharmaceutically acceptable salt thereof.

In another aspect, the present invention is directed to a method of treating an inflammatory skin disease comprising administering to an individual a therapeutically effective amount of a compound of formula I, or a pharmaceutically acceptable salt thereof. Examples of such diseases that may be treated include, for example, psoriasis, contact sensitivity, allergic dermatitis, systemic sclerosis, and cutaneous SLE.

In another aspect, the present invention is directed to a method of treating allergic asthma comprising administering to an individual a therapeutically effective amount of a compound of formula I, or a pharmaceutically acceptable salt thereof.

In another aspect, the present invention is directed to a method of treating melanoma comprising administering to an individual in need of such treatment a therapeutically effective amount of a compound of formula I, or a pharmaceutically acceptable salt thereof.

In yet additional aspect of the present invention is a pharmaceutical composition comprising a compound of formula I, or a pharmaceutically acceptable salt thereof, and a pharmaceutically acceptable carrier.

The present invention also includes the processes for preparing the compounds of formula (I) and intermediates used therein.

DETAILED DESCRIPTION OF THE INVENTION

An embodiment of the present invention is a compound of formula I:

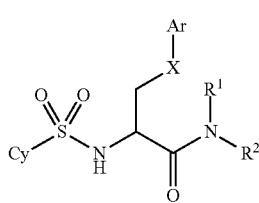

I wherein:

Cy is phenyl, naphthyl or heteroaryl, wherein heteroaryl is selected from indolyl, pyridyl, thienyl, pyrazolyl, oxazolyl, indazolyl, benzimidazolyl, isoquinolinyl, 1H-pyrrolo[2,3-b]pyridinyl, benzothienyl, benzofuranyl, 2,1,3-benzothiadiazolyl and 6H-imidazo[2,1-b]thiazolyl, wherein said phenyl naphthyl or heteroaryl is optionally substituted with one to four groups selected from $C_{1-6}$alkyl, $C_{1-6}$alkoxy, phenyl, heteroaryl, phenyloxy, halogen, —$NH_2$, —NHC(O)$NH_2$, —NHC(O)$C_{1-6}$alkyl, —$NO_2$, —$CF_3$, —$OCF_3$, —CN, —C(O)$C_{1-6}$alkyl, —$(CH_2)_{0-2}CO_2C_{1-6}$alkyl, —$(CH_2)_{0-2}$$CO_2H$, 5-tetrazolyl, —CHO, —C(O)$NH_2$, —C(O)NH($C_{1-6}$alkyl) and —C(O)N($C_{1-6}$alkyl)$_2$; or if Cy is phenyl, two adjacent groups together with the phenyl they are bonded to may form a 2,3-dihydrobenzofuranyl, 1,3-dihydroindol-2-one, or 2-acetyl-3,4-dihydro-1H-isoquinolinyl group;

Ar is a phenyl, pyridyl or isoquinolinyl group and is optionally substituted with one to two groups independently selected from halogen, —CN, —$NO_2$, $C_{1-6}$alkyl, —$CF_3$, $CO_2Me$, $CO_2H$, $CO_2NH_2$, —$SO_2C_{1-6}$alkyl, $SO_2NH_2$, and alkynyl;

$R^1$ and $R^2$ are independently selected from $C_{1-6}$alkyl, aryl$C_{1-2}$alkyl, phenyl, naphthyl and $C_{3-8}$cycloalkyl, wherein said aryl$C_{1-2}$alkyl is optionally substituted with one to two groups selected from halogen, $C_{1-6}$alkoxy, $C_{1-6}$alkyl, —$CF_3$, imidazolyl, pyridyl, pyrimidinyl, pyrazolyl, 5-methyloxadiazolyl, morpholinyl, piperidinyl and N-methyl-1,2,3,4-tetrahydroisoquinolinyl; or $R^1$ and $R^2$, together with the N they are bonded to form a heterocycle selected from piperidine, morpholine, tetrahydroisoquinoline, decahydroisoquinoline, piperazine, azepane, 6-aza-spiro[2.5]octane, 2,3,4,5-tetrahydro-1H-benzo[b]azepine, [1,4]-diazepane, [1,4]-oxazepane, thiomorpholine 1,1-dioxide, 4,5,6,7-tetrahydrothieno[3,2-c]pyridine, 5,6,7,8-tetrahydro-[1,2,4]triazolo[4,3-a]pyrazine, 5,6,7,8-tetrahydro-imidazo[1,5-a]pyrazine, 4,5,6,7-tetrahydrothiazolo[5,4-c]pyridine, 1,2,3,6-tetrahydropyridine and octahydropyrido[1,2-a]pyrazine, wherein said heterocycle is optionally substituted by one to two groups selected from $C_{1-6}$alkyl, $C_{1-6}$alkenyl, phenyl, benzyl, hydroxy$C_{1-6}$alkyl, —OH, —$CF_3$, —CN, halogen, —$NO_2$, —$NH_2$, oxo, 1,3-dioxolane, —CH=NOCH$_3$, —$SO_2NH_2$, —$SO_2N(C_{1-6}$alkyl)$_2$, —$SO_3H$, —$SO_2(C_{1-6}$alkyl)$_2$, —C(O)N($C_{1-6}$alkyl)$_2$, —C(O)NH$C_{1-6}$alkyl, —$(CH_2)_{0-2}$C(O)$NH_2$, —$(CH2)_{0-4}$$CO_2H$, —$(CH_2)_{0-4}CO_2C_{1-6}$alkyl, =C—$CO_2$C1-6alkyl, —CH=CH—$CO_2H$, —CH=CH—$CO_2C_{1-6}$alkyl, —OCH$_2$$CO_2H$, —OCH$_2$$CO_2C_{1-6}$alkyl, —OC(CH$_3$)$_2$$CO_2H$, —OC(CH$_3$)$_2$$CO_2C_{1-6}$alkyl, —C(O)CH$_2$$CO_2H$, —C(O)CH$_2$$CO_2C_{1-6}$alkyl, —C(O)$C_{1-6}$alkyl, —C(O)$C_{1-4}$alkyl(OH), —CH$_2$OC$_{1-6}$alkyl, —(CH$_2$)$_{0-2}$NHC(O)$C_{1-6}$alkyl, —C(O)morpholinyl, thiazole, 3-methyl-1,2,4-oxadiazolyl, pyrimidine and 2-[1,2,4]oxadiazol-3-ylpyrazine, and X is CH$_2$, O, NH, or S;

or a pharmaceutically acceptable salt thereof,

In another embodiment, there are provided compounds of formula I as described wherein:

Cy is a phenyl or heteroaryl selected from indolyl, 1,3-dihydro-indol-2-onyl, pyridyl, pyrazolyl, or benzothienyl, wherein said phenyl or heteroaryl is optionally substituted with one to four groups selected from halogen, methyl, amino, cyano, methoxy, trifluoromethyl, and —NHC(O)$C_{1-4}$alkyl;

Ar is a phenyl, pyridyl, or isoquinolinyl group optionally substituted by one to two groups independently selected from —Cl, —Br, —F, —CN, —$NO_2$, —$CO_2Me$, -Me, $SO_2Me$, ethynyl, and 1-propynyl;

$R^1$ and $R^2$, together with the N they are bonded to, form a heterocycle selected from piperidine, piperazine, azepane, [1,4]-diazepane, [1,4]-oxazepane, and 5,6,7,8-tetrahydro-[1,2,4]triazolo[4,3-a]pyrazine, wherein said heterocycle is optionally substituted by one to two groups selected from $C_{1-6}$alkyl, $C_{1-4}$alkylOH, C(O)$C_{1-4}$alkyl, $CO_2Me$, and oxo; and X is CH$_2$, O, NH, or S;

or a pharmaceutically acceptable salt thereof.

In still another embodiment, there are provided compounds of formula I, wherein:

Cy is a phenyl or indolyl and is optionally substituted by one to three groups independently selected from chloro and amino;

Ar is a phenyl group and is optionally substituted by one to two groups independently selected from —Cl, —Br, —F, —CN, -Me, —NO$_2$, ethynyl, 1-propynyl, and —CO$_2$Me;

R$^1$ and R$^2$, together with the N they are bonded to, form a heterocycle selected from piperidine, piperazine, azepane, and [1,4]-oxazepane, wherein said heterocycle is optionally substituted by C$_{1-6}$alkyl, (CH$_2$)$_{1-2}$OH, and C(O)C$_{1-4}$alkyl; and X is CH$_2$;

or a pharmaceutically acceptable salt thereof.

In still a further embodiment of the invention, there are provided compounds of the formula (I) selected from the group below or a tautomer thereof or a salt thereof:

| No. | Structure | Name |
|---|---|---|
| 1 | 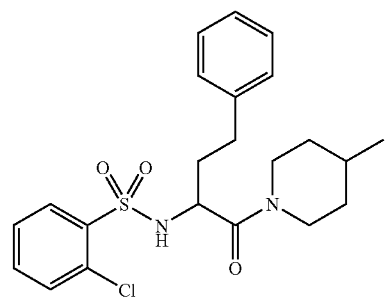 [SMILES: CC1CCN(C(=O)C(CCc2ccccc2)NS(=O)(=O)c2ccccc2Cl)CC1] | 2-chloro-N-{1-[(4-methylpiperidin-1-yl)carbonyl]-3-phenylpropyl}benzenesulfonamide |
| 2 | 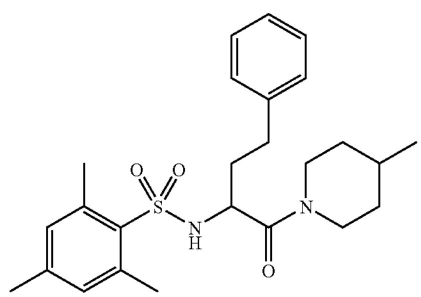 | 2,4,6-trimethyl-N-1-[(4-methylpiperidin-1-yl)carbonyl]-3-phenylpropyl}benzenesulfonamide |
| 3 | 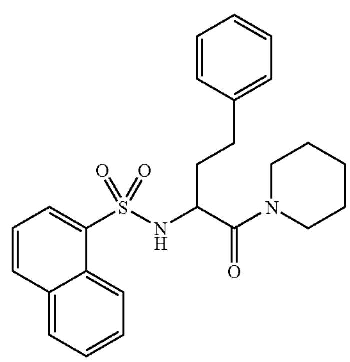 [SMILES: O=C(C(CCc1ccccc1)NS(=O)(=O)c1cccc2ccccc12)N1CCCCC1] | N-{1-[(4-methylpiperidin-1-yl)carbonyl]-3-phenylpropyl}naphthalene-1-sulfonamide |
| 4 | 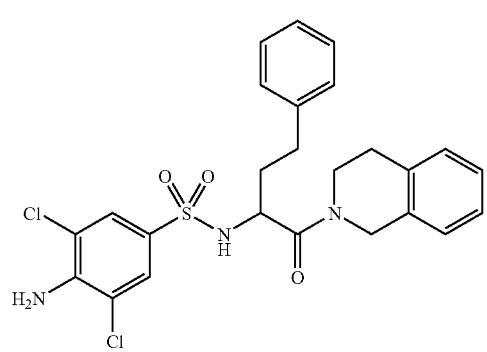 [SMILES: Nc1c(Cl)cc(S(=O)(=O)NC(CCc2ccccc2)C(=O)N2CCc3ccccc3C2)cc1Cl] | 4-amino-3,5-dichloro-N-[1-(3,4-dihydroisoquinolin-2(1H)-ylcarbonyl)-3-phenylpropyl]benzenesulfonamide |

-continued

| No. | Structure | Name |
|---|---|---|
| 5 | 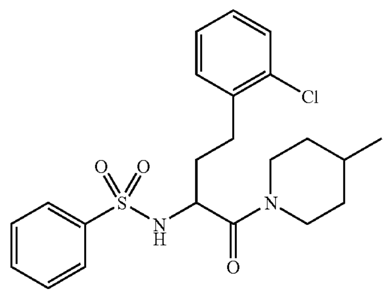 [SMILES: CC1CCN(C(=O)C(CCc2ccccc2Cl)NS(=O)(=O)c2ccccc2)CC1] | N-{3-(2-chlorophenyl)-1-[(4-methylpiperidin-1-yl)]propyl}benzenesulfonamide |
| 6 | 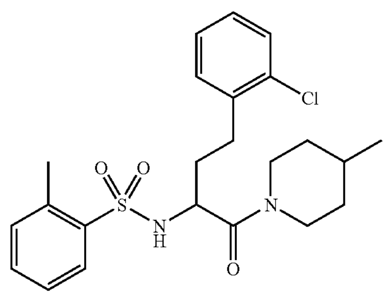 | N-{3-(2-chlorophenyl)-1-[(4-methylpiperidin-1-yl)carbonyl]propyl}-2-methylbenzenesulfonamide |
| 7 | 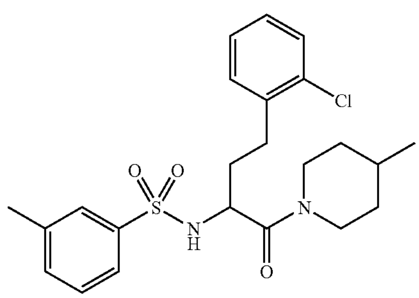 | N-{3-(2-chlorophenyl)-1-[(4-methylpiperidin-1-yl)carbonyl]propyl}-3-methylbenzenesulfonamide |
| 8 | 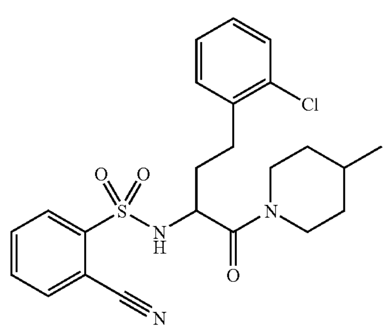 [SMILES: CC1CCN(C(=O)C(CCc2ccccc2Cl)NS(=O)(=O)c2ccccc2C#N)CC1] | N-{3-(2-chlorophenyl)-1-[(4-methylpiperidin-1-yl)carbonyl]propyl}-2-cyanobenzenesulfonamide |
| 9 | 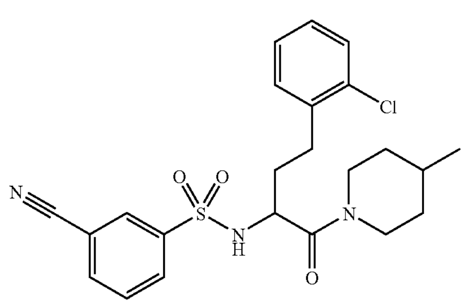 [SMILES: CC1CCN(C(=O)C(CCc2ccccc2Cl)NS(=O)(=O)c2cccc(C#N)c2)CC1] | N-{3-(2-chlorophenyl)-1-[(4-methylpiperidin-1-yl)carbonyl]propyl}-3-cyanobenzenesulfonamide |

-continued

| No. | Structure | Name |
|---|---|---|
| 10 | 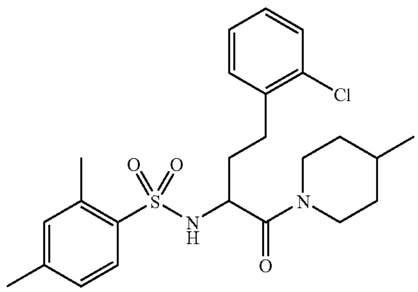 | N-{3-(2-chlorophenyl)-1-[(4-methylpiperidin-1-yl)carbonyl]propyl}-2,4-dimethylbenzenesulfonamide |
| 11 | 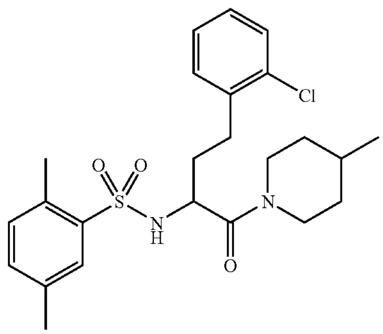 [SMILES: Cc1ccc(C)c(S(=O)(=O)NC(CCc2ccccc2Cl)C(=O)N2CCC(C)CC2)c1] | N-{3-(2-chlorophenyl)-1-[(4-methylpiperidin-1-yl)carbonyl]propyl}-2,5-dimethylbenzenesulfonamide |
| 12 | 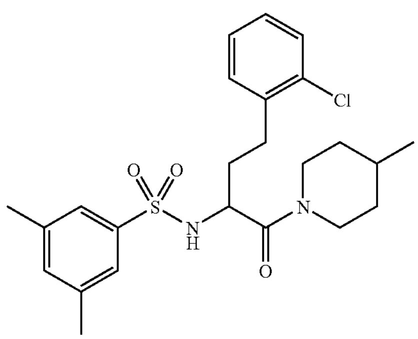 | N-{3-(2-chlorophenyl)-1-[(4-methylpiperidin-1-yl)carbonyl]propyl}-3,5-dimethylbenzenesulfonamide |
| 13 | 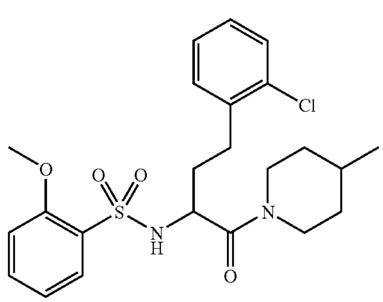 [SMILES: COc1ccccc1S(=O)(=O)NC(CCc1ccccc1Cl)C(=O)N1CCC(C)CC1] | N-{3-(2-chlorophenyl)-1-[(4-methylpiperidin-1-yl)carbonyl]propyl}-2-methoxybenzenesulfonamide |
| 14 | 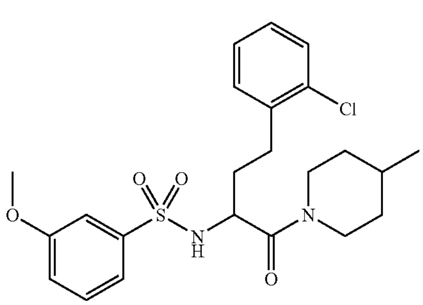 [SMILES: COc1cccc(S(=O)(=O)NC(CCc2ccccc2Cl)C(=O)N2CCC(C)CC2)c1] | N-{3-(2-chlorophenyl)-1-[(4-methylpiperidin-1-yl)carbonyl]propyl}-3-methoxybenzenesulfonamide |

-continued

| No. | Structure | Name |
|---|---|---|
| 15 | 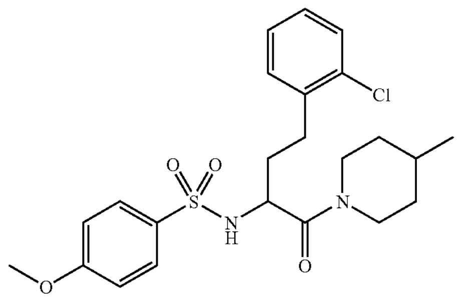 | N-{3-(2-chlorophenyl)-1-[(4-methylpiperidin-1-yl)carbonyl]propyl}-4-methoxybenzenesulfonamide |
| 16 | 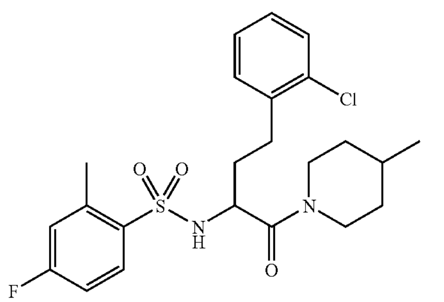 [SMILES: Cc1cc(F)ccc1S(=O)(=O)NC(CCc1ccccc1Cl)C(=O)N1CCC(C)CC1] | N-{3-(2-chlorophenyl)-1-[(4-methylpiperidin-1-yl)carbonyl]propyl}-4-fluoro-2-methylbenzenesulfonamide |
| 17 | 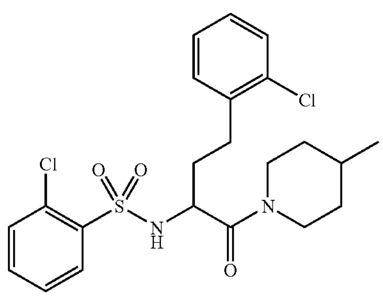 [SMILES: CC1CCN(C(=O)C(CCc2ccccc2Cl)NS(=O)(=O)c2ccccc2Cl)CC1] | 2-chloro-N-{3-(2-chlorophenyl)-1-[(4-methylpiperidin-1-yl)carbonyl]propyl}benzenesulfonamide |
| 18 | 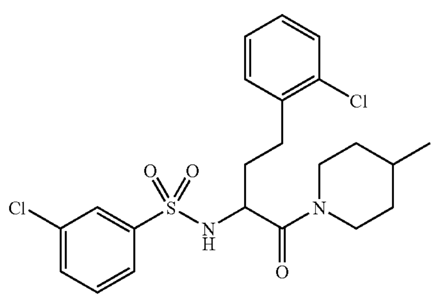 [SMILES: CC1CCN(C(=O)C(CCc2ccccc2Cl)NS(=O)(=O)c2cccc(Cl)c2)CC1] | 3-chloro-N-{3-(2-chlorophenyl)-1-[(4-methylpiperidin-1-yl)carbonyl]propyl}benzenesulfonamide |
| 19 | 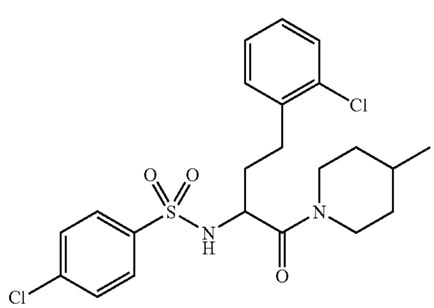 [SMILES: CC1CCN(C(=O)C(CCc2ccccc2Cl)NS(=O)(=O)c2ccc(Cl)cc2)CC1] | 4-chloro-N-{3-(2-chlorophenyl)-1-[(4-methylpiperidin-1-yl)carbonyl]propyl}benzenesulfonamide |

-continued

| No. | Structure | Name |
|---|---|---|
| 20 | 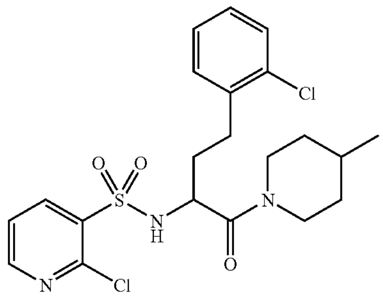 [SMILES: CC1CCN(C(=O)C(CCc2ccccc2Cl)NS(=O)(=O)c2cccnc2Cl)CC1] | 2-chloro-N-{3-(2-chlorophenyl)-1-[(4-methylpiperidin-1-yl)carbonyl]propyl}pyridine-3-sulfonamide |
| 21 | 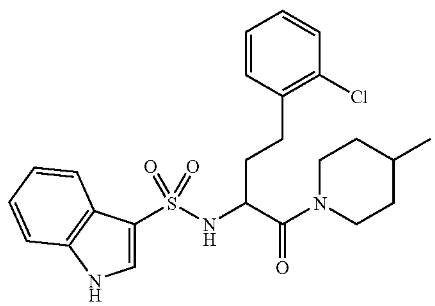 [SMILES: CC1CCN(C(=O)C(CCc2ccccc2Cl)NS(=O)(=O)c2c[nH]c3ccccc23)CC1] | N-{3-(2-chlorophenyl)-1-[(4-methylpiperidin-1-yl)carbonyl]propyl}-1H-indole-3-sulfonamide |
| 22 | 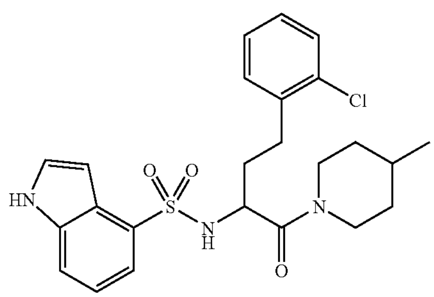 | N-{3-(2-chlorophenyl)-1-[(4-methylpiperidin-1-yl)carbonyl]propyl}-1H-indole-4-sulfonamide |
| 23 | 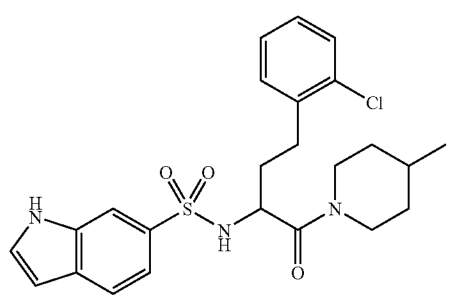 [SMILES: CC1CCN(C(=O)C(CCc2ccccc2Cl)NS(=O)(=O)c2ccc3cc[nH]c3c2)CC1] | N-{3-(2-chlorophenyl)-1-[(4-methylpiperidin-1-yl)carbonyl]propyl}-1H-indole-6-sulfonamide |
| 24 | 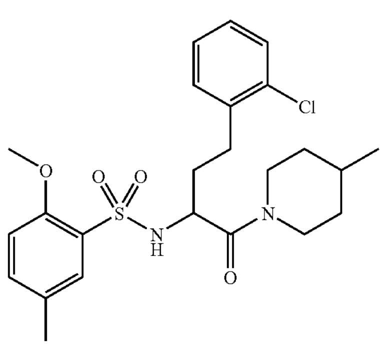 [SMILES: COc1ccc(C)cc1S(=O)(=O)NC(CCc1ccccc1Cl)C(=O)N1CCC(C)CC1] | N-{3-(2-chlorophenyl)-1-[(4-methylpiperidin-1-yl)carbonyl]propyl}-2-methoxy-5-methylbenzenesulfonamide |

-continued

| No. | Structure | Name |
|---|---|---|
| 25 | 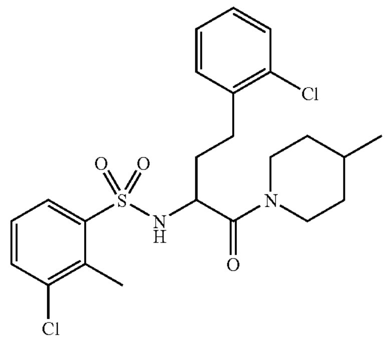 [SMILES: Cc1c(Cl)cccc1S(=O)(=O)NC(CCc1ccccc1Cl)C(=O)N1CCC(C)CC1] | 3-chloro-N-{3-(2-chlorophenyl)-1-[(4-methylpiperidin-1-yl)carbonyl]propyl}-2-methylbenzenesulfonamide |
| 26 | 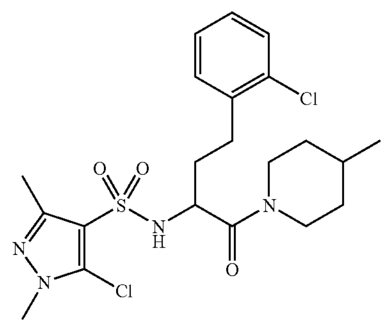 [SMILES: Cc1nn(C)c(Cl)c1S(=O)(=O)NC(CCc1ccccc1Cl)C(=O)N1CCC(C)CC1] | 5-chloro-N-{3-(2-chlorophenyl)-1-[(4-methylpiperidin-1-yl)carbonyl]propyl}-1,3-dimethyl-1H-pyrazole-4-sulfonamide |
| 27 | 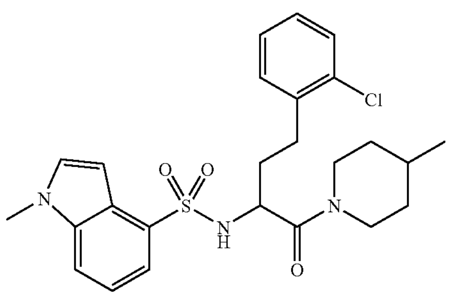 | N-{3-(2-chlorophenyl)-1-[(4-methylpiperidin-1-yl)carbonyl]propyl}-1-methyl-1H-indole-4-sulfonamide |
| 28 | 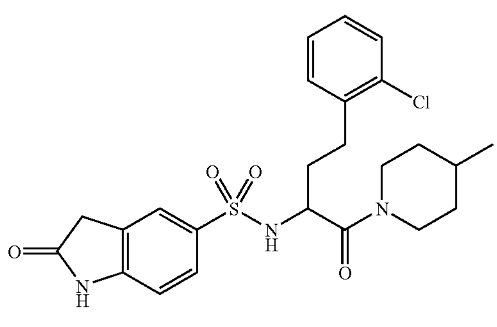 [SMILES: CC1CCN(C(=O)C(CCc2ccccc2Cl)NS(=O)(=O)c2ccc3c(c2)CC(=O)N3)CC1] | N-{3-(2-chlorophenyl)-1-[(4-methylpiperidin-1-yl)carbonyl]propyl}-2-oxo-2,3-dihydro-1H-indole-5-sulfonamide |
| 29 | 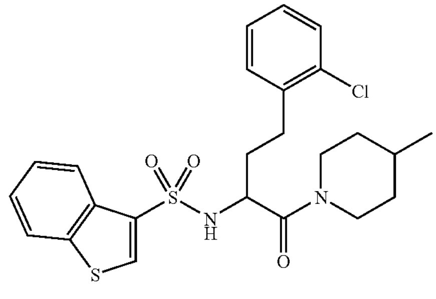 [SMILES: CC1CCN(C(=O)C(CCc2ccccc2Cl)NS(=O)(=O)c2csc3ccccc23)CC1] | N-{3-(2-chlorophenyl)-1-[(4-methylpiperidin-1-yl)carbonyl]propyl}-1-benzothiophene-3-sulfonamide |

-continued

| No. | Structure | Name |
|---|---|---|
| 30 | 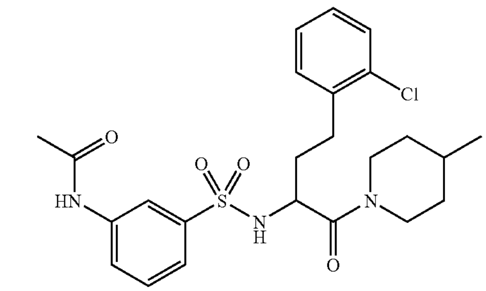 [SMILES: CC(=O)Nc1cccc(S(=O)(=O)NC(CCc2ccccc2Cl)C(=O)N2CCC(C)CC2)c1] | N-[3-({3-(2-chlorophenyl)-1-[(4-methyl-piperidin-1-yl)carbonyl]propyl}sulfamoyl)phenyl]acetamide |
| 31 | 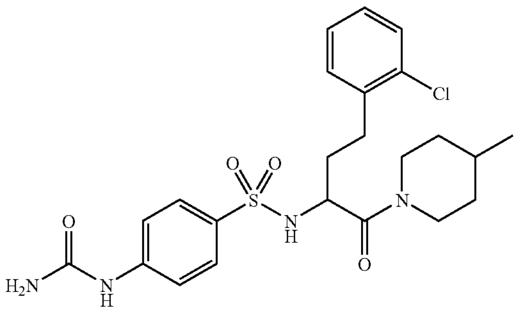 [SMILES: CC1CCN(C(=O)C(CCc2ccccc2Cl)NS(=O)(=O)c2ccc(NC(N)=O)cc2)CC1] | 4-(carbamoylamino)-N-{3-(2-chlorophenyl)-1-[(4-methylpiperidin-1-yl)carbonyl]propyl}benzenesulfonamide |
| 32 | 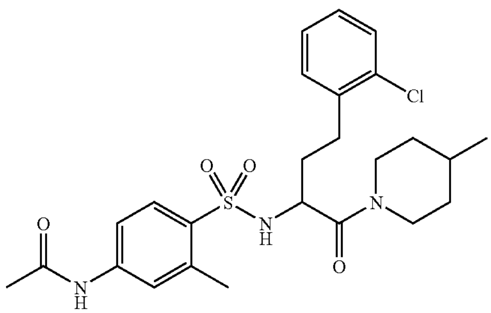 [SMILES: CC(=O)Nc1ccc(S(=O)(=O)NC(CCc2ccccc2Cl)C(=O)N2CCC(C)CC2)c(C)c1] | N-[4-({3-(2-chlorophenyl)-1-[(4-methylpiperidin-1-yl)carbonyl]propyl}sulfamoyl)-3-methylphenyl]acetamide |
| 33 | 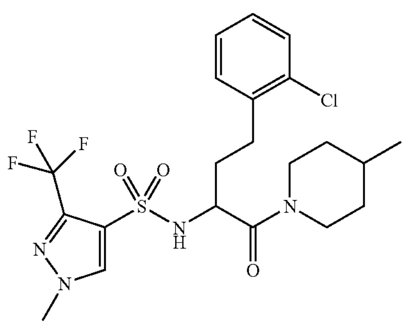 [SMILES: CC1CCN(C(=O)C(CCc2ccccc2Cl)NS(=O)(=O)c2cn(C)nc2C(F)(F)F)CC1] | N-{3-(2-chlorophenyl)-1-[(4-methylpiperidin-1-yl)carbonyl]propyl}-1-methyl-3-(trifluoromethyl)-1H-pyrazole-4-sulfonamide |
| 34 | 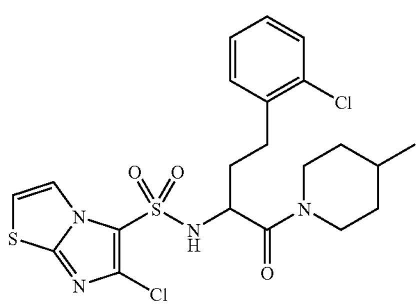 [SMILES: CC1CCN(C(=O)C(CCc2ccccc2Cl)NS(=O)(=O)c2c(Cl)nc3sccn23)CC1] | 6-chloro-N-{3-(2-chlorophenyl)-1-[(4-methylpiperidin-1-yl)carbonyl]propyl}imidazo[2,1-b][1,3]thiazole-5-sulfonamide |

-continued

| No. | Structure | Name |
|---|---|---|
| 35 | 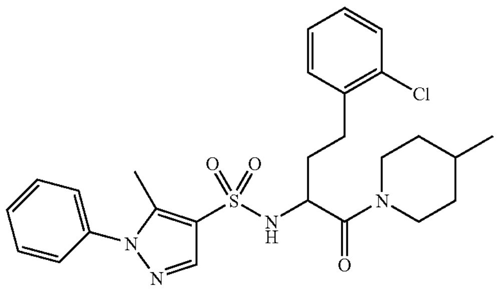 [SMILES: Cc1c(S(=O)(=O)NC(CCc2ccccc2Cl)C(=O)N2CCC(C)CC2)cnn1-c1ccccc1] | N-{3-(2-chlorophenyl)-1-[(4-methylpiperidin-1-yl)carbonyl]propyl}-5-methyl-1-phenyl-1H-pyrazole-4-sulfonamide |
| 36 | 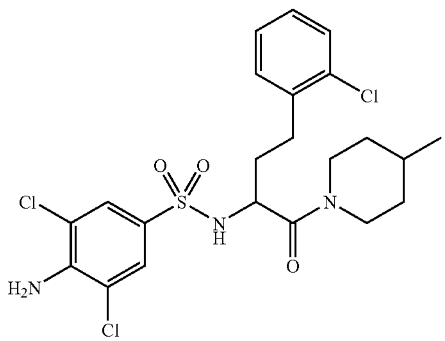 | 4-amino-3,5-dichloro-N-{3-(2-chlorophenyl)-1-[(4-methylpiperidin-1-yl)carbonyl]propyl}benzenesulfonamide |
| 37 | 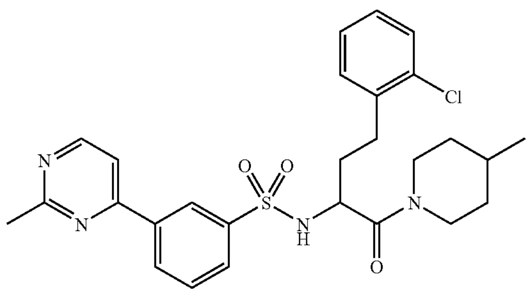 | N-{3-(2-chlorophenyl)-1-[(4-methylpiperidin-1-yl)carbonyl]propyl}-3-(2-methylpyrimidin-4-yl)benzenesulfonamide |
| 38 | 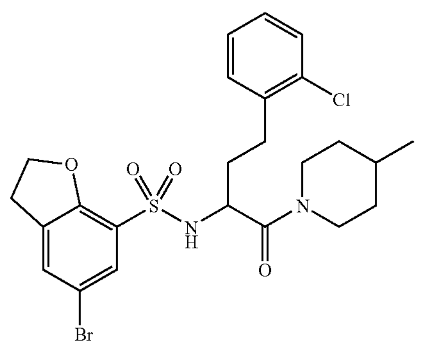 [SMILES: CC1CCN(C(=O)C(CCc2ccccc2Cl)NS(=O)(=O)c2cc(Br)cc3c2OCC3)CC1] | 5-bromo-N-{3-(2-chlorophenyl)-1-[(4-methylpiperidin-1-yl)carbonyl]propyl}-sulfonamide 2,3-dihydro-1-benzofuran-7-sulfonamide |
| 39 | Chiral | (2R)-N-benzyl-N-methyl-2-{[(2-methylphenyl)sulfonyl]amino}-4-phenylbutanamide |

| No. | Structure | | Name |
|---|---|---|---|
| 40 | 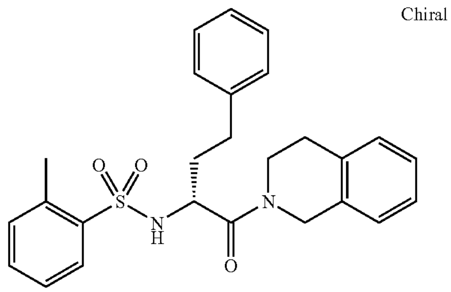 [SMILES: Cc1ccccc1S(=O)(=O)N[C@H](CCc1ccccc1)C(=O)N1CCc2ccccc2C1] | Chiral | N-[(1R)-1-(3,4-dihydroisoquinolin-2(1H)-ylcarbonyl)-3-phenylpropyl]-2-methylbenzenesulfonamide |
| 41 | 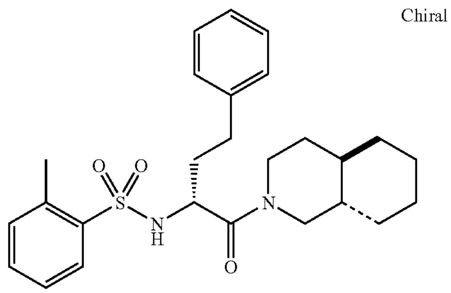 | Chiral | 2-methyl-N-{(1R)-1-[(trans)-octahydroisoquinolin-2(1H)-ylcarbonyl]-3-phenyipropyl}benzenesulfonamide |
| 42 | 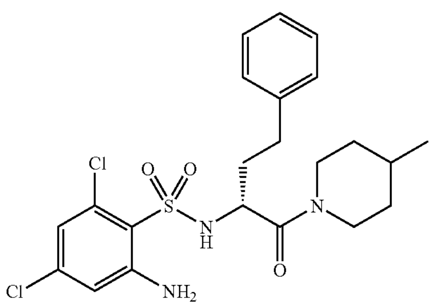 | Chiral | 2-amino-4,6-dichloro-N-{(1R)-1-[(4-methylpiperidin-1-yl)carbonyl]-3-phenylpropyl}benzenesulfonamide |
| 43 | 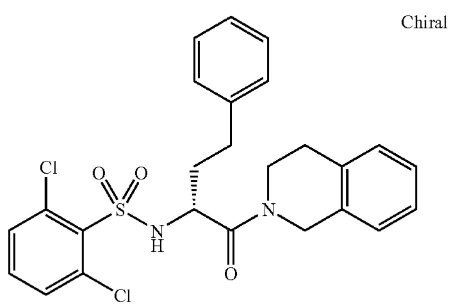 [SMILES: O=C([C@@H](CCc1ccccc1)NS(=O)(=O)c1c(Cl)cccc1Cl)N1CCc2ccccc2C1] | Chiral | 2,6-dichloro-N-[(1R)-1-(3,4-dihydroisoquinolin-2(1H)-ylcarbonyl)-3-phenylpropyl]benzenesulfonamide |
| 44 | 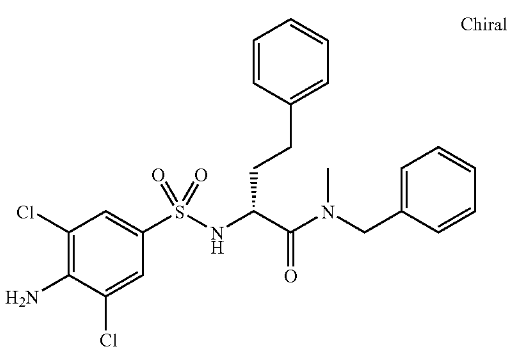 [SMILES: CN(Cc1ccccc1)C(=O)[C@@H](CCc1ccccc1)NS(=O)(=O)c1cc(Cl)c(N)c(Cl)c1] | Chiral | (2R)-2-{[(4-amino-3,5-dichlorophenyl)sulfonyl]amino}-N-benzyl-N-methyl-4-phenylbutanamide |

-continued

| No. | Structure | Name |
|---|---|---|
| 45 | 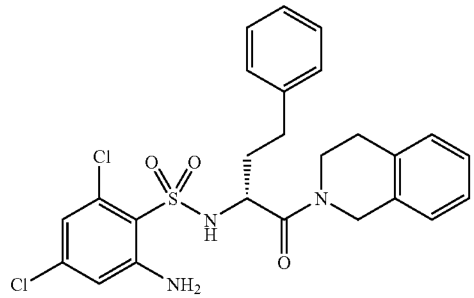 [SMILES: Nc1cc(Cl)cc(Cl)c1S(=O)(=O)N[C@H](CCc1ccccc1)C(=O)N1CCc2ccccc2C1] | 2-amino-4,6-dichloro-N-[(1R)-1-(3,4-dihydroisoquinolin-2(1H)-ylcarbonyl)-3-phenylpropyl]benzenesulfonamide |
| 46 | 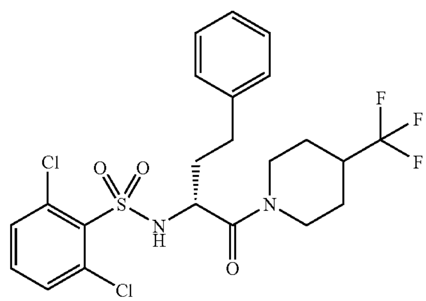 [SMILES: O=C([C@@H](CCc1ccccc1)NS(=O)(=O)c1c(Cl)cccc1Cl)N1CCC(C(F)(F)F)CC1] | 2,6-dichloro-N-[(1R)-3-phenyl-1-{[4-(trifluoromethyl)piperidin-1-yl]carbonyl}propyl]benzenesulfonamide |
| 47 | Chiral | 4-amino-3,5-dichloro-N-[(1R)-3-phenyl-1-{[4-(trifluoromethyl)piperidin-1-yl]carbonyl}propyl]benzenesulfonamide |
| 48 | Chiral | 2,6-dichloro-N-{(1R)-1-[(4-methylpiperidin-1-yl)carbonyl]-3-phenylpropyl}benzenesulfonamide |
| 49 | Chiral | N-{(1R)-1-[(4-methylpiperidin-1-yl)carbonyl]-3-phenylpropyl}-1H-indole-4-sulfonamide |

-continued

| No. | Structure | | Name |
|---|---|---|---|
| 50 | 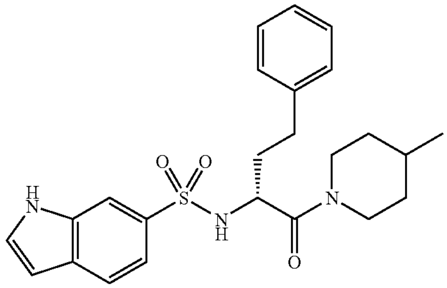 | Chiral | N-{(1R)-1-[(4-methylpiperidin-1-yl)carbonyl]-3-phenylpropyl}-1H-indole-6-sulfonamide |
| 51 | 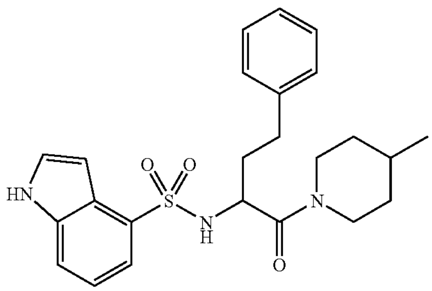 | Chiral | N-{1-[(4-methylpipendin-1-yl)carbonyl]-3-pyridin-2-ylpropyl}-1H-indole-4-sulfonamide |
| 52 | 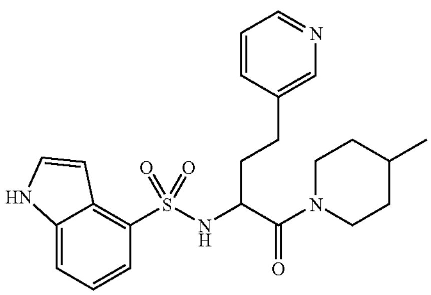 | | N-{1-[(4-methylpiperidin-1-yl)carbonyl]-3-pyridin-3-ylpropyl}-1H-indole-4-sulfonamide |
| 53 | 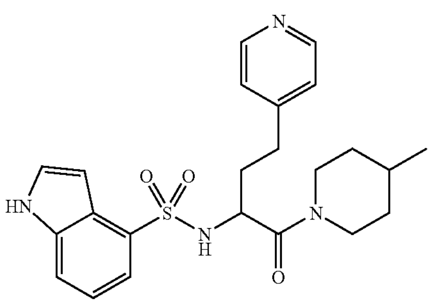 [SMILES: CC1CCN(C(=O)C(CCc2ccncc2)NS(=O)(=O)c2cccc3[nH]ccc23)CC1] | | N-{1-[(4-methylpiperidin-1-yl)carbonyl]-3-pyridin-4-ylpropyl}-1H-indole-4-sulfonamide |
| 54 | 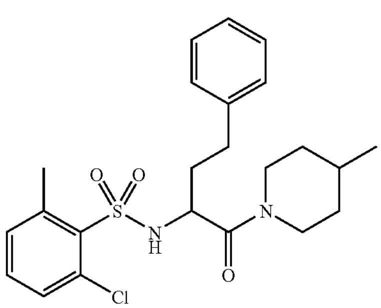 [SMILES: Cc1cccc(Cl)c1S(=O)(=O)NC(CCc1ccccc1)C(=O)N1CCC(C)CC1] | | 2-chloro-6-methyl-N-{1-[(4-methylpiperidin-1-yl)carbonyl]-3-phenylpropyl}benzenesulfonamide |

-continued

| No. | Structure | Name |
|---|---|---|
| 55 | 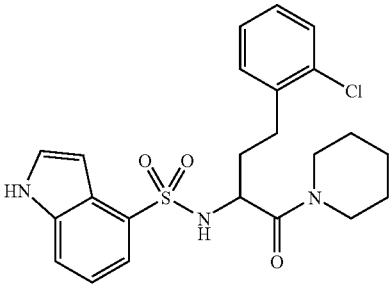 [SMILES: O=C(C(CCc1ccccc1Cl)NS(=O)(=O)c1cccc2[nH]ccc12)N1CCCCC1] | N-[3-(2-chlorophenyl)-1-(piperidin-1-ylcarbonyl)propyl]-1H-indole-4-sulfonamide |
| 56 | 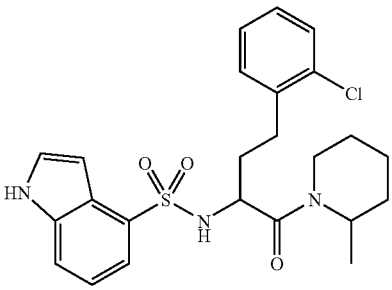 | N-{3-(2-chlorophenyl)-1-[(2-methylpiperidin-1-yl)carbonyl]propyl}-1H-indole-4-sulfonamide |
| 57 | 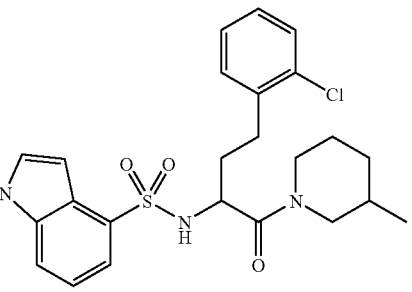 | N-{3-(2-chlorophenyl)-1-[(3-methylpiperidin-1-yl)carbonyl]propyl1-1H-indole-4-sulfonamide |
| 58 | 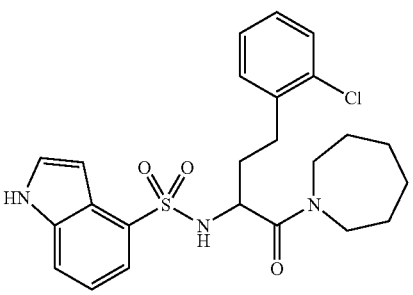 [SMILES: O=C(C(CCc1ccccc1Cl)NS(=O)(=O)c1cccc2[nH]ccc12)N1CCCCCC1] | N-[l-(azepan-1-ylcarbonyl)-3-(2-chlorophenyl)propyl]-1H-indole-4-sulfonamide |
| 59 | 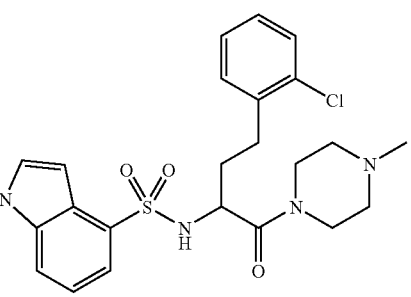 | N-{3-(2-chlorophenyl)-1-[(4-methylpiperazin-1-yl)carbonyl]propyl}-1H-indole-4-sulfonamide |

| No. | Structure | Name |
| --- | --- | --- |
| 60 | 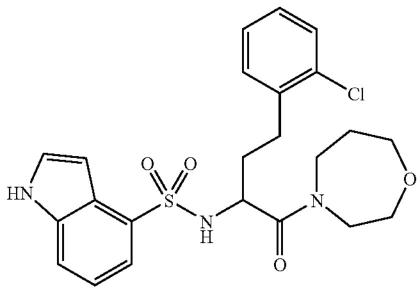 [SMILES: O=C(C(CCc1ccccc1Cl)NS(=O)(=O)c1cccc2[nH]ccc12)N1CCCOCC1] | N-[3-(2-chlorophenyl)-1-(1,4-oxazepan-4-ylcarbonyl)propyl]-1H-indole-4-sulfonamide |
| 61 | 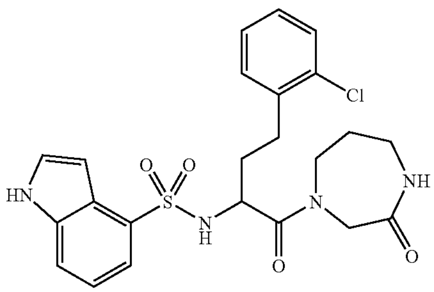 [SMILES: O=C1CN(C(=O)C(CCc2ccccc2Cl)NS(=O)(=O)c2cccc3[nH]ccc23)CCCN1] | N-{3-(2-chlorophenyl)-1-[(5-oxo-1,4-diazepan-1-yl)carbonyl]propyl}-1H-indole-4-sulfonamide |
| 62 | 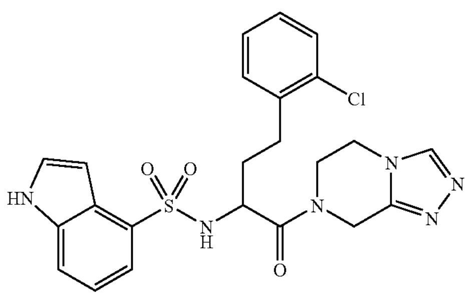 [SMILES: O=C(C(CCc1ccccc1Cl)NS(=O)(=O)c1cccc2[nH]ccc12)N1CCn2cnnc2C1] | N-[3-(2-chlorophenyl)-1-(5,6-dihydro[1,2,4]triazolo[4,3-a]pyrazin-7(8H)-ylcarbonyl)propyl]-1H-indole-4-sulfonamide |
| 63 | 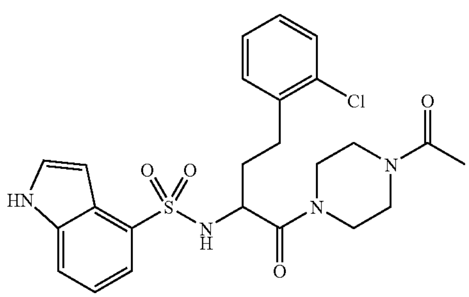 [SMILES: CC(=O)N1CCN(C(=O)C(CCc2ccccc2Cl)NS(=O)(=O)c2cccc3[nH]ccc23)CC1] | N-{1-[(4-acetylpiperazin-1-yl)carbonyl]-3-(2-chlorophenyl)propyl}-1H-indole-4-sulfonamide |
| 67 | 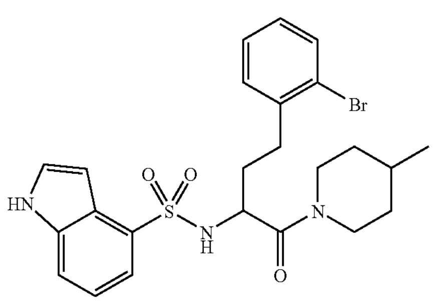 | N-{3-(2-bromophenyl)-1-[(4-methylpiperidin-1-yl)carbonyl]propyl}-1H-indole-4-sulfonamide |

-continued

| No. | Structure | Name |
|---|---|---|
| 68 | 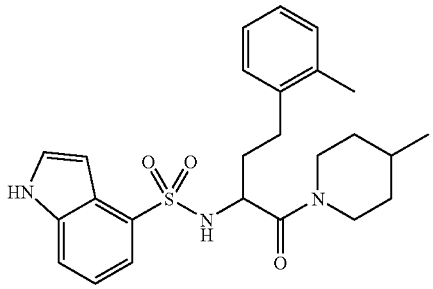 [SMILES: Cc1ccccc1CCC(NS(=O)(=O)c1cccc2[nH]ccc12)C(=O)N1CCC(C)CC1] | N-{3-(2-methylphenyl)-1-[(4-methylpiperidin-1-yl)carbonyl]propyl}-1H-indole-4-sulfonamide |
| 69 | 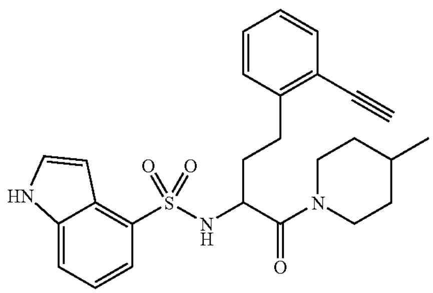 [SMILES: C#Cc1ccccc1CCC(NS(=O)(=O)c1cccc2[nH]ccc12)C(=O)N1CCC(C)CC1] | N-{3-(2-ethynylphenyl)-1-[(4-methylpiperidin-1-yl)carbonyl]propyl}-1H-indole-4-sulfonamide |
| 70 | 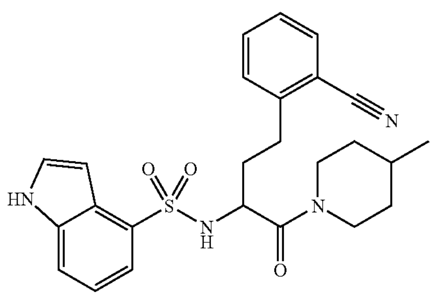 | N-{3-(2-cyanophenyl)-1-[(4-methylpiperidin-1-yl)carbonyl]propyl}-1H-indole-4-sulfonamide |
| 71 | 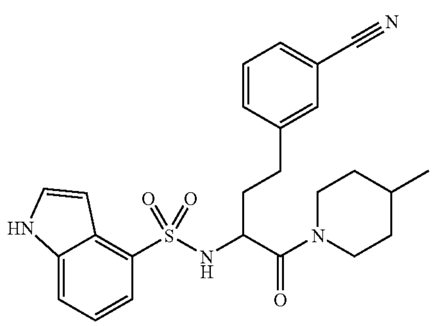 [SMILES: CC1CCN(C(=O)C(CCc2cccc(C#N)c2)NS(=O)(=O)c2cccc3[nH]ccc23)CC1] | N-{3-(3-cyanophenyl)-1-[(4-methylpiperidin-1-yl)carbonyl]propyl}-1H-indole-4-sulfonamide |
| 72 | 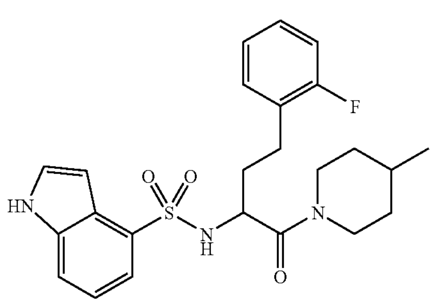 | N-{3-(2-fluorophenyl)-1-[(4-methylpiperidin-1-yl)carbonyl]propyl}-1H-indole-4-sulfonamide |

-continued

| No. | Structure | Name |
|---|---|---|
| 73 | 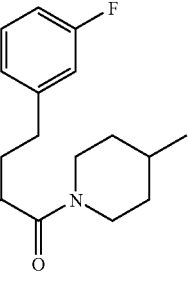 | N-{3-(3-fluorophenyl)-1-[(4-methylpiperidin-1-yl)carbonyl]propyl}-1H-indole-4-sulfonamide |
| 74 | 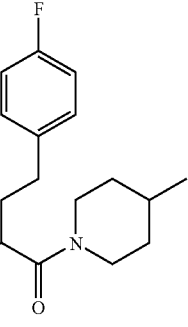 | N-{3-(4-fluorophenyl)-1-[(4-methylpiperidin-1-yl)carbonyl]propyl}-1H-indole-4-sulfonamide |
| 75 | 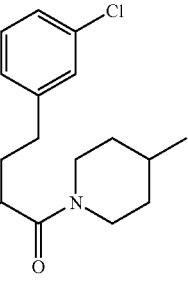 | N-{3-(3-chlorophenyl)-1-[(4-methylpiperidin-1-yl)carbonyl]propyl}-1H-indole-4-sulfonamide |
| 76 | 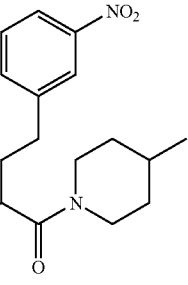 | N-{1-[(4-methylpiperidin-1-yl)carbonyl]-3-(3-nitrophenyl)propyl}-1H-indole-4-sulfonamide |
| 77 | 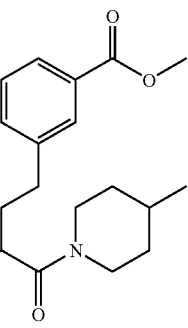 | methyl 3-{3-[(1H-indol-4-ylsulfonyl)amino]-4-(4-methylpiperidin-1-yl)-4-oxobutyl}benzoate |

| No. | Structure | Name |
|---|---|---|
| 78 | 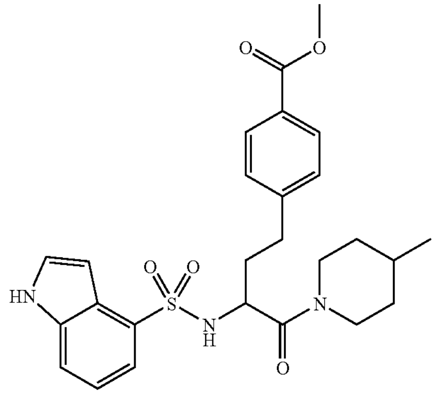 [SMILES: COC(=O)c1ccc(CCC(NS(=O)(=O)c2cccc3[nH]ccc23)C(=O)N2CCC(C)CC2)cc1] | methyl 4-{3-[(1H-indol-4-ylsulfonyl)amino]-4-(4-methylpiperidin-1-yl)-4-oxobutyl}benzoate |
| 79 | 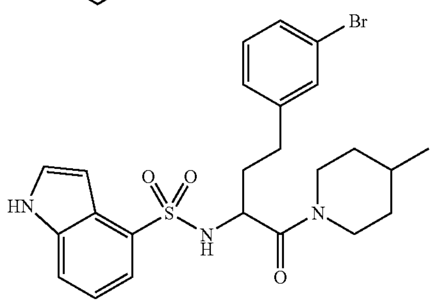 | N-{3-(3-bromophenyl)-1-[(4-methylpiperidin-1-yl)carbonyl]propyl}-1H-indole-4-sulfonamide |
| 80 | 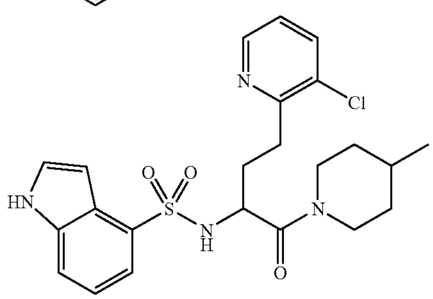 | N-{3-(3-chloropyridin-2-yl)-1-[(4-methylpiperidin-1-yl)carbonyl]propyl}-1H-indole-4-sulfonamide |
| 81 | 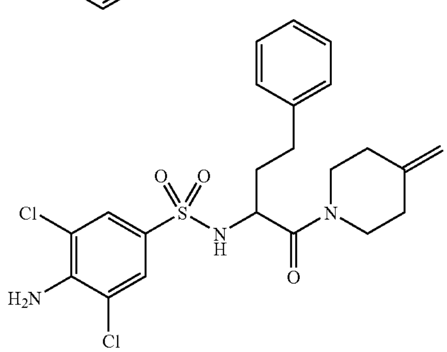 | N-{1-[(4-methylpiperidin-1-yl)carbonyl]-3-(2-prop-1-yn-1-ylphenyl)propyl}-1H-indole-4-sulfonamide |
| 82 | 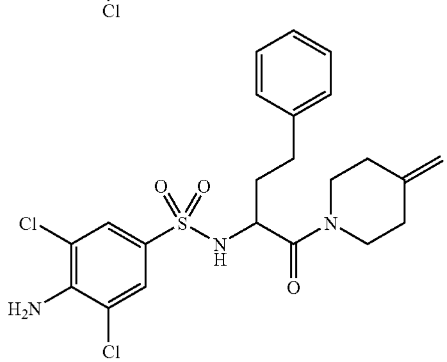 | 4-amino-3,5-dichloro-N-{1-[(4-methylidenepiperidin-1-yl)carbonyl]-3-phenylpropyl}benzenesulfonamide |

| No. | Structure | | Name |
|---|---|---|---|
| 83 | 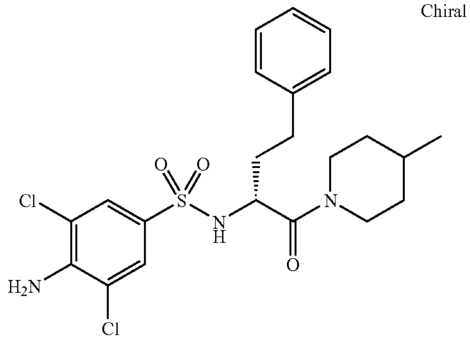 [SMILES: CC1CCN(C(=O)[C@@H](CCc2ccccc2)NS(=O)(=O)c2cc(Cl)c(N)c(Cl)c2)CC1] | Chiral | 4-amino-3,5-dichloro-N-{(1R)-1-[(4-methylpiperidin-1-yl)carbonyl]-3-phenylpropyl}benzenesulfonamide |
| 84 | 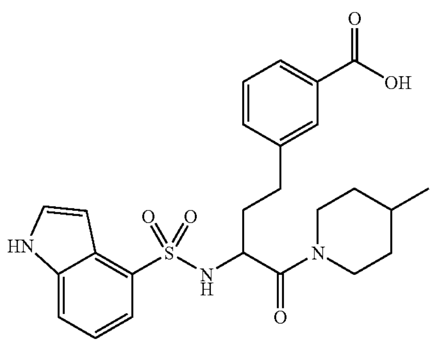 [SMILES: CC1CCN(C(=O)C(CCc2cccc(C(=O)O)c2)NS(=O)(=O)c2cccc3[nH]ccc23)CC1] | | 3-{3-[(1H-indol-4-ylsulfonyl)amino]-4-(4-methylpiperidin-1-yl)-4-oxobutyl}benzoic acid |
| 85 | 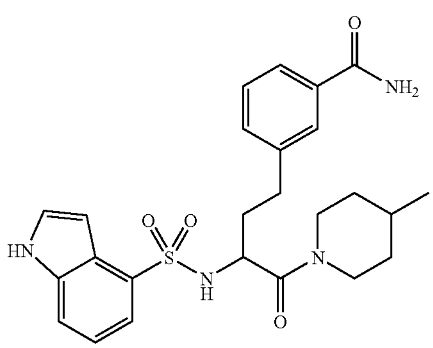 | | 3-{3-[(1H-indol-4-ylsulfonyl)amino]-4-(4-methylpiperidin-1-yl)-4-oxobutyl}benzamide |
| 86 | 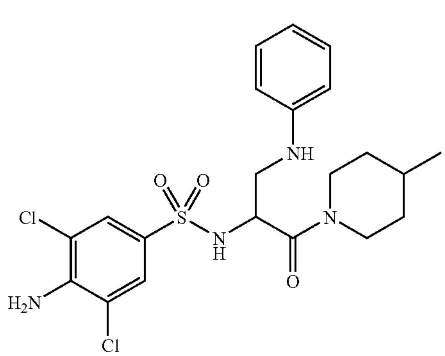 [SMILES: CC1CCN(C(=O)C(CNc2ccccc2)NS(=O)(=O)c2cc(Cl)c(N)c(Cl)c2)CC1] | | 4-amino-3,5-dichloro-N-{2-(4-methylpiperidin-1-yl)-2-oxo-1-[(phenylamino)methyl]ethyl}benzenesulfonamide |

-continued

| No. | Structure | Name |
|---|---|---|
| 87 | 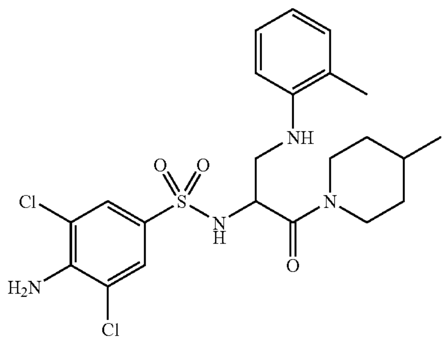 [SMILES: Cc1ccccc1NCC(NS(=O)(=O)c1cc(Cl)c(N)c(Cl)c1)C(=O)N1CCC(C)CC1] | 4-amino-3,5-dichloro-N-[1-{[(2-methylphenyl)amino]methyl}-2-(4-methylpiperidin-1-yl)-2-oxoethyl]benzenesulfonamide |
| 88 | 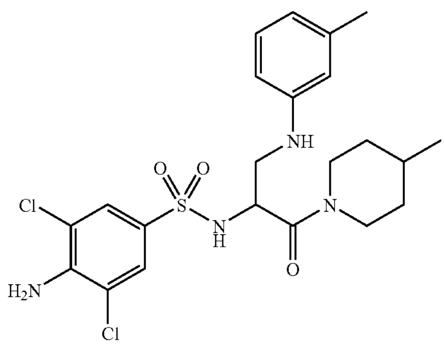 [SMILES: Cc1cccc(NCC(NS(=O)(=O)c2cc(Cl)c(N)c(Cl)c2)C(=O)N2CCC(C)CC2)c1] | 4-amino-3,5-dichloro-N-[1-{[(3-methylphenyl)amino]methyl}-2-(4-methylpiperidin-1-yl)-2-oxoethyl]benzenesulfonamide |
| 89 | 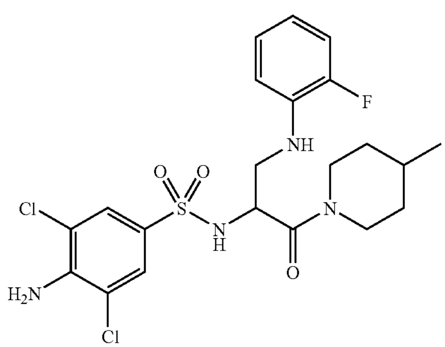 [SMILES: CC1CCN(C(=O)C(CNc2ccccc2F)NS(=O)(=O)c2cc(Cl)c(N)c(Cl)c2)CC1] | 4-amino-3,5-dichloro-N-[1-{[(2-fluorophenyl)amino]methyl}-2-(4-methylpiperidin-1-yl)-2-oxoethyl]benzenesulfonamide |
| 90 | 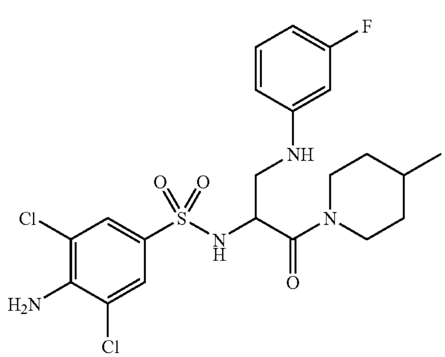 [SMILES: CC1CCN(C(=O)C(CNc2cccc(F)c2)NS(=O)(=O)c2cc(Cl)c(N)c(Cl)c2)CC1] | 4-amino-3,5-dichloro-N-[1-{[(3-fluorophenyl)amino]methyl}-2-(4-methylpiperidin-1-yl)-2-oxoethyl]benzenesulfonamide |

| No. | Structure | Name |
|---|---|---|
| 91 | 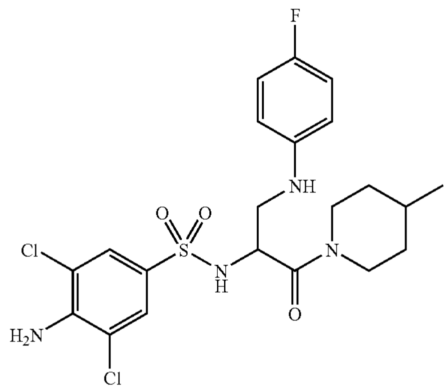 [SMILES: CC1CCN(C(=O)C(CNc2ccc(F)cc2)NS(=O)(=O)c2cc(Cl)c(N)c(Cl)c2)CC1] | 4-amino-3,5-dichloro-N-[1-{[(4-fluorophenyl)amino]methyl}-2-(4-methylpiperidin-1-yl)-2-oxoethyl]bensenesulfonamide |
| 92 | 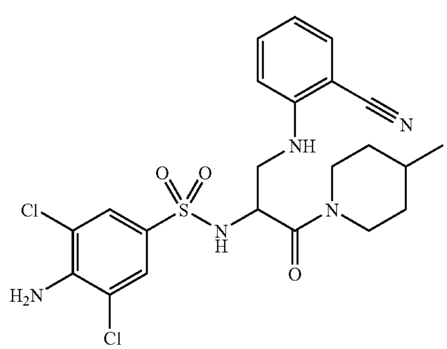 [SMILES: CC1CCN(C(=O)C(CNc2ccccc2C#N)NS(=O)(=O)c2cc(Cl)c(N)c(Cl)c2)CC1] | 4-amino-3,5-dichloro-N-[1-{[(2-cyanophenyl)amino]methyl}-2-(4-methylpiperidin-1-yl)-2-oxoethyl]benzenesulfonamide |
| 93 | 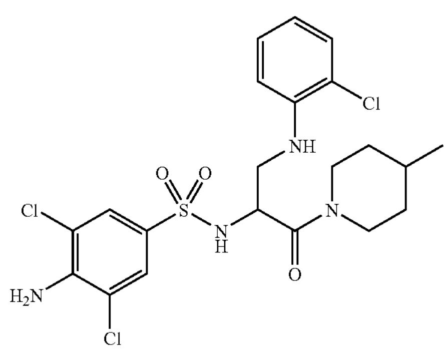 | 4-amino-3,5-dichloro-N-[1-{[(2-chlorophenyl)amino]methyl}-2-(4-methylpiperidin-1-yl)-2-oxoethyl]benzenesulfonamide |
| 94 | 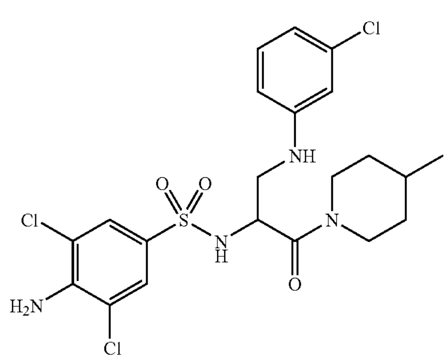 [SMILES: CC1CCN(C(=O)C(CNc2cccc(Cl)c2)NS(=O)(=O)c2cc(Cl)c(N)c(Cl)c2)CC1] | 4-amino-3,5-dichloro-N-[1-{[(3-chlorophenyl)amino]methyl}-2-(4-methylpiperidin-1-yl)-2-oxoethyl]benzenesulfonamide |

| No. | Structure | Name |
|---|---|---|
| 95 | 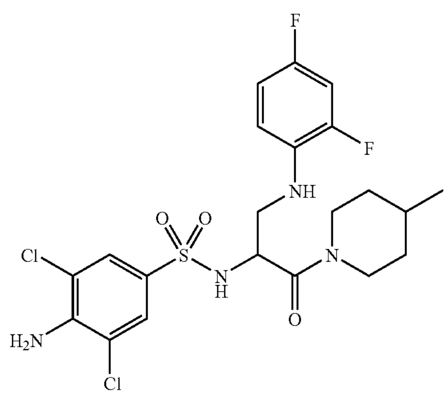 | 4-amino-3,5-dichloro-N-[1-{[(2,4-difluorophenyl)amino]methyl}-2-(4-oxoethyl]benzenesulfonamide |
| 96 | 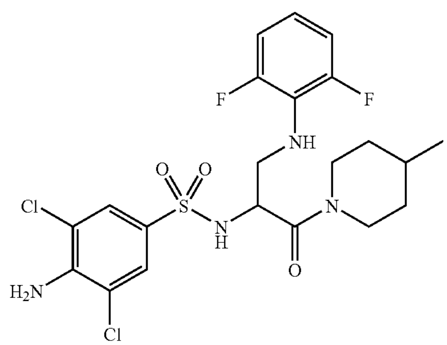 [SMILES: CC1CCN(C(=O)C(CNc2c(F)cccc2F)NS(=O)(=O)c2cc(Cl)c(N)c(Cl)c2)CC1] | 4-amino-3,5-dichloro-N-[1-{[(2,6-difluorophenyl)amino]methyl}-2-(4-methylpiperidin-1-yl)-2-oxoethyl]benzenesulfonamide |
| 97 | 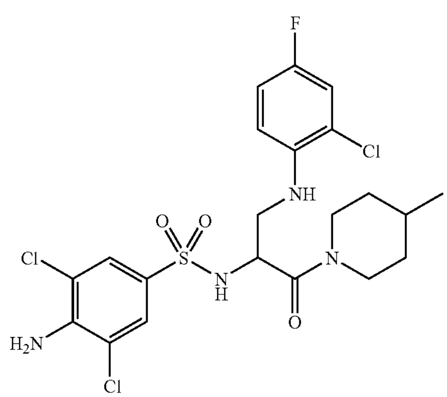 [SMILES: CC1CCN(C(=O)C(CNc2ccc(F)cc2Cl)NS(=O)(=O)c2cc(Cl)c(N)c(Cl)c2)CC1] | 4-amino-3,5-dichloro-N-[1-{[(2-chioro-4-fluorophenyl)amino]methyl}-2-(4-oxoethyl]benzenesulfonamide |
| 98 | 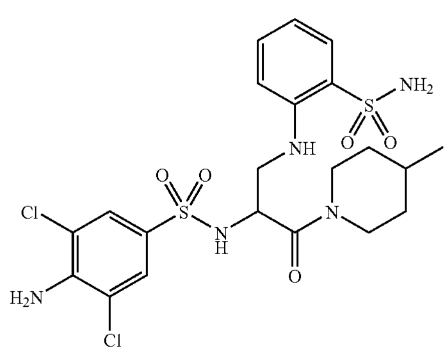 [SMILES: CC1CCN(C(=O)C(CNc2ccccc2S(N)(=O)=O)NS(=O)(=O)c2cc(Cl)c(N)c(Cl)c2)CC1] | 4-amino-3,5-dichloro-N-[2-(4-methylpiperidin-1-yl)-2-oxo-1-{[(2-sulfamoylphenyl)amino]-methyl}ethyl]benzenesulfonamide |

| No. | Structure | Name |
|---|---|---|
| 99 | 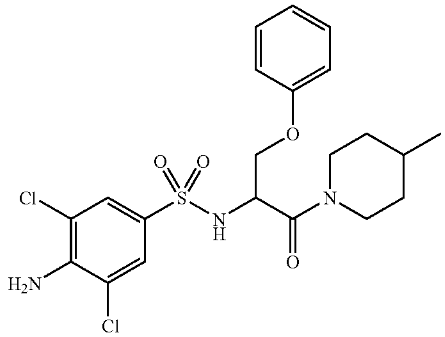 | 4-amino-3,5-dichloro-N-[2-(4-methylpiperidin-1-yl)-2-oxo-1-(phenoxymethyl)ethyl]benzenesulfonamide |
| 100 | 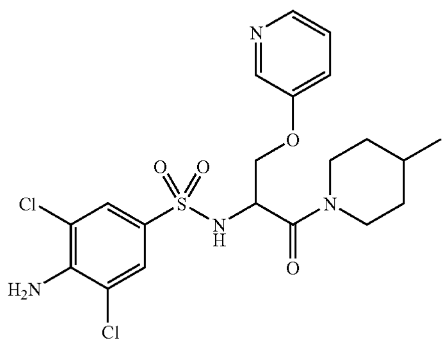 | 4-amino-3,5-dichloro-N-{2-(4-methylpiperidin-1-yl)-2-oxo-1-[(pyridin-3-yloxy)methyl]ethyl}benzenesulfonamide |
| 101 | 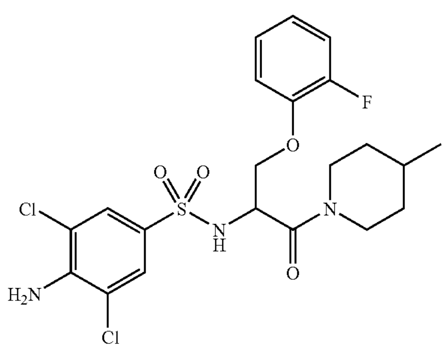 [SMILES: CC1CCN(C(=O)C(COc2ccccc2F)NS(=O)(=O)c2cc(Cl)c(N)c(Cl)c2)CC1] | 4-amino-3,5-dichloro-N-{1-[(2-fluorophenoxy)methyl]-2-(4-methylpiperidin-1-yl)-2-oxoethyl}benzenesulfonamide |
| 102 | 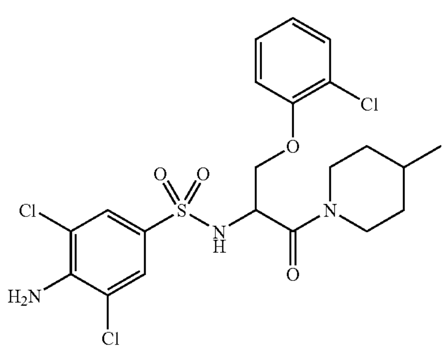 | 4-amino-3,5-dichloro-N-{1-[(2-chlorophenoxy)methyl]-2-(4-methylpiperidin-1-yl)-2-oxoethyl}benzenesulfonamide |

-continued

| No. | Structure | Name |
|---|---|---|
| 103 | 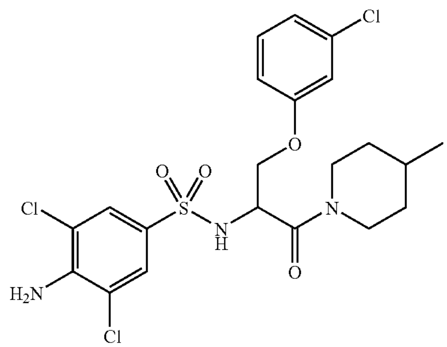 [SMILES: CC1CCN(C(=O)C(COc2cccc(Cl)c2)NS(=O)(=O)c2cc(Cl)c(N)c(Cl)c2)CC1] | 4-amino-3,5-dichloro-N-{1-[(3-chlorophenoxy)methyl]-2-(4-methylpiperidin-1-yl)-2-oxoethyl}benzenesulfonamide |
| 104 | 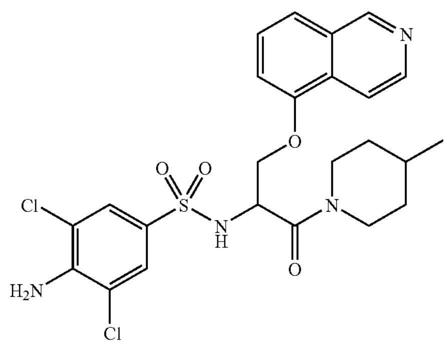 [SMILES: CC1CCN(C(=O)C(COc2cccc3cnccc23)NS(=O)(=O)c2cc(Cl)c(N)c(Cl)c2)CC1] | 4-amino-3,5-dichloro-N-{1-[(isoquinolin-5-yloxy)methyl]-2-(4-methylpiperidin-1-yl)-2-oxoethyl}benzenesulfonamide |
| 105 | 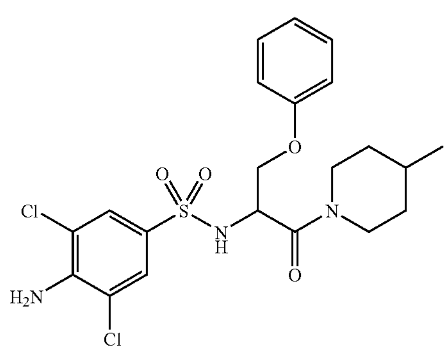 | 4-amino-3,5-dichloro-N-methylpiperidin-1-yl)-2-oxo-1-{[2-(trifluoromethyl)phenoxy]methyl}ethyl]benzenesulfonamide |
| 106 | 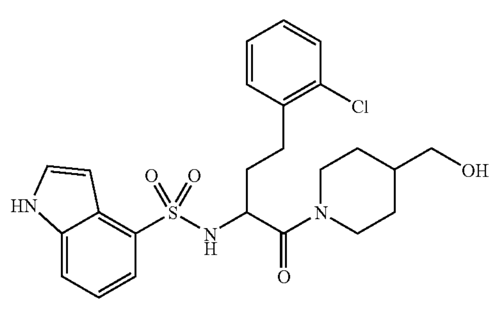 [SMILES: O=C(C(CCc1ccccc1Cl)NS(=O)(=O)c1cccc2[nH]ccc12)N1CCC(CO)CC1] | N-[3-(2-chlorophenyl)-1-{[4-(hydroxymethyl)piperidin-1-yl]carbonyl}propyl]-1H-indole-4-sulfonamide |

-continued

| No. | Structure | Name |
|---|---|---|
| 107 | 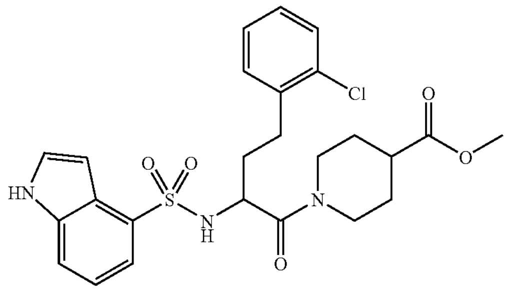 [SMILES: COC(=O)C1CCN(C(=O)C(CCc2ccccc2Cl)NS(=O)(=O)c2cccc3[nH]ccc23)CC1] | methyl 1-{4-(2-chlorophenyl)-2-[(1H-indol-4-ylsulfonyl)amino]butanoyl}piperidine 4-carboxylate |
| 108 | 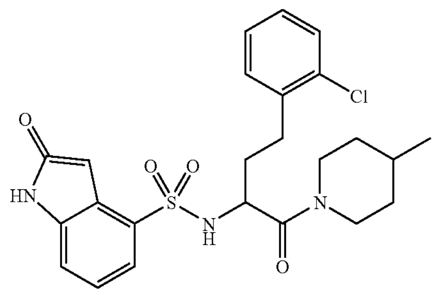 | N-{3-(2-chlorophenyl)-1-[(4-methylpiperidin-1-yl)carbonyl]propyl}-2-oxo-2,3-dihydro-1H-indole-4-sulfonamide |
| 109 | 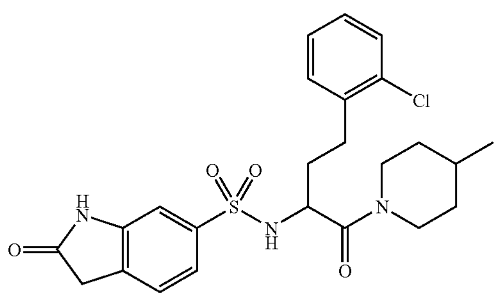 [SMILES: CC1CCN(C(=O)C(CCc2ccccc2Cl)NS(=O)(=O)c2ccc3c(c2)NC(=O)C3)CC1] | N-{3-(2-chlorophenyl)-1-[(4-methylpiperidin-1-yl)carbonyl]propyl}-2-oxo-2,3-dihydro-1H-indole-6-sulfonamide |
| 110 | 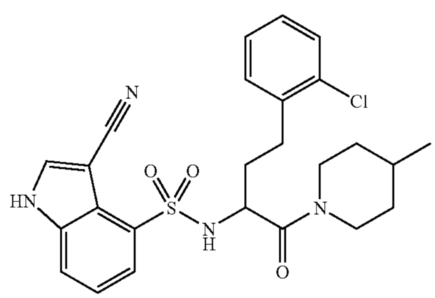 [SMILES: CC1CCN(C(=O)C(CCc2ccccc2Cl)NS(=O)(=O)c2cccc3[nH]cc(C#N)c23)CC1] | N-{3-(2-chlorophenyl)-1-[(4-methylpiperidin-1-yl)carbonyl]propyl}-3-cyano-1H-indole-4-sulfonamide |
| 111 | 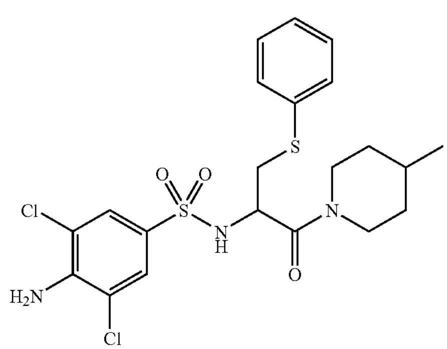 | 4-amino-3,5-dichloro-N-{2-(4-methylpiperidin-1-yl)-2-oxo-1-[(phenylsulfanyl)methyl]ethyl}benzenesulfonamide |

| No. | Structure | Name |
|---|---|---|
| 112 | 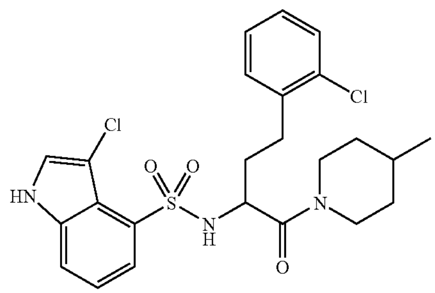 [SMILES: CC1CCN(C(=O)C(CCc2ccccc2Cl)NS(=O)(=O)c2cccc3[nH]cc(Cl)c23)CC1] | 3-chloro-N-{3(2-chlorophenyl)-1-[(4-methylpiperidin-1-yl)carbonyl]propyl}-1H-indole-4-sulfonamide |
| 113 | 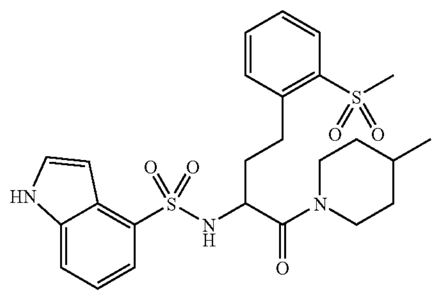 [SMILES: CC1CCN(C(=O)C(CCc2ccccc2S(C)(=O)=O)NS(=O)(=O)c2cccc3[nH]ccc23)CC1] | N-{1-[(4-methylpiperidin-1-yl)carbonly]-3-[2-(methylsulfonyl)phenyl]propyl}-1H-indole-4-sulfonamide |
| 114 | 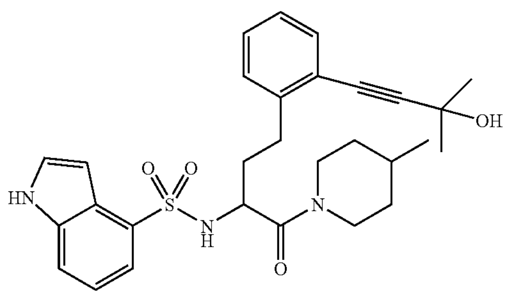 [SMILES: CC1CCN(C(=O)C(CCc2ccccc2C#CC(C)(C)O)NS(=O)(=O)c2cccc3[nH]ccc23)CC1] | N-{3-[2-(3-hydroxy-3-methylbut-1-yn-1-yl)phenyl]-1-[(4-methylpiperidin-1-yl)carbonyl]propyl}-1H-indole-4-sulfonamide |
| 115 | Chiral | 4-amino-3,5-dichloro-N-{(iS)-1-[(cis)octahydroisoquinolin-2(1H)-ylcarbonyl]-3-phenylpropyl}benzenesulfonamide |
| 116 | Chiral | 4-amino-3,5-dichloro-N-{(1)-i-[(cis)octahydroisoquinolin-2(1H)-ylcarbonyl]-3-phenylpropyl}benzenesulfonamide |

| No. | Structure | Name |
|---|---|---|
| 117 | Chiral | 4-amino-3,5-dichloro-N-{(1)-i-[(trans)-octahydroisoquinolin-2(1H)-ylcarbonyl]-3-phenylpropyl}benzenesulfonamide |
| 118 | Chiral | 4-amino-3,5-dichloro-N-{(1)-i-[(trans)-octahydroquinolin-1(2H)-ylcarbonyl]-3-phenylpropyl}benzenesulfonamide |
| 119 | 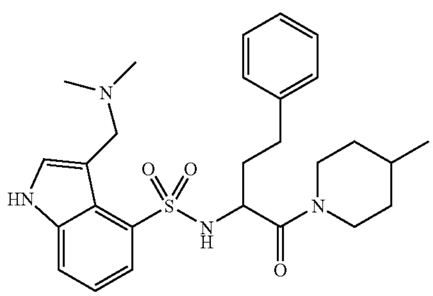 [SMILES: CC1CCN(C(=O)C(CCc2ccccc2)NS(=O)(=O)c2cccc3[nH]cc(CN(C)C)c23)CC1] | N-{3-(2-chlorophenyl)-1-[(4-methylpiperidin-1-yl)carbonyl]propyl}-3-[(dimethylamino)methyl]-1H-indole-4-sulfonamide |
| 120 | 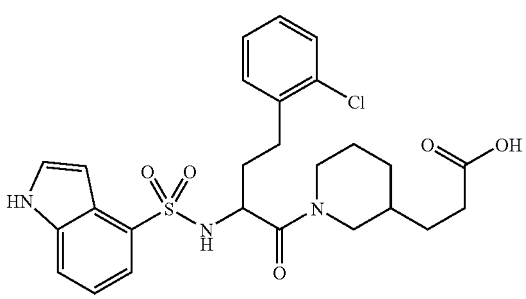 [SMILES: O=C(O)CCC1CCCN(C(=O)C(CCc2ccccc2Cl)NS(=O)(=O)c2cccc3[nH]ccc23)C1] | 3-(1-{4-(2-chlorophenyl)-2-[(1H-indol-4-ylsulfonyl)amino]butanoyl}piperidin-3-yl)propanoic acid |
| 121 | 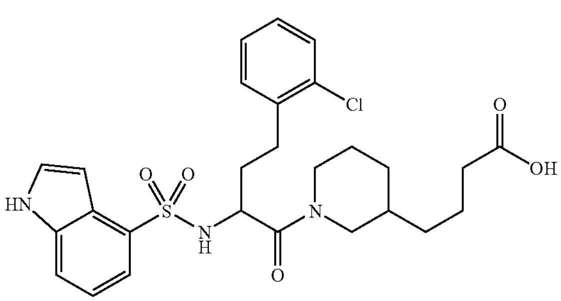 [SMILES: O=C(O)CCCC1CCCN(C(=O)C(CCc2ccccc2Cl)NS(=O)(=O)c2cccc3[nH]ccc23)C1] | 4-(1-{4-(2-chlorophenyl)-2-[(1H-indol-4-ylsulfonyl)amino]butanoyl}piperidin-3-yl)butanoic acid |

| No. | Structure | Name |
|---|---|---|
| 122 | 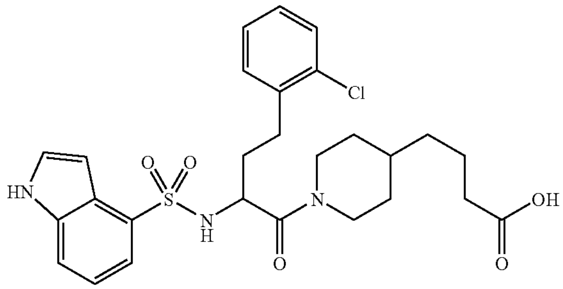 [SMILES: O=C(O)CCCC1CCN(C(=O)C(CCc2ccccc2Cl)NS(=O)(=O)c2cccc3[nH]ccc23)CC1] | 4-(1-{4-(2-chlorophenyl)-2-[(1H-indol-4-ylsulfonyl)amino]butanoyl}piperidin 4-yl)butanoic acid |
| 123 | 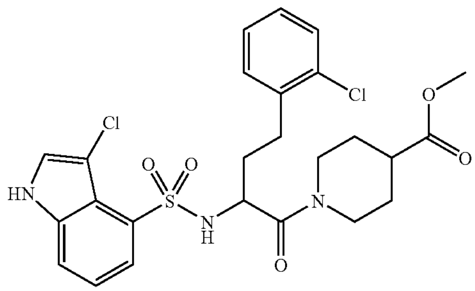 [SMILES: COC(=O)C1CCN(C(=O)C(CCc2ccccc2Cl)NS(=O)(=O)c2cccc3[nH]cc(Cl)c23)CC1] | methyl 1-[2-{[(3-chloro-1H-indol-4-yl)sulfonyl]amino}-4-(2-chlorophenyl)butanoyl]piperidine-4-carboxylate |

In still another embodiment of the invention, there are provided compounds of the formula (I) selected from the group below or a tautomer thereof or a salt thereof:

N-{3-(2-chlorophenyl)-1-[(4-methylpiperidin-1-yl)carbonyl]propyl}-2-methylbenzenesulfonamide
N-{3-(2-chlorophenyl)-1-[(4-methylpiperidin-1-yl)carbonyl]propyl}-3-methylbenzenesulfonamide
N-{3-(2-chlorophenyl)-1-[(4-methylpiperidin-1-yl)carbonyl]propyl}-2,4-dimethylbenzenesulfonamide
N-{3-(2-chlorophenyl)-1-[(4-methylpiperidin-1-yl)carbonyl]propyl}-2,5-dimethylbenzenesulfonamide
N-{3-(2-chlorophenyl)-1-[(4-methylpiperidin-1-yl)carbonyl]propyl}-3,5-dimethylbenzenesulfonamide
N-{3-(2-chlorophenyl)-1-[(4-methylpiperidin-1-yl)carbonyl]propyl}-2-methoxybenzenesulfonamide
N-{3-(2-chlorophenyl)-1-[(4-methylpiperidin-1-yl)carbonyl]propyl}-4-fluoro-2-methylbenzenesulfonamide
2-chloro-N-{3-(2-chlorophenyl)-1-[(4-methylpiperidin-1-yl)carbonyl]propyl}benzenesulfonamide
2-chloro-N-{3-(2-chlorophenyl)-1-[(4-methylpiperidin-1-yl)carbonyl]propyl}pyridine-3-sulfonamide
N-{3-(2-chlorophenyl)-1-[(4-methylpiperidin-1-yl)carbonyl]propyl}-1H-indole-3-sulfonamide
N-{3-(2-chlorophenyl)-1-[(4-methylpiperidin-1-yl)carbonyl]propyl}-1H-indole-4-sulfonamide
N-{3-(2-chlorophenyl)-1-[(4-methylpiperidin-1-yl)carbonyl]propyl}-1H-indole-6-sulfonamide
N-{3-(2-chlorophenyl)-1-[(4-methylpiperidin-1-yl)carbonyl]propyl}-2-methoxy-5-methylbenzenesulfonamide
5-chloro-N-{3-(2-chlorophenyl)-1-[(4-methylpiperidin-1-yl)carbonyl]propyl}-1,3-dimethyl-1H-pyrazole-4-sulfonamide
N-{3-(2-chlorophenyl)-1-[(4-methylpiperidin-1-yl)carbonyl]propyl}-1-methyl-1H-indole-4-sulfonamide
N-{3-(2-chlorophenyl)-1-[(4-methylpiperidin-1-yl)carbonyl]propyl}-2-oxo-2,3-dihydro-1H-indole-5-sulfonamide
N-{3-(2-chlorophenyl)-1-[(4-methylpiperidin-1-yl)carbonyl]propyl}-1-benzothiophene-3-sulfonamide
N-[4-({3-(2-chlorophenyl)-1-[(4-methylpiperidin-1-yl)carbonyl]propyl}sulfamoyl)-3-methylphenyl]acetamide
N-{3-(2-chlorophenyl)-1-[(4-methylpiperidin-1-yl)carbonyl]propyl}-1-methyl-3-(trifluoromethyl)-1H-pyrazole-4-sulfonamide
4-amino-3,5-dichloro-N-{3-(2-chlorophenyl)-1-[(4-methylpiperidin-1-yl)carbonyl]propyl}benzenesulfonamide
N-{(1R)-1-[(4-methylpiperidin-1-yl)carbonyl]-3-phenylpropyl}-1H-indole-4-sulfonamide
N-{(1R)-1-[(4-methylpiperidin-1-yl)carbonyl]-3-phenylpropyl}-1H-indole-6-sulfonamide
N-{1-[(4-methylpiperidin-1-yl)carbonyl]-3-pyridin-3-ylpropyl}-1H-indole-4-sulfonamide
N-[3-(2-chlorophenyl)-1-(piperidin-1-ylcarbonyl)propyl]-1H-indole-4-sulfonamide
N-{3-(2-chlorophenyl)-1-[(2-methylpiperidin-1-yl)carbonyl]propyl}-1H-indole-4-sulfonamide
N-{3-(2-chlorophenyl)-1-[(3-methylpiperidin-1-yl)carbonyl]propyl}-1H-indole-4-sulfonamide
N-[1-(azepan-1-ylcarbonyl)-3-(2-chlorophenyl)propyl]-1H-indole-4-sulfonamide
N-{3-(2-chlorophenyl)-1-[(4-methylpiperazin-1-yl)carbonyl]propyl}-1H-indole-4-sulfonamide
N-[3-(2-chlorophenyl)-1-(1,4-oxazepan-4-ylcarbonyl)propyl]-1H-indole-4-sulfonamide
N-{3-(2-chlorophenyl)-1-[(5-oxo-1,4-diazepan-1-yl)carbonyl]propyl}-1H-indole-4-sulfonamide
N-[3-(2-chlorophenyl)-1-(5,6-dihydro[1,2,4]triazolo[4,3-a]pyrazin-7(8H)-ylcarbonyl)propyl]-1H-indole-4-sulfonamide
N-{1-[(4-acetylpiperazin-1-yl)carbonyl]-3-(2-chlorophenyl)propyl}-1H-indole-4-sulfonamide
N-{3-(2-bromophenyl)-1-[(4-methylpiperidin-1-yl)carbonyl]propyl}-1H-indole-4-sulfonamide
N-{3-(2-methylphenyl)-1-[(4-methylpiperidin-1-yl)carbonyl]propyl}-1H-indole-4-sulfonamide
N-{3-(2-ethynylphenyl)-1-[(4-methylpiperidin-1-yl)carbonyl]propyl}-1H-indole-4-sulfonamide N-{3-(2-cyanophenyl)-1-[(4-methylpiperidin-1-yl)carbonyl]propyl}-1H-indole-4-sulfonamide
N-{3-(3-cyanophenyl)-1-[(4-methylpiperidin-1-yl)carbonyl]propyl}-1H-indole-4-sulfonamide
N-{3-(2-fluorophenyl)-1-[(4-methylpiperidin-1-yl)carbonyl]propyl}-1H-indole-4-sulfonamide
N-{3-(3-fluorophenyl)-1-[(4-methylpiperidin-1-yl)carbonyl]propyl}-1H-indole-4-sulfonamide
N-{1-[(4-methylpiperidin-1-yl)carbonyl]-3-(3-nitrophenyl)propyl}-1H-indole-4-sulfonamide
methyl 3-{3-[(1H-indol-4-ylsulfonyl)amino]-4-(4-methylpiperidin-1-yl)-4-oxobutyl}benzoate
N-{3-(3-chloropyridin-2-yl)-1-[(4-methylpiperidin-1-yl)carbonyl]propyl}-1H-indole-4-sulfonamide
N-{1-[(4-methylpiperidin-1-yl)carbonyl]-3-(2-prop-1-yn-1-ylphenyl)propyl}-1H-indole-4-sulfonamide
4-amino-3,5-dichloro-N-{(1R)-1-[(4-methylpiperidin-1-yl)carbonyl]-3-phenylpropyl}benzene sulfonamide
4-amino-3,5-dichloro-N-[1-{[(2-methylphenyl)amino]methyl}-2-(4-methylpiperidin-1-yl)-2-oxoethyl]benzenesulfonamide
4-amino-3,5-dichloro-N-[1-{[(2-fluorophenyl)amino]methyl}-2-(4-methylpiperidin-1-yl)-2-oxoethyl]benzenesulfonamide
4-amino-3,5-dichloro-N-[1-{[(2-cyanophenyl)amino]methyl}-2-(4-methylpiperidin-1-yl)-2-oxoethyl]benzenesulfonamide
4-amino-3,5-dichloro-N-[1-{[(2-chlorophenyl)amino]methyl}-2-(4-methylpiperidin-1-yl)-2-oxoethyl]benzenesulfonamide
4-amino-3,5-dichloro-N-[1-{[(2,6-difluorophenyl)amino]methyl}-2-(4-methylpiperidin-1-yl)-2-oxoethyl]benzenesulfonamide
4-amino-3,5-dichloro-N-[1-{[(2-chloro-4-fluorophenyl)amino]methyl}-2-(4-methylpiperidin-1-yl)-2-oxoethyl]benzenesulfonamide
4-amino-3,5-dichloro-N-[2-(4-methylpiperidin-1-yl)-2-oxo-1-(phenoxymethyl)ethyl]benzenesulfonamide
4-amino-3,5-dichloro-N-{2-(4-methylpiperidin-1-yl)-2-oxo-1-[(pyridin-3-yloxy)methyl]ethyl}benzenesulfonamide
4-amino-3,5-dichloro-N-{1-[(2-chlorophenoxy)methyl]-2-(4-methylpiperidin-1-yl)-2-oxoethyl}benzenesulfonamide
4-amino-3,5-dichloro-N-{1-[(isoquinolin-5-yloxy)methyl]-2-(4-methylpiperidin-1-yl)-2-oxoethyl}benzenesulfonamide
N-[3-(2-chlorophenyl)-1-{[4-(hydroxymethyl)piperidin-1-yl]carbonyl}propyl]-1H-indole-4-sulfonamide
N-{3-(2-chlorophenyl)-1-[(4-methylpiperidin-1-yl)carbonyl]propyl}-3-cyano-1H-indole-4-sulfonamide
4-amino-3,5-dichloro-N-{2-(4-methylpiperidin-1-yl)-2-oxo-1-[(phenylsulfanyl)methyl]ethyl}benzenesulfonamide
3-chloro-N-{3-(2-chlorophenyl)-1-[(4-methylpiperidin-1-yl)carbonyl]propyl}-1H-indole-4-sulfonamide
N-{1-[(4-methylpiperidin-1-yl)carbonyl]-3-[2-(methylsulfonyl)phenyl]propyl}-1H-indole-4-sulfonamide
methyl 1-[2-{[(3-chloro-1H-indol-4-yl)sulfonyl]amino}-4-(2-chlorophenyl)butanoyl]piperidine-4-carboxylate In all the compounds disclosed in this application, in the event the nomenclature is in conflict with the structure, it shall be understood that the compound is defined by the structure.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-4}$alkyl that contain an oxygen atom, such as methoxy, ethoxy, propoxy, or butoxy.

The term "$C_{1-10}$-alkyl" (including those which are part of other groups) refers to branched and unbranched alkyl groups with 1 to 10 carbon atoms, by the term "$C_{1-6}$-alkyl" accordingly means branched and unbranched alkyl groups with 1 to 6 carbon atoms. "$C_{1-4}$-alkyl" accordingly denotes branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{2-6}$-alkenyl" (including those which are part of other groups) refers to branched and unbranched alkenyl groups with 2 to 6 carbon atoms and by the term "$C_{2-4}$-alkenyl" refers to branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) refers to branched and unbranched alkynyl groups with 2 to 6 carbon atoms and by the term "$C_{2-4}$-alkynyl" refers to branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1, 2- and 3-butynyl, 1-methyl-1-propynyl, 1-methyl-2-propynyl etc.

The term "cycloalkyl" shall be understood to mean an aliphatic hydrocarbon radical containing from three to twelve carbon atoms. Cycloalkyls include hydrocarbon rings containing from three to ten carbon atoms. These cycloalkyls may be either aromatic or non-aromatic ring systems. The non-aromatic ring systems may be mono- or polyunsaturated. Preferred cycloalkyls include, but are not limited, to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, and benzocycloheptenyl. Certain terms for cycloalkyl, such as cyclobutanyl and cyclobutyl, shall be used interchangeably.

The term "heterocycle" refers to a stable, nonaromatic, 4-8 membered (but preferably 5 or 6 membered) monocyclic or nonaromatic, 8-11 membered, bicyclic heterocycle radical that may be either saturated or unsaturated. Each heterocycle consists of carbon atoms and at least one, i.e., 1-4, heteroatoms chosen from, e.g., nitrogen, oxygen, or sulfur. The heterocycle may be attached by any atom of the cycle that results in the creation of a stable structure. Unless otherwise stated, heterocycles include, but are not limited to, for example, aziridinyl, azetidinyl, pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-lambda-4-thiomorpholinyl, 13-oxa-11-azatricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide, and tetramethylene sulfone.

The term "heteroaryl" shall be understood to mean an aromatic 5-8 membered monocyclic or 8-11 membered bicyclic ring containing 1-4 heteroatoms, such as N, O, and S. Unless otherwise stated, such heteroaryls include thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, and imidazo[4,5-b]pyridinyl.

In all alkyl groups or carbon chains, one or more carbon atoms can be optionally replaced by heteroatoms, such as O, S, or N. It shall be understood that, if N is not substituted, then it is NH. It shall also be understood that heteroatoms may replace either terminal carbon atoms or internal carbon atoms within a branched or unbranched carbon chain. Such groups can be substituted as herein above described by groups, such as oxo, to result in definitions, such as, but not limited to, alkoxycarbonyl, acyl, amido, and thioxo.

The term "aryl" shall be understood to mean aromatic cycloalkyl or heteroaryl as defined herein. Each aryl unless otherwise specified includes it's partially or fully hydrogenated derivative. For example, quinolinyl may include decahydroquinolinyl and tetrahydroquinolinyl, and naphthyl may include its hydrogenated derivatives, such as tetrahydranaphthyl. Other partially or fully hydrogenated derivatives of the aryl compounds described herein will be apparent to one of ordinary skill in the art.

Terms that are analogs of the above cyclic moieties, such as aryloxy or heteroaryl amine, shall be understood to mean an aryl, heteroaryl, and/or heterocycle as defined above attached to its respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used herein shall be understood to mean bromine, chlorine, fluorine or iodine. The definitions "partially or fully halogenated" and "substituted by one or more halogen atoms" include, for example, mono-, di-, or tri-halo derivatives on one or more carbon atoms. For alkyl, non-limiting examples would be —$CH_2CHF_2$, —$CF_3$, etc.

The term "ureido" means the general formula of either C(O)NR$^x$R$^y$ or NHC(O)R$^x$.

The term "carbamoyl" means the general formula C(O)NR$^x$R$^y$ or NHC(O)R$^x$.

The compounds of the invention are only those which are contemplated to be chemically stable as will be appreciated by those skilled in the art. For example, a compound that would have a dangling valency or carbanion is not a compound contemplated by the present invention.

The invention includes pharmaceutically acceptable derivatives of compounds of formula I. A "pharmaceutically acceptable derivative" refers to any pharmaceutically acceptable salt or ester, or any other compound that, upon administration to a patient, is capable of providing (directly or indirectly) a compound useful for the invention, or a pharmacologically active metabolite, or pharmacologically active residue thereof. A pharmacologically active metabolite shall be understood to mean any compound of the invention capable of being metabolized enzymatically or chemically. This includes, for example, hydroxylated or oxidized derivative compounds of the formula I.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric, and benzenesulfonic acids. Other acids, such as oxalic acid, while not themselves pharmaceutically acceptable per se, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium, and N—(C1-C4 alkyl)4+ salts.

In addition, within the scope of the invention is use of prodrugs of compounds of the formula I. Prodrugs include those compounds that, upon simple chemical transformation, are modified to produce compounds of the invention. Simple chemical transformations include hydrolysis, oxidation, and reduction. Specifically, when a prodrug is administered to a patient, the prodrug may be transformed into a compound disclosed hereinabove, thereby imparting the desired pharmacological effect.

GENERAL SYNTHETIC METHODS

The invention additionally provides for methods for making the compounds of the formula I. The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC) or mass spectrometry (MS). Intermediates and products may be purified by methods known in the art, including column chromatography, HPLC, or recrystallization.

Compounds of formula I may be prepared as illustrated in Scheme 1. Treatment of an α-amino ester II with a sulfonyl chloride bearing the desired Cy in the presence of a suitable base such as triethylamine or 1-methylmorpholine provides sulfonamide III. Hydrolysis of the ester, for example with aqueous base, followed by treatment of the resulting acid IV with a suitable coupling agent such as a dialkylcarbodimide with HOBt, or HATU with a suitable base such as i-Pr$_2$NEt and the desired amine HNR$^1$R$^2$ provides the desired compound of formula (I).

Scheme 1

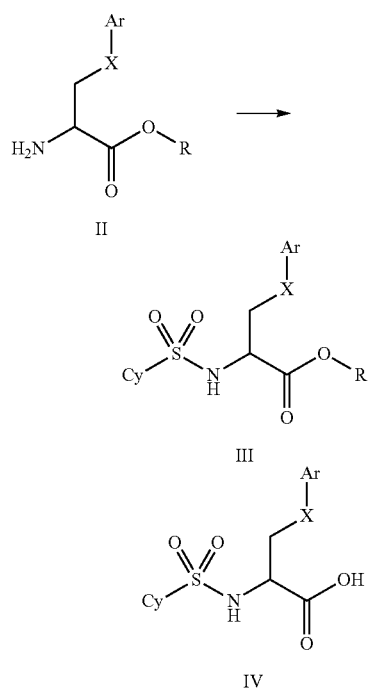

A variation of the above method is illustrated in Scheme 2. An N-carbamate protected α-amino acid V can be treated with an appropriate amine as described above to provide amide VI. This may then be followed by removal of the amine protecting group, for example with HCl or TFA if R is t-butyl, or by treating with H₂ or ammonium formate and Pd/C if R is benzyl, or by treating with piperidine if R is fluorenyl, to provide VII. Reaction of VII with the desired sulfonyl chloride and base provides the desired compound of formula (I).

Scheme 2

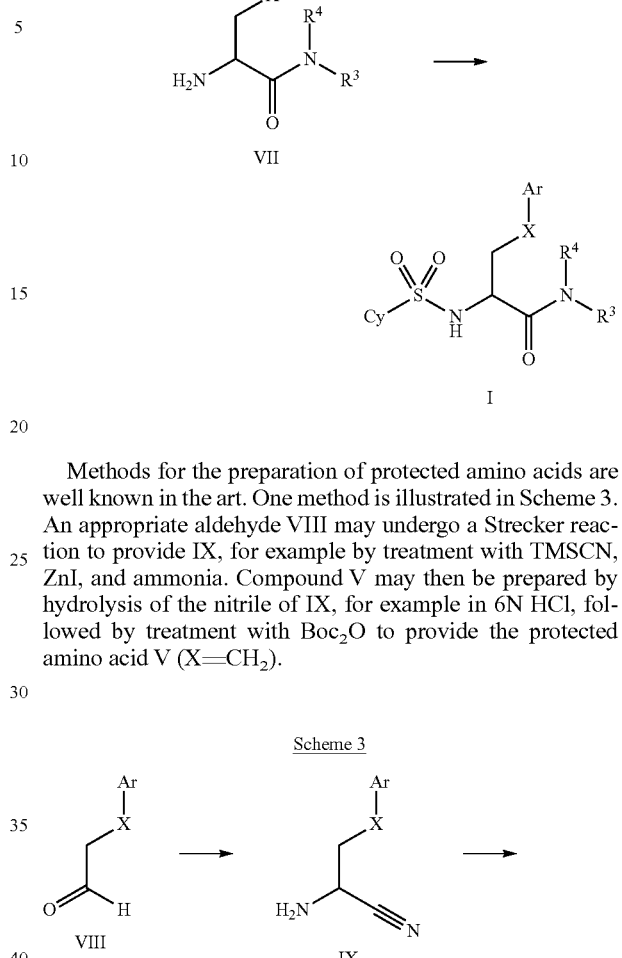

-continued

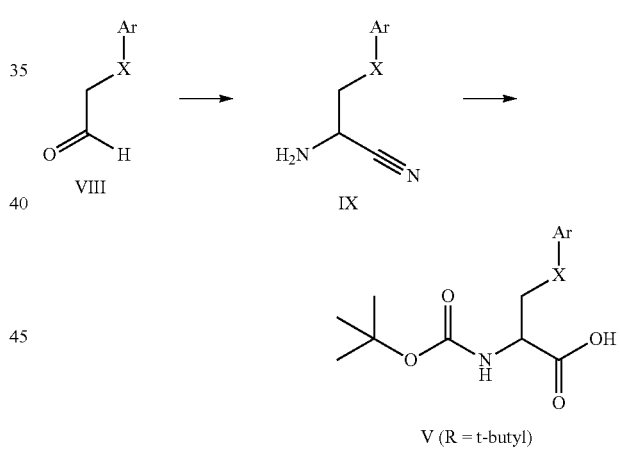

Methods for the preparation of protected amino acids are well known in the art. One method is illustrated in Scheme 3. An appropriate aldehyde VIII may undergo a Strecker reaction to provide IX, for example by treatment with TMSCN, ZnI, and ammonia. Compound V may then be prepared by hydrolysis of the nitrile of IX, for example in 6N HCl, followed by treatment with Boc₂O to provide the protected amino acid V (X=CH₂).

Scheme 3

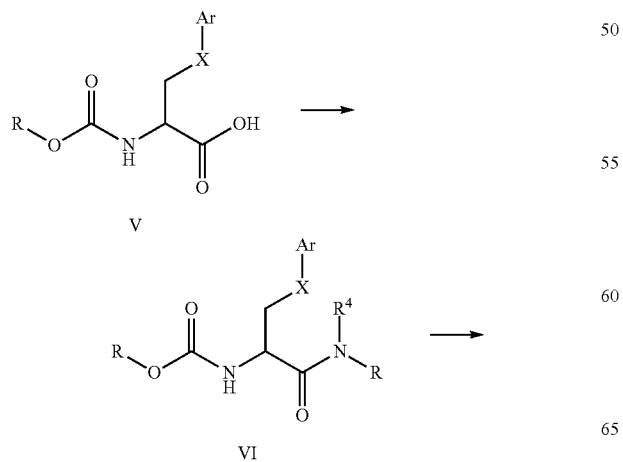

An alternative method to prepare protected amino acids is illustrated in Scheme 4.

Aminobutyrolactone X is treated with HBr in HOAc to provide the HBr salt of the bromo amino acid XI. Esterification, for example by treatment with MeOH and acetyl chloride, thionyl chloride or HCl gas, followed by protection of the amine with a suitable protecting group such as the Boc group shown provides the protected amino ester XII. A Finklestein reaction, for example with NaI in acetone provides XIII. Compound XIV may be prepared from XIII by cross-coupling with an appropriate aryl or heteroaryl iodide or bromide after the appropriate activation, for example with Zn and 1,2-dibromoethane, and in the presence of an appropriate catalyst, for example Pd(dibenzylidineacetone)₂ and (o-tolyl)₃P. Hydrolysis of the ester of XIV provides acid V, while removal of the Boc group provides amine II.

Scheme 4

Scheme 5

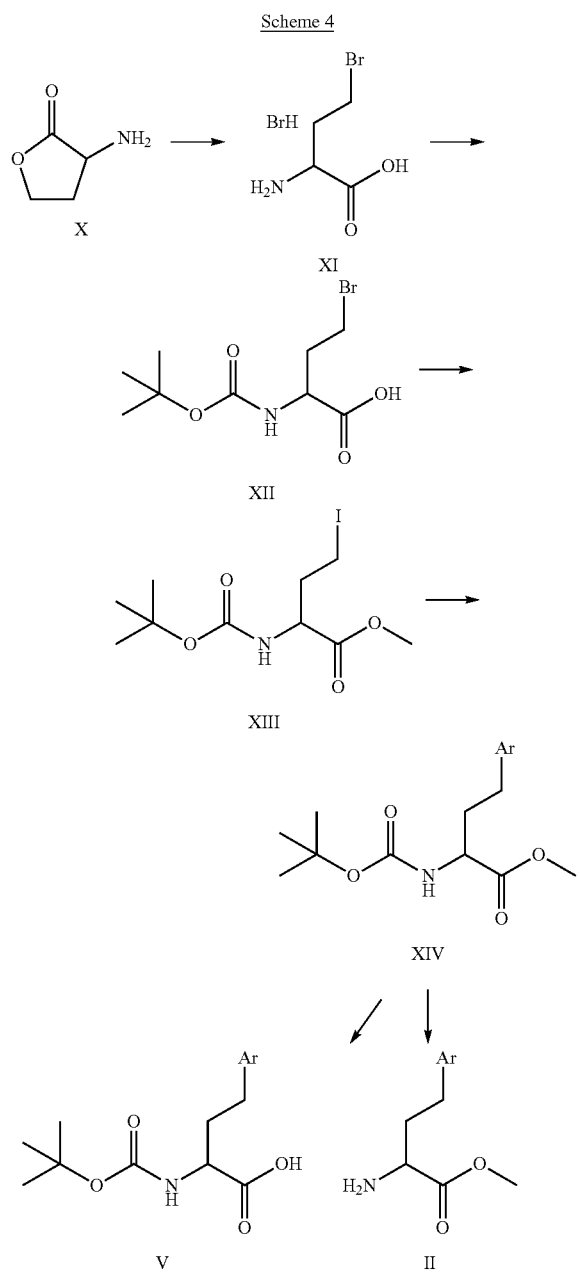

Compounds of formula (I) where X=N, O, or S may be prepared as illustrated in Scheme 5. Compound XVI may be prepared from Boc-D/L-serine XV by amide formation followed by Boc removal as described above. Treatment of XVI with one equivalent of the desired sulfonyl chloride and base will provide XVII, which may then be treated with an appropriate sulfonyl chloride, such as p-toluenesulfonyl chloride, and a strong base, such as NaH, to provide aziridine XVIII. Compounds of formula I where X=NH may be prepared by treatment of XVIII with the appropriate aniline or aminoheteroaryl compound and β-cyclodextrin. Compounds of formula (I) where X=O may also be prepared by treating XVIII with the appropriate phenol of hydroxyheteroaryl compound and a base, such as lithium hexamethyldisilazide. Compounds of formula I where X=S may also be prepared by treating XVIII with the appropriate thiol.

The $CySO_2Cl$ intermediates used in the above schemes may be purchased or prepared by methods known in the art, for example by treatment of Cy with chlorosulfonic acid, by treatment of CyBr with t-BuLi followed by $SO_2$ and N-chlorosuccinimide or $SO_2Cl_2$, or by treatment of $CyNH_2$ with $NaNO_2$ followed by CuCl or $CuCl_2$ and SO2 or $SO_3H_2$ in acetic acid.

Abbreviations:
  Boc tert-butyloxycarbonyl
  dba dibenzylideneacetone
  DCE dichloroethane
  DMAP 4-(dimethylamino)pyridine
  DMA dimethylacetamide
  DMF dimethylformamide
  dppf 1,1'-bisdiphenylphosphinoferrocene
  EDC 1-(3-dimethylaminopropyl)-3-ethylcarbodiimide hydrochloride
  HATU O-(-7-azabenzotriazol-1-yl)-N,N,N',N'-tetramethyluronium hexafluorophosphate
  HOBt 1-hydroxybenzotriazole
  MeCN acetonitrile
  MP—macroporous polystyrene support
  NBS N-bromosuccinimide
  NCS N-chlorosuccinimide
  NMM N-methyl morpholine
  PS—gel-form polystyrene support
  rt room temperature TFA trifluoroacetic acid
TMS trimethylsilyl

Example 1

2-chloro-N-{1-[(4-methylpiperidin-1-yl)carbonyl]-3-phenylpropyl}benzenesulfonamide

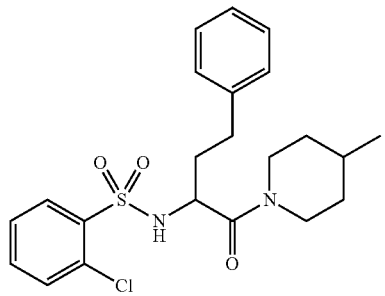 [SMILES: CC1CCN(C(=O)C(CCc2ccccc2)NS(=O)(=O)c2ccccc2Cl)CC1]

A solution of 6.7 g (31 mmol) of Boc$_2$O in 75 mL of THF is added to 5.0 g (28 mmol) of (D/L)-homophenylalanine and 3.0 g (28 mmol) of Na$_2$CO$_3$ in 100 mL of water and 15 mL of THF. After stirring overnight, the solution is diluted with water and extracted with CH$_2$Cl$_2$. The aqueous layer is acidified with 1M KHSO$_4$ and extracted with CH$_2$Cl$_2$ (3×). The combined extracts are dried over MgSO$_4$, filtered, and evaporated to provide 7.0 g (90%) of Boc-(D/L)-homophenylalanine. To this material in 150 mL of DMF are added 3.0 mL (30 mmol) of 4-methylpiperidine, 5.0 mL (29 mmol) of iPr$_2$NEt, 5.0 g (37 mmol) of HOBt, and 5.5 g (35 mmol) of EDC. After stirring overnight, the mixture is poured into water and extracted with EtOAc. The extract is washed with water and brine, dried over MgSO$_4$, filtered, and concentrated. The residue is washed with hexanes to provide 6.0 g of the 4-methylpiperidinyl amide, that is dissolved in 40 mL CH$_2$Cl$_2$ and 5.0 mL of 4 M HCl in 1,4-dioxane. After stirring for 2 hours, the mixture is concentrated and treated with hexane to form a white solid. Recrystallization from MeOH/hexane provides 3.6 g of 1-(4-methylpiperidin-1-yl)-1-oxo-4-phenylbutan-2-amine.

A mixture of 29 mg (0.11 mmol) of 1-(4-methylpiperidin-1-yl)-1-oxo-4-phenylbutan-2-amine, 2-chlorobenzenesulfonyl chloride, and 0.19 mL (0.11 mmol) of iPr$_2$NEt in 4 mL of CH$_2$Cl$_2$ is stirred for 16 h, concentrated, and purified by preparative HPLC to provide Example 1

ESI MS Calc. 434.1; Found: 435.2 (M+H)$^+$.

Examples 2-4 are prepared from Boc-(D/L)-homophenylalanine, the appropriate amines, and sulfonyl chlorides in the same manner that Example 1 is synthesized.

Example 2

2,4,6-trimethyl-N-{1-[(4-methylpiperidin-1-yl)carbonyl]-3-phenylpropyl}benzenesulfonamide from 4-methylpiperidine and 2,4,6-trimethyl-benzenesulfonyl chloride.

Example 3

N-{1-[(4-methylpiperidin-1-yl)carbonyl]-3-phenylpropyl}naphthalene-1-sulfonamide from 4-methylpiperidine and 1-napthalenesulfonyl chloride. ESI MS Calc. 450.2; Found: 451.3 (M+H)$^+$.

Example 4

4-amino-3,5-dichloro-N-[1-(3,4-dihydroisoquinolin-2(1H)-ylcarbonyl)-3-phenylpropyl]benzenesulfonamide from 1,2,3,4-tetrahydroisoquinoline and 4-amino-2,6-dichlorobenzenesulfonyl chloride. ESI MS Calc. 517.1; Found: 518.2 (M+H)$^+$.

Example 5

N-{3-(2-chlorophenyl)-1-[(4-methylpiperidin-1-yl)carbonyl]propyl}benzenesulfonamide

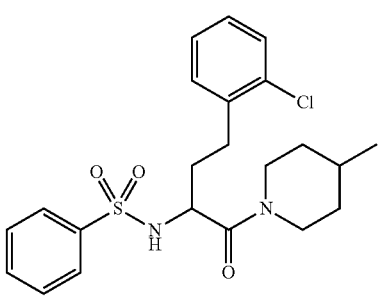 [SMILES: CC1CCN(C(=O)C(CCc2ccccc2Cl)NS(=O)(=O)c2ccccc2)CC1]

A mixture of 2.2 mL (18 mmol) of 2-chloroiodobenzene, 1.8 mL (27 mmol) of allyl alcohol, 81 mg (0.36 mmol) of Pd(OAc)$_2$, 5.3 g (18 mmol) of Bu$_4$NCl, and 3.8 g (45 mmol) of NaHCO$_3$ in 50 mL of DMF is stirred under Ar$_2$ at 30° C. for 24 h. Water is added and the mixture is extracted with EtOAc. The extract is washed with brine, dried over MgSO$_4$, filtered and concentrated. Flash chromatography (0-50% EtOAc in hexanes) provides 2.2 g (74%) of 3-(2-chlorophenyl)propenal.

To a mixture of 2.2 g (13 mmol) of 3-(2-chlorophenyl)propenal and 2.6 mL (20 mmol) of TMSCN in 3 mL of Et$_2$O in a pressure tube is added ~1 mg of ZnI$_2$. After stirring for 15 min, 10 mL of 7 M NH$_3$ in MeOH is added. The pressure tube is sealed and heated to 50° C. for 5 h. The mixture is concentrated to provide 2.5 g (98%) of unpurified cyanohydrin. This material is heated to 100° C. in 10 mL of concentrated HCl for 12 h. The mixture is cooled and filtered, and then dissolved in 50 mL of dioxane. Saturated NaHCO$_3$ (50 mL) is slowly added, followed by 8.4 g (39 mmol) of Boc$_2$O. After stirring for 2 h, the mixture is extracted with EtOAc. The aqueous solution is acidified to pH 4 with 1 N HCl, and then extracted with EtOAc. The extract is washed with brine, dried over MgSO$_4$, filtered, and concentrated to provide 2.2 g (55%) of 2-[(tert-butoxycarbonyl)amino]-4-(2-chlorophenyl)butanoic acid.

A mixture of 1.7 g (5.4 mmol) of 2-[(tert-butoxycarbonyl)amino]-4-(2-chlorophenyl)butanoic acid, 2.1 g (11 mmol) of EDC, 1.5 g (11 mmol) HOBt, and 1.9 mL (11 mmol) of iPrNEt in 25 mL of CH$_2$Cl$_2$ is stirred for 10 min, and 0.77 mL (6.5 mmol) of 4-methylpiperidine is added. After stirring overnight, the mixture is washed twice with 10% citric acid, and once each with water, saturated NaHCO$_3$, water, and brine. The extract is concentrated to provide 1.8 g (85%) of tert-butyl{3-(2-chlorophenyl)-1-[(4-methylpiperidin-1-yl)carbonyl]propyl}carbamate.

A solution of 1.8 g (4.6 mmol) of tert-butyl{3-(2-chlorophenyl)-1-[(4-methylpiperidin-1-yl)carbonyl]propyl}carbamate in 4.6 mL (18 mmol) of 4 M HCl in 1,4-dioxane is stirred for 2 h, and then concentrated. The residue is stirred in Et$_2$O overnight, and then filtered and washed with Et$_2$O to provide 0.90 g (60%) of 4-(2-chlorophenyl)-1-(4-methyl piperidin-1-yl)-1-oxobutan-2-amine hydrochloride.

A mixture of 0.095 mmol of 4-(2-chlorophenyl)-1-(4-methylpiperidin-1-yl)-1-oxobutan-2-amine hydrochloride, 0.4 mL of 4-methylmorpholine, and 0.1 mmol of benzensulfonyl chloride in 0.55 mL of DCE is shaken overnight and then concentrated and purified directly by preparative HPLC to provide 9.5 mg (21%) of Example 5. ESI MS Calc. 434.1; Found: 435.1 (M+H)$^+$.

Examples 6-38 are prepared from 4-(2-chlorophenyl)-1-(4-methylpiperidin-1-yl)-1-oxobutan-2-amine hydrochloride and the appropriate sulfonyl chloride in a manner similar to the synthesis of Example 5.

Example 6

N-{3-(2-chlorophenyl)-1-[(4-methylpiperidin-1-yl)carbonyl]propyl}-2-methyl-benzenesulfonamide from 2-methylbenzensulfonyl chloride. ESI MS Calc. 448.2; Found: 449.1 (M+H)$^+$.

Example 7

N-{3-(2-chlorophenyl)-1-[(4-methylpiperidin-1-yl)carbonyl]propyl}-3-methyl-benzenesulfonamide from 3-methylbenzenesulfonyl chloride. ESI MS Calc. 448.2; Found: 449.2 (M+H)$^+$.

Example 8

N-{3-(2-chlorophenyl)-1-[(4-methylpiperidin-1-yl)carbonyl]propyl}-2-cyanobenzenesulfonamide from 2-cyanobenzenesulfonyl chloride. ESI MS Calc. 459.1; Found: 460.1 (M+H)$^+$.

Example 9

N-{3-(2-chlorophenyl)-1-[(4-methylpiperidin-1-yl)carbonyl]propyl}-3-cyanobenzenesulfonamide from 3-cyanobenzenesulfonyl chloride. ESI MS Calc. 459.1; Found: 460.1 (M+H)$^+$.

Example 10

N-{3-(2-chlorophenyl)-1-[(4-methylpiperidin-1-yl)carbonyl]propyl}-2,4-dimethylbenzenesulfonamide from 2,4-dimethylbenzenesulfonyl chloride. ESI MS Calc. 462.2; Found: 463.1 (M+H)$^+$.

Example 11

N-{3-(2-chlorophenyl)-1-[(4-methylpiperidin-1-yl)carbonyl]propyl}-2,5-dimethylbenzenesulfonamide from 2,5-dimethylbenzenesulfonyl chloride. ESI MS Calc. 462.2; Found: 463.1 (M+H)$^+$.

Example 12

N-{3-(2-chlorophenyl)-1-[(4-methylpiperidin-1-yl)carbonyl]propyl}-3,5-dimethylbenzenesulfonamide from 3,5-dimethylbenzenesulfonyl chloride. ESI MS Calc. 462.2; Found: 463.2 (M+H)$^+$.

Example 13

N-{3-(2-chlorophenyl)-1-[(4-methylpiperidin-1-yl)carbonyl]propyl}-2-methoxybenzenesulfonamide from 2-methoxybenzenesulfonyl chloride. ESI MS Calc. 464.2; Found: 465.2 (M+H)$^+$.

Example 14

N-{3-(2-chlorophenyl)-1-[(4-methylpiperidin-1-yl)carbonyl]propyl}-3-methoxybenzenesulfonamide from 3-methoxybenzenesulfonyl chloride. ESI MS Calc. 464.2; Found: 465.2 (M+H)$^+$.

Example 15

N-{3-(2-chlorophenyl)-1-[(4-methylpiperidin-1-yl)carbonyl]propyl}-4-methoxybenzenesulfonamide from 4-methoxybenzenesulfonyl chloride. ESI MS Calc. 464.2; Found: 465.2 (M+H)$^+$.

Example 16

N-{3-(2-chlorophenyl)-1-[(4-methylpiperidin-1-yl)carbonyl]propyl}-4-fluoro-2-methylbenzenesulfonamide from 2-methyl-4-fluorobenzenesulfonyl chloride. ESI MS Calc. 466.2; Found: 467.2 (M+H)$^+$.

Example 17

2-chloro-N-{3-(2-chlorophenyl)-1-[(4-methylpiperidin-1-yl)carbonyl]propyl}benzenesulfonamide from 2-chlorobenzenesulfonyl chloride. ESI MS Calc. 468.1; Found: 469.2 (M+H)$^+$.

Example 18

3-chloro-N-{3-(2-chlorophenyl)-1-[(4-methylpiperidin-1-yl)carbonyl]propyl}benzenesulfonamide from 3-chlorobenzenesulfonyl chloride. ESI MS Calc. 468.1; Found: 469.1 (M+H)$^+$.

Example 19

4-chloro-N-{3-(2-chlorophenyl)-1-[(4-methylpiperidin-1-yl)carbonyl]propyl}benzenesulfonamide from 4-chlorobenzenesulfonyl chloride. ESI MS Calc. 468.1; Found: 469.1 (M+H)$^+$.

Example 20

2-chloro-N-{3-(2-chlorophenyl)-1-[(4-methylpiperidin-1-yl)carbonyl]propyl}pyridine-3-sulfonamide from 2-chloropyridine-3-sulfonyl chloride. ESI MS Calc. 469.1; Found: 470.1 (M+H)$^+$.

Example 21

N-{3-(2-chlorophenyl)-1-[(4-methylpiperidin-1-yl)carbonyl]propyl}-1H-indole-3-sulfonamide from N-triisopropylsilylindole-3-sulfonyl chloride with subsequent treatment with TBAF. ESI MS Calc. 473.2; Found: 474.3 (M+H)$^+$.

Example 22

N-{3-(2-chlorophenyl)-1-[(4-methylpiperidin-1-yl)carbonyl]propyl}-1H-indole-4-sulfonamide from indole-4-sulfonyl chloride. ESI MS Calc. 473.2; Found: 474.4 (M+H)+.

Example 23

N-{3-(2-chlorophenyl)-1-[(4-methylpiperidin-1-yl)carbonyl]propyl}-1H-indole-6-sulfonamide from indole-6-sulfonyl chloride. ESI MS Calc. 473.2; Found: 474.2 (M+H)+.

Example 24

N-{3-(2-chlorophenyl)-1-[(4-methylpiperidin-1-yl)carbonyl]propyl}-2-methoxy-5-methylbenzenesulfonamide from 2-methoxyl-5-methyl-benzenesulfonyl chloride. ESI MS Calc. 478.2; Found: 479.2 (M+H)+.

Example 25

3-chloro-N-{3-(2-chlorophenyl)-1-[(4-methylpiperidin-1-yl)carbonyl]propyl}-2-methylbenzenesulfonamide from 2-methyl-3-chlorobenzenesulfonyl chloride. ESI MS Calc. 482.1; Found: 483.1 (M+H)+.

Example 26

5-chloro-N-{3-(2-chlorophenyl)-1-[(4-methylpiperidin-1-yl)carbonyl]propyl}-1,3-dimethyl-1H-pyrazole-4-sulfonamide from 1,3-dimethyl-5-chloro-1H-pyrazole-4-sulfonyl chloride. ESI MS Calc. 486.1; Found: 487.1 (M+H)+.

Example 27

N-{3-(2-chlorophenyl)-1-[(4-methylpiperidin-1-yl)carbonyl]propyl}-1-methyl-1H-indole-4-sulfonamide from 1-methylindole-4-sulfonyl chloride. ESI MS Calc. 487.2; Found: 488.2 (M+H)+.

Example 28

N-{3-(2-chlorophenyl)-1-[(4-methylpiperidin-1-yl)carbonyl]propyl}-2-oxo-2,3-dihydro-1H-indole-5-sulfonamide from 2-oxo-2,3-dihydro-1H-indole-5-sulfonyl chloride. ESI MS Calc. 487.2; Found: 490.2 (M+H)+.

Example 29

N-{3-(2-chlorophenyl)-1-[(4-methylpiperidin-1-yl)carbonyl]propyl}-1-benzothiophene-3-sulfonamide from benzothiophene-3-sulfonyl chloride. ESI MS Calc. 490.1; Found: 474.2 (M+H)+.

Example 30

N-[3-({3-(2-chlorophenyl)-1-[(4-methylpiperidin-1-yl)carbonyl]propyl}sulfamoyl)phenyl]acetamide from 3-acetamidobenzenesulfonyl chloride. ESI MS Calc. 491.1; Found: 492.2 (M+H)+.

Example 31

4-(carbamoylamino)-N-{3-(2-chlorophenyl)-1-[(4-methylpiperidin-1-yl)carbonyl]propyl}benzenesulfonamide from 4-uriedobenzenesulfonyl chloride. ESI MS Calc. 492.2; Found: 493.2 (M+H)+.

Example 32

N-[4-({3-(2-chlorophenyl)-1-[(4-methylpiperidin-1-yl)carbonyl]propyl}sulfamoyl)-3-methylphenyl]acetamide from 2-methyl-4-acetamido-benzenesulfonyl chloride. ESI MS Calc. 505.2; Found: 506.2 (M+H)+.

Example 33

N-{3-(2-chlorophenyl)-1-[(4-methylpiperidin-1-yl)carbonyl]propyl}-1-methyl-3-(trifluoromethyl)-1H-pyrazole-4-sulfonamide from 1-methyl-3-trifluoromethyl-1H-pyrazole-4-sulfonyl chloride. ESI MS Calc. 506.1; Found: 507.1 (M+H)+.

Example 34

6-chloro-N-{3-(2-chlorophenyl)-1-[(4-methylpiperidin-1-yl)carbonyl]propyl}imidazo[2,1-b][1,3]thiazole-5-sulfonamide from 6-chloro-imidazol[2,1-b][1,3]thiazole-5-sulfonyl chloride. ESI MS Calc. 514.1; Found: 515.0 (M+H)+.

Example 35

N-{3-(2-chlorophenyl)-1-[(4-methylpiperidin-1-yl)carbonyl]propyl}-5-methyl-1-phenyl-1H-pyrazole-4-sulfonamide from 1-phenyl-5-methyl-1H-pyrazole-4-sulfonyl chloride. ESI MS Calc. 514.2; Found: 515.2 (M+H)+.

Example 36

4-amino-3,5-dichloro-N-{3-(2-chlorophenyl)-1-[(4-methylpiperidin-1-yl)carbonyl]propyl}benzenesulfonamide from 4-amino-3,5-dichlorobenzenesulfonyl chloride. ESI MS Calc. 517.1; Found: 518.2 (M+H)+.

Example 37

N-{3-(2-chlorophenyl)-1-[(4-methylpiperidin-1-yl)carbonyl]propyl}-3-(2-methylpyrimidin-4-yl)benzenesulfonamide from 3-(2-methylpyrimidin-4-yl)benzenesulfonyl chloride. ESI MS Calc. 526.2; Found: 527.2 (M+H)+.

Example 38

5-bromo-N-{3-(2-chlorophenyl)-1-[(4-methylpiperidin-1-yl)carbonyl]propyl}-2,3-dihydro-1-benzofuran-7-sulfonamide from 5-bromo-2,3-dihydro-1-benzofuran-7-sulfonyl chloride. ESI MS Calc. 554.1; Found: 555.1 (M+H)+.

Example 39

(2R)—N-benzyl-N-methyl-2-{[(2-methylphenyl)sulfonyl]amino}-4-phenylbutanamide

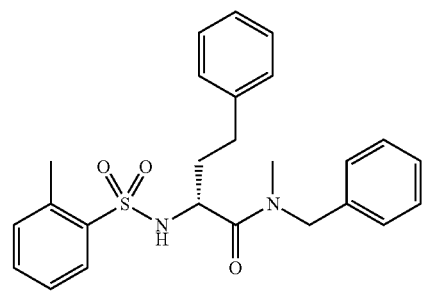 [SMILES: Cc1ccccc1S(=O)(=O)N[C@H](CCc1ccccc1)C(=O)N(C)Cc1ccccc1]

tert-Butyl{(1R)-1-[benzyl(methyl)carbamoyl]-3-phenylpropyl}carbamate is prepared from Boc-(D)-homophenylalanine and N-methylbenzylamine in the same manner that tert-butyl{3-(2-chlorophenyl)-1-[(4-methylpiperidin-1-yl)carbonyl]propyl}carbamate is synthesized.

A 0.18 M solution of tert-butyl{(1R)-1-[benzyl(methyl)carbamoyl]-3-phenylpropyl}carbamate (0.5 mL, 0.09 mmol) in DCE is treated with 0.11 mL of 4 M HCl in 1,4-dioxane and shaken overnight. The mixture is concentrated and treated with 0.5 mL of DCE, 0.05 mL of Et$_3$N, and 0.5 mL of a 0.22 M solution of 2-methylbenzenesulfonyl chloride (0.11 mmol). After shaking for 2 h, the mixture is concentrated, and purified by preparative HPLC to provide 13 mg (33%) of Example 39. ESI MS Calc.436.2; Found: 437.2 (M+H)$^+$.

Examples 40-48 are prepared from Boc-(D)-homophenylalanine, the appropriate amine, and the appropriate sulfonyl chloride in a manner similar to the synthesis of Example 39.

Example 40

N-[(1R)-1-(3,4-dihydroisoquinolin-2(1H)-ylcarbonyl)-3-phenylpropyl]-2-methylbenzenesulfonamide from 1,2,3,4-tetrahydroisoquinoline and 2-methylbenzenesulfonyl chloride. ESI MS Calc. 448.2; Found: 449.3 (M+H)$^+$.

Example 41

2-methyl-N-{(1R)-1-[(trans)-octahydroisoquinolin-2(1H)-ylcarbonyl]-3-phenylpropyl}benzenesulfonamide from trans-decahydroisoquinoline and 2-methylbenzenesulfonyl chloride. ESI MS Calc. 454.2; Found: 455.3 (M+H)$^+$.

Example 42

2-amino-4,6-dichloro-N-{(1R)-1-[(4-methylpiperidin-1-yl)carbonyl]-3-phenylpropyl}benzenesulfonamide from 4-methylpiperidine and 2-amino-4,6-dichlorobenzenesulfonyl chloride. ESI MS Calc. 483.1; Found: 484.1 (M+H)$^+$.

Example 43

2,6-dichloro-N-[(1R)-1-(3,4-dihydroisoquinolin-2(1H)-ylcarbonyl)-3-phenylpropyl]benzenesulfonamide 1,2,3,4-tetrahydroisoquinoline and 2,6-dichlorobenzenesulfonyl chloride. ESI MS Calc. 502.1; Found: 503.1 (M+H)$^+$.

Example 44

(2R)-2-{[(4-amino-3,5-dichlorophenyl)sulfonyl]amino}-N-benzyl-N-methyl-4-phenylbutanamide N-methylbenzylamine and 4-amino-2,5-dichloro-benzenesulfonyl chloride. ESI MS Calc. 505.1; Found: 506.1 (M+H)$^+$.

Example 45

2-amino-4,6-dichloro-N-[(1R)-1-(3,4-dihydroisoquinolin-2(1H)-ylcarbonyl)-3-phenylpropyl]benzenesulfonamide 1,2,3,4-tetrahydroisoquinoline and 2-amino-4,6-dichlorobenzenesulfonyl chloride. ESI MS Calc. 517.1; Found: 518.2 (M+H)$^+$.

Example 46

2,6-dichloro-N-[(1R)-3-phenyl-1-{[4-(trifluoromethyl)piperidin-1-yl]carbonyl}propyl]benzenesulfonamide from 4-trifluoromethylpiperidine and 2,6-dichlorobenzenesulfonyl chloride. ESI MS Calc. 522.1; Found: 523.1 (M+H)$^+$.

Example 47

4-amino-3,5-dichloro-N-[(1R)-3-phenyl-1-{[4-(trifluoromethyl)piperidin-1-yl]carbonyl}propyl]benzenesulfonamide from 4-trifluoromethylpiperidine and 4-amino-3,5-dichlorobenzenesulfonyl chloride. ESI MS Calc. 537.1; Found: 538.1 (M+H)$^+$.

Example 48

2,6-dichloro-N-{1-[(4-methylpiperidin-1-yl)carbonyl]-3-phenylpropyl}benzenesulfonamide from 2,6-dichlorobenzenesulfonyl chloride. ESI MS Calc. 468.1; Found: 469.1 (M+H)$^+$.

Example 49

N-{(1R)-1-[(4-methylpiperidin-1-yl)carbonyl]-3-phenylpropyl}-1H-indole-4-sulfonamide

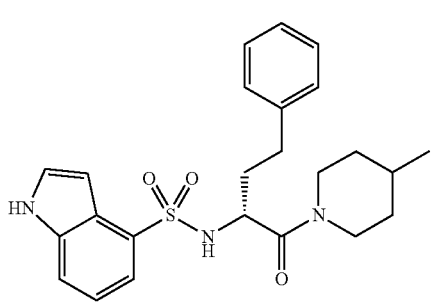 [SMILES: CC1CCN(C(=O)[C@@H](CCc2ccccc2)NS(=O)(=O)c2cccc3[nH]ccc23)CC1]

tert-Butyl{(1R)-1-[benzyl(methyl)carbamoyl]-3-phenylpropyl}carbamate (275 mg, 0.76 mmol) is stirred in 2.3 mL of CH$_2$Cl$_2$ and 0.76 mL (3.1 mmol) of TFA for 12 h. The mixture is concentrated, dissolved in 1,4-dioxane, and concentrated again to provide 226 mg (90%) of the amine trifluoroacetate (2R)-2-amino-N-benzyl-N-methyl-4-phenylbutanamide.

To a solution of 2.0 mL (16 mmol) of 4-bromoindole in 20 mL of THF and 20 mL of Et$_2$O at 0° C. is added 660 mg (17 mmol) of 60% NaH in mineral oil. After stirring for 15 min, the mixture is cooled to −78° C., and 19 mL (32 mmol) of 1.7 M t-BuLi in pentane is added slowly. After 30 min, 11 mL (32 mmol) of a 19% solution of SO$_2$ in THF is slowly added. The mixture is then allowed to warm to rt overnight. To the resulting solid is added 30 mL of Et$_2$O and 0.91 mL (16 mmol) of glacial acetic acid. The mixture is stirred for 30 min at 0° C., and then is filtered and quickly washed with Et$_2$O. The solids are then suspended in 30 mL of Et$_2$O, chilled to 0° C., and 2.2 g (16 mmol) of NCS is carefully added. The resulting suspension is stirred rapidly for 30 min, and then is filtered and washed with Et$_2$O. The filtrate and washes are concentrated to provide 1.9 g (55%) of indol-4-yl sulfonyl chloride as a brown oil that solidifies upon freezing.

A mixture of 29 mg (0.098 mmol) of (2R)-2-amino-N-benzyl-N-methyl-4-phenylbutanamide, 25 mg (0.12 mmol) of indol-4-yl sulfonyl chloride, 0.033 mL (0.30 mmol) of 4-methylmorpholine in 0.4 mL of MeCN is stirred overnight, and then purified directly to provide 8.1 mg (18%) of Example 49. ESI MS Calc. 439.2; Found: 440.4 (M+H)$^+$.

Example 50

N-{(1R)-1-[(4-methylpiperidin-1-yl)carbonyl]-3-phenylpropyl}-1H-indole-6-sulfonamide

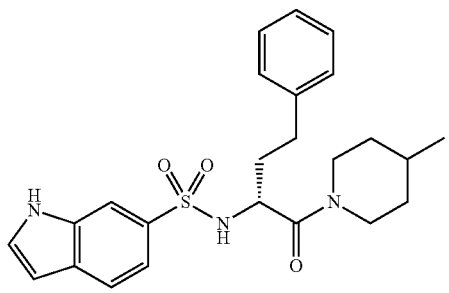 [SMILES: CC1CCN(C(=O)[C@@H](CCc2ccccc2)NS(=O)(=O)c2ccc3cc[nH]c3c2)CC1]

To a solution of 2.4 g (12 mmol) of 6-bromoindole in 20 mL of THF and 20 mL of Et$_2$O at 0° C. is added 500 mg (12 mmol) of 60% NaH in mineral oil. After stirring for 15 min, the mixture is cooled to −78° C., and 14 mL (24 mmol) of 1.7 M t-BuLi in pentane is added slowly. After 30 min, 8.0 mL (24 mmol) of a 19% solution of SO$_2$ in THF is slowly added. The mixture is then allowed to warm to rt overnight. To the resulting solid is added 30 mL of Et$_2$O and 0.76 mL (13 mmol) of glacial acetic acid. The mixture is stirred for 30 min at 0° C., and then is filtered and quickly washed with Et$_2$O. The solids are then suspended in 30 mL of Et$_2$O, chilled to 0° C., and 1.7 g (12 mmol) of NCS is carefully added. The resulting suspension is stirred rapidly for 30 min, and then is filtered and washed with Et$_2$O. The filtrate and washes are concentrated to provide 1.8 g (70%) of indol-6-yl sulfonyl chloride as a brown crystalline solid.

Example 50 is prepared from (2R)-2-amino-N-benzyl-N-methyl-4-phenylbutanamide (28 mg, 0.098 mmol) and indol-6-yl sulfonyl chloride in the same manner as Example 49 (26 mg, 62% yield). ESI MS Calc. 439.2; Found: 440.5 (M+H)$^+$.

Example 51

N-{1-[(4-methylpiperidin-1-yl)carbonyl]-3-pyridin-2-ylpropyl}-1H-indole-4-sulfonamide

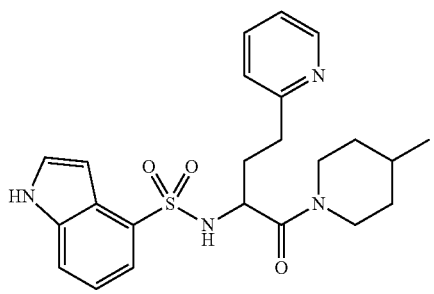

tert-Butyl{1-[(4-methylpiperidin-1-yl)carbonyl]-3-pyridin-2-ylpropyl}carbamate is prepared from pyridin-2-yl propionaldehyde (Kitbunnadaj, R. et al. *J. Med. Chem*, 2004, 47, 2414-2417) in the same manner that tert-butyl{3-(2-chlorophenyl)-1-[(4-methylpiperidin-1-yl)carbonyl]propyl}carbamate is prepared from 3-(2-chlorophenyl)propenal in Example 5.

Example 51 is prepared from 70 mg (0.19 mmol) of tert-butyl{1-[(4-methylpiperidin-1-ylcarbonyl]-3-pyridin-2-ylpropyl}carbamate and indole-4-sulfonyl chloride in the same manner as Example 49 (39 mg, 46% yield). ESI MS Calc. 440.2; Found: 441.3 (M+H)$^+$.

Example 52

N-{1-[(4-methylpiperidin-1-yl)carbonyl]-3-pyridin-3-ylpropyl}-1H-indole-4-sulfonamide

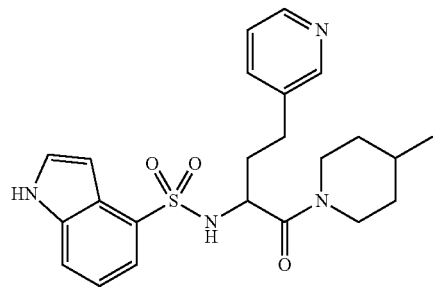 [SMILES: CC1CCN(C(=O)C(CCc2cccnc2)NS(=O)(=O)c2cccc3[nH]ccc23)CC1]

tert-Butyl{1-[(4-methylpiperidin-1-yl)carbonyl]-3-pyridin-3-ylpropyl}carbamate is prepared from pyridin-3-yl propionaldehyde (Kitbunnadaj, R. et al. *J. Med. Chem*, 2004, 47, 2414-2417) in the same manner that tert-butyl{3-(2-chlorophenyl)-1-[(4-methylpiperidin-1-yl)carbonyl]propyl}carbamate is prepared from 3-(2-chlorophenyl)propenal in Example 5.

Example 52 is prepared from 70 mg (0.19 mmol) of tert-butyl{1-[(4-methylpiperidin-1-yl)carbonyl]-3-pyridin-3-ylpropyl}carbamate and indole-4-sulfonyl chloride in the same manner as Example 49 (39 mg, 46% yield). ESI MS Calc. 440.2; Found: 441.3 (M+H)$^+$.

Example 53

N-{1-[(4-methylpiperidin-1-yl)carbonyl]-3-pyridin-4-ylpropyl}-1H-indole-4-sulfonamide

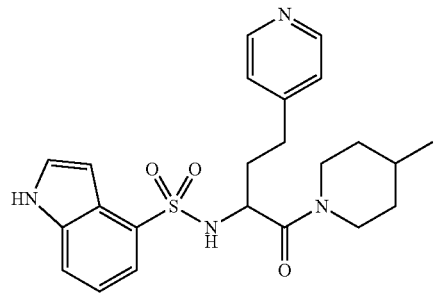 [SMILES: CC1CCN(C(=O)C(CCc2ccncc2)NS(=O)(=O)c2cccc3[nH]ccc23)CC1]

tert-Butyl{1-[(4-methylpiperidin-1-yl)carbonyl]-3-pyridin-4-ylpropyl}carbamate is prepared from pyridin-4-yl propionaldehyde (Kitbunnadaj, R. et al. *J. Med. Chem*, 2004, 47, 2414-2417) in the same manner that tert-butyl{3-(2-chlorophenyl)-1-[(4-methylpiperidin-1-yl)carbonyl]propyl}carbamate is prepared from 3-(2-chlorophenyl)propenal in Example 5.

Example 53 is prepared from 70 mg (0.19 mmol) of tert-butyl{1-[(4-methylpiperidin-1-yl)carbonyl]-3-pyridin-4-

Example 54

2-chloro-6-methyl-N-{1-[(4-methylpiperidin-1-yl)carbonyl]-3-phenylpropyl}benzenesulfonamide

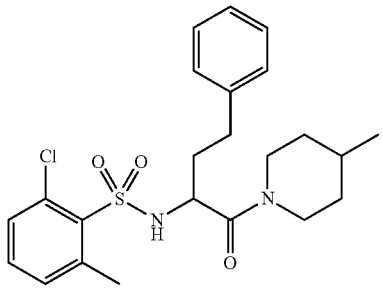 [SMILES: Cc1cccc(Cl)c1S(=O)(=O)NC(CCc1ccccc1)C(=O)N1CCC(C)CC1]

A mixture of 20 mg (0.077 mmol) of 1-(4-methylpiperidin-1-yl)-1-oxo-4-phenylbutan-2-amine, 0.11 mmol of 2-chloro-6-methylbenzene-sulfonyl chloride, and 0.2 mmol of $Et_3N$ in 1 mL of DCE is stirred for 16 h, and 240 mg of MP-carbonate and 170 mg of PS-trisamine are added. The mixture is shaken for 2 days, filtered, and concentrated to provide Example 54.

Example 55

N-[3-(2-chlorophenyl)-1-(piperidin-1-ylcarbonyl)propyl]-1H-indole-4-sulfonamide

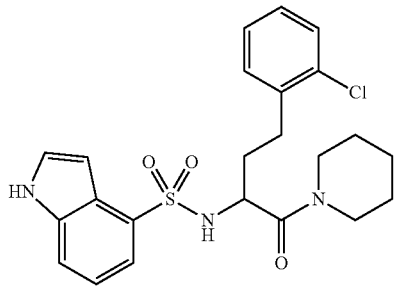 [SMILES: O=C(C(CCc1ccccc1Cl)NS(=O)(=O)c1cccc2[nH]ccc12)N1CCCCC1]

A mixture of 1.4 g (4.5 mmol) of 2-[(tert-butoxycarbonyl)amino]-4-(2-chlorophenyl)butanoic acid, 1.0 g (5.4 mmol) of EDC, 0.72 g (5.4 mmol) of HOBt, and ~5 mg of DMAP in 10 mL of $CH_2Cl_2$ is stirred for 5 minutes before 0.17 g (5.4 mmol) of methanol is added. After stirring for 3 h, the mixture is concentrated and purified by flash chromatography (0-100% EtOAc in hexanes) to provide 1.1 g (77%) of the methyl ester methyl 2-[(tert-butoxycarbonyl)amino]-4-(2-chlorophenyl)butanoate.

A solution of 1.1 g (3.4 mmol) of methyl 2-[(tert-butoxycarbonyl)amino]-4-(2-chlorophenyl)butanoate in 8 mL of 1:1 $CH_2Cl_2$/TFA is stirred for 1 h. The mixture is concentrated and 10 mL of DMF, 1.5 mL (8.5 mmol) of $iPr_2NEt$, and 0.81 g (3.7 mmol) of indole-4-sulfonyl chloride are added. The mixture is stirred for 12 h, diluted with water, and extracted with EtOAc. The extract is washed with brine, dried over $MgSO_4$, filtered and concentrated. The residue is purified by flash chromatography (0-100% EtOAc in hexanes) to provide 1.0 g (73%) of the sulfonamide. This material (0.48 g, 1.2 mmol) is then dissolved in 5 mL of dioxane and 2.9 mL (2.9 mmol) of 1 M NaOH. After starting material is consumed, the mixture is concentrated, redissolved in water, and extracted with $CH_2Cl_2$. The extract is discarded, and the pH of the aqueous solution is adjusted to 3 with 1 N HCl. The mixture is extracted with $CH_2Cl_2$/DMF. The extract is concentrated to provide 0.39 g (86%) of the acid 4-(2-chlorophenyl)-2-[(1H-indol-4-ylsulfonyl)amino]butanoic acid.

A mixture of 0.1 mmol of 4-(2-chlorophenyl)-2-[(1H-indol-4-ylsulfonyl)amino]butanoic acid and 0.15 mmol of HATU in 1 mL of DMF is added to a mixture of 0.12 mmol of piperidine and 0.044 mL (0.4 mmol) of NMM. The mixture is shaken overnight, concentrated, and purified by preparative HPLC to provide 7.8 mg (17%) Example 55. ESI MS Calc. 459.1; Found: 460.2 (M+H)$^+$.

Examples 56-66 are prepared from 4-(2-chlorophenyl)-2-[(1H-indol-4-ylsulfonyl)amino]butanoic acid and the appropriate amines in a manner similar to the synthesis of Example 55.

Example 56

N-{3-(2-chlorophenyl)-1-[(2-methylpiperidin-1-yl)carbonyl]propyl}-1H-indole-4-sulfonamide from 2-methylpiperidine. ESI MS Calc. 473.2; Found: 474.3 (M+H)$^+$.

Example 57

N-{3-(2-chlorophenyl)-1-[(3-methylpiperidin-1-yl)carbonyl]propyl}-1H-indole-4-sulfonamide from 3-methylpiperidine. ESI MS Calc. 473.2; Found: 474.3 (M+H)$^+$.

Example 58

N-[1-(azepan-1-ylcarbonyl)-3-(2-chlorophenyl)propyl]-1H-indole-4-sulfonamide from hexamethyleneimine. ESI MS Calc. 473.2; Found: 474.3 (M+H)$^+$.

Example 59

N-{3-(2-chlorophenyl)-1-[(4-methylpiperazin-1-yl)carbonyl]propyl}-1H-indole-4-sulfonamide from 1-methylpiperazine. ESI MS Calc. 474.2; Found: 475.3 (M+H)$^+$.

Example 60

N-[3-(2-chlorophenyl)-1-(1,4-oxazepan-4-ylcarbonyl)propyl]-1H-indole-4-sulfonamide from homomorpholine. ESI MS Calc. 475.1; Found: 476.2 (M+H)$^+$.

Example 61

N-{3-(2-chlorophenyl)-1-[(5-oxo-1,4-diazepan-1-yl)carbonyl]propyl}-1H-indole-4-sulfonamide from 5-oxo-1,4-diazepane. ESI MS Calc. 488.1; Found: 489.2 (M+H)$^+$.

Example 62

N-[3-(2-chlorophenyl)-1-(5,6-dihydro[1,2,4]triazolo[4,3-a]pyrazin-7(8H)-ylcarbonyl)propyl]-1H-indole-4-sulfonamide from 5,6,7,8-tetrahydro[1,2,4]-triazole[4,3-a]pyrazine with $Et_3N$ in place of NMM. ESI MS Calc. 498.1; Found: 499.2(M+H)$^+$.

Example 63

N-{1-[(4-acetylpiperazin-1-yl)carbonyl]-3-(2-chlorophenyl)propyl}-1H-indole-4-sulfonamide from 1-acylpiperazine. ESI MS Calc. 502.1; Found: 503.3 (M+H)$^+$.

Example 64

3-(1-{4-(2-chlorophenyl)-2-[(1H-indol-4-ylsulfonyl)amino]butanoyl}piperidin-3-yl)propanoic acid methyl ester from piperidin-3-ylpropanoic acid methyl ester. ESI MS Calc. 531.2; Found: 518.2 (M+H)+.

Example 65

4-(1-{4-(2-chlorophenyl)-2-[(1H-indol-4-ylsulfonyl)amino]butanoyl}piperidin-3-yl)butanoic acid methyl ester from piperidine-3-ylbutanoic acid methyl ester.

Example 66

4-(1-{4-(2-chlorophenyl)-2-[(1H-indol-4-ylsulfonyl)amino]butanoyl}piperidin-4-yl)butanoic acid methyl ester from piperidine-4-ylbutanoic acid methyl ester.

Example 67

N-{3-(2-bromophenyl)-1-[(4-methylpiperidin-1-yl)carbonyl]propyl}-1H-indole-4-sulfonamide

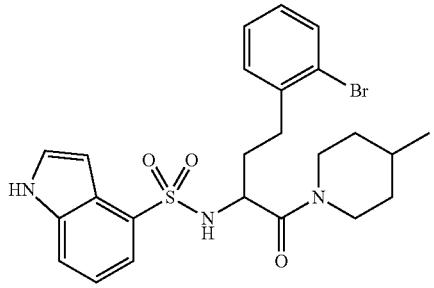 [SMILES: CC1CCN(C(=O)C(CCc2ccccc2Br)NS(=O)(=O)c2cccc3[nH]ccc23)CC1]

tert-Butyl{3-(2-bromophenyl)-1-[(4-methylpiperidin-1-yl)carbonyl]propyl}carbamate is prepared from 2-iodobromobenzene in the same manner that tert-butyl{3-(2-chlorophenyl)-1-[(4-methylpiperidin-1-yl)carbonyl]propyl}carbamate is synthesized.

Example 67 is subsequently prepared from tert-butyl{3-(2-bromophenyl)-1-[(4-methylpiperidin-1-yl)carbonyl]propyl}carbamate and indole-4-sulfonyl chloride in the same manner that Example 5 is synthesized. ESI MS Calc. 517.1; Found: 518.2 (M+H)+.

Example 68

N-{3-(2-methylphenyl)-1-[(4-methylpiperidin-1-yl)carbonyl]propyl}-1H-indole-4-sulfonamide

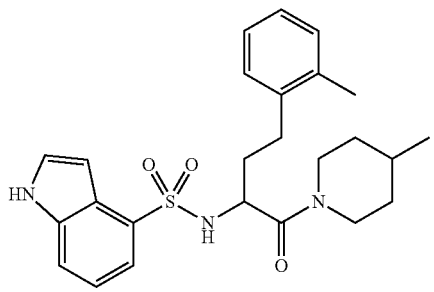 [SMILES: Cc1ccccc1CCC(NS(=O)(=O)c1cccc2[nH]ccc12)C(=O)N1CCC(C)CC1]

A mixture of 30 mg (0.058 mmol) of Example 67, 16 µL (0.12 mmol) of Me$_4$Sn, 3 mg (0.003 mmol) of Pd$_2$(dba)$_3$, and 2 mg (0.007 mmol) of P(o-tol)$_3$ in 2 mL of DMF is stirred under N$_2$ at 80° C. for 6 h. The mixture is filtered and purified by preparatory HPLC to provide 10 mg (38%) of Example 68. ESI MS: Calc: 453.2; Found: 454.3 (M+H)+.

Example 69

N-{3-(2-ethynylphenyl)-1-[(4-methylpiperidin-1-yl)carbonyl]propyl}-1H-indole-4-sulfonamide

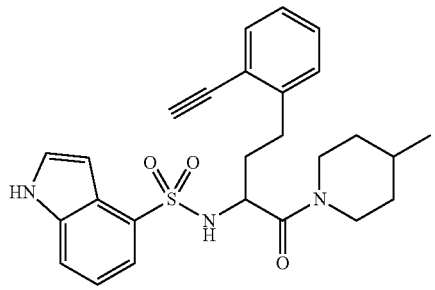 [SMILES: C#Cc1ccccc1CCC(NS(=O)(=O)c1cccc2[nH]ccc12)C(=O)N1CCC(C)CC1]

A mixture of 30 mg (0.058 mmol) of Example 67, 26 µL (0.12 mmol) of trimethylsilyl-acetylene, 24 mg (0.029 mmol) of Pd(dppf)Cl$_2$.CH$_2$Cl$_2$, 11 mg (0.058 mmol) of CuI, and 16 µL (0.12 mmol) of iPr$_2$NH in 0.25 mL of DMF is heated to 80° C. for 3 h under Ar$_2$. Tetrabutylammonium fluoride (1 M in THF; 0.19 mmol) is added and the mixture is stirred for 1 h, and then filtered and purified by preparative HPLC to provide 5 mg (19%) of Example 69. ESI MS Calc. 463.2; Found: 464.4 (M+H)+.

Example 70

N-{3-(2-cyanophenyl)-1-[(4-methylpiperidin-1-yl)carbonyl]propyl}-1H-indole-4-sulfonamide

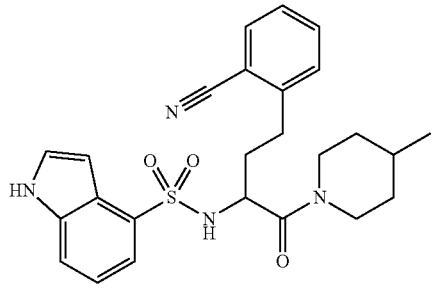

In an argon flushed and sealed pressure tube a mixture of 0.075 g (0.17 mmol) of tert-butyl{3-(2-bromophenyl)-1-[(4-methylpiperidin-1-yl)carbonyl]propyl}carbamate, 6 mg (7 µmol) of Pd$_2$(dba)$_3$, 7.6 mg (14 woe of 1,1'-bisdiphenylphosphino-ferrocene, 12 mg (0.10 mmol) of Zn(CN)$_2$, 2.7 mg (0.041 µmol) of Zn, and 2 mL of anhydrous is heated at 120° C. for 5 h. The mixture is filtered and purified by preparative HPLC to provide 0.39 g (71%) of tert-butyl{3-(2-cyanophenyl)-1-[(4-methylpiperidin-1-yl)carbonyl]propyl}carbamate.

Example 70 is prepared from tert-butyl{3-(2-cyanophenyl)-1-[(4-methylpiperidin-1-yl)carbonyl]propyl}carbamate and indole-4-sulfonyl chloride in the same manner that Example 5 is synthesized. ESI MS Calc. 464.2; Found: 465.2 (M+H)+.

Example 71

N-{3-(3-cyanophenyl)-1-[(4-methylpiperidin-1-yl)carbonyl]propyl}-1H-indole-4-sulfonamide

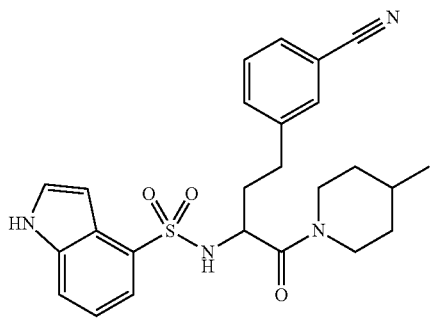 [SMILES: CC1CCN(C(=O)C(CCc2cccc(C#N)c2)NS(=O)(=O)c2cccc3[nH]ccc23)CC1]

To a mixture of 1.0 g (5.1 mmol) of 4-bromoindole and 0.12 g (1.0 mmol) of DMAP in 10 mL of MeCN is added 1.3 g (6.1 mmol) of Boc$_2$O in small portions. After stirring for 2 days, the mixture is concentrated to provide 1.4 g (93%) of N-Boc-4-bromoindole. To 2.0 g (6.7 mmol from multiple experiments) of N-Boc-4-bromoindole in 20 mL of THF at −78° C. is added 5.0 mL (7.0 mmol) of 1.6 M BuLi. After stirring for 30 min, SO$_2$ is gently bubbled through the mixture for 10 min, and then the mixture is warmed to rt over 4 h and concentrated to provide 2.5 g of 75% pure lithium 1-(tert-butoxycarbonyl)-1H-indole-4-sulfinic acid.

A suspension of α-amino-γ-butyrolactone hydrobromide in 30% HBr in HOAc is heated at 100° C. in a sealed tube for 5 days. The mixture is concentrated to give a white solid that is washed with ether to provide 23.1 g (64%) of 2-amino-4-bromo-butyric acid hydrobromide. Acetyl chloride (61 mL, 860 mmol) is added dropwise to 200 mL of MeOH at 0° C. The mixture is stirred at rt for 30 min before 22.5 g (124 mmol) of 2-amino-4-bromo-butyric acid hydrobromide is added. The mixture is stirred overnight and concentrated. The residue is washed with ether to provide 23.5 g (82%) of methyl 4-bromo-2-amino-butyrate hydrochloride. A solution of 27.7 g (330 mmol) of NaHCO$_3$ in 100 mL of water is slowly added to 19.2 g (82.5 mmol) of this material along with 21.6 g (99.0 mmol) of Boc$_2$O in 140 mL of 1,4-dioxane at 0° C. The mixture is warmed to rt and stirred overnight. N,N-dimethyl propane-1,3-diamine (5 mL) is added to the mixture, and it is stirred for 20 min. The mixture is diluted with water then extracted twice with EtOAc. The extracts are washed with water, 1M NaHSO$_4$, and brine, and then combined, dried with Na$_2$SO$_4$, filtered, and concentrated to provide 21.5 g (88%) of 4-bromo-2-tert-butoxycarbonylamino-butyric acid methyl ester as a white solid. To 10 g (34 mmol) of the bromide in 80 mL of acetone is added 15 g (100 mmol) of NaI and the mixture is heated to 60° C. for 2 h. After cooling to rt, Et$_2$O is added, and the resulting precipitate is filtered off. The filtrate is concentrated to provide 12 g (99%) of 4-iodo-2-tert-butoxycarbonylamino-butyric acid methyl ester.

To 0.39 g (6.0 mmol) of Zn powder under Ar$_2$ is added 0.5 mL of DMF and then 26 μL (0.3 mmol) of 1,2-dibromoethane. After stirring at 60° C. for 30 minutes, the mixture is cooled and 7.6 μL (0.06 mmol) of TMSCl is added. After stirring for 30 minutes, 0.34 g (1.0 mmol) of 4-iodo-2-tert-butoxycarbonylamino-butyric acid methyl ester is added and the mixture is stirred at 35° C. for 30 minutes. The mixture is cooled to rt, and 23 mg (0.040 mmol) of Pd(dba)$_2$, 24 mg (0.080 mmol) of (o-tolyl)$_3$P, and then 0.22 mg (0.95 mmol) 3-iodobenzonitrile are added. After stirring at rt for 3 h, EtOAc is added and the mixture is washed with saturated NH$_4$Cl and brine. The extract is concentrated and purified by preparative HPLC to provide 0.14 g (44%) of Boc-(3-cyano)homophenylalanine-OMe. To 0.12 g (0.38 mmol) of this material in 1 mL of 1:1 MeOH/THF is added 0.38 mL (0.75 mmol) of 2 M NaOH. After stirring for 1 h, 1 M NaHSO$_4$ is added, and the mixture is extracted with EtOAc. The extract is washed with brine, dried over Na$_2$SO$_4$, filtered, and concentrated to provide 0.11 g (96%) of 2-[(tert-butoxycarbonyl)amino]-4-(3-cyanophenyl)butanoic acid.

A mixture of 0.11 g (0.26 mmol) of 2-[(tert-butoxycarbonyl)amino]-4-(3-cyanophenyl)butanoic acid, 0.21 g (1.1 mmol) of EDC, and 0.98 g (0.72 mmol) of HOBt, in 1 mL of DMF is stirred for 30 minutes before 4 mg (0.04 mmol) of DMAP and 72 mg (0.72 mmol) of 4-methylpiperidine are added. After stirring overnight, the mixture is concentrated and purified by flash chromatography (15% EtOAc in hexanes) to provide 0.13 g (93%) of the amide product. This material is stirred in 2 mL of 4 M HCl in 1,4-dioxane (8 mmol) and 2 mL of 1,4-dioxane for 2 h, and then it is concentrated to provide 0.10 g (92%) of 3-[3-amino-4-(4-methylpiperidin-1-yl)-4-oxobutyl]benzonitrile.

To 0.29 g (0.77 mmol) of lithium 1-(tert-butoxycarbonyl)-1H-indole-4-sulfinic acid stirring in 1 mL of THF is added 62 mg (0.47 mmol) of NCS. After stirring for 5 minutes, 0.10 g (0.31 mmol) of 3-[3-amino-4-(4-methylpiperidin-1-yl)-4-oxobutyl]benzonitrile is added and the mixture is stirred for 4 h when 10% Na$_2$SO$_3$ and CH$_2$Cl$_2$ are added. The organic phase is dried over Na$_2$SO$_4$, filtered, and concentrated. Preparative TLC (33% EtOAc in hexanes) provides 70 mg (40%) of the sulfonamide. This material (30 mg, 0.053 mmol) in 1 mL of CH$_2$Cl$_2$ is treated with 0.2 mL of TFA for 90 minutes. The mixture is concentrated and purified by preparative TLC (5% MeOH in CH$_2$Cl$_2$) to provide 21 mg (85%) of Example 71. ESI MS Calc. 464.2; Found: 465.7 (M+H)+.

Examples 72-79 are prepared from 4-iodo-2-tert-butoxycarbonylamino-butyric acid methyl ester and the appropriate aryl iodide in the same manner that Example 71 is synthesized.

Example 72

N-{3-(2-fluorophenyl)-1-[(4-methylpiperidin-1-yl)carbonyl]propyl}-1H-indole-4-sulfonamide is prepared from 2-fluoro-iodobenzene. ESI MS Calc. 457.2; Found: 458.7 (M+H)+.

Example 73

N-{3-(3-fluorophenyl)-1-[(4-methylpiperidin-1-yl)carbonyl]propyl}-1H-indole-4-sulfonamide is prepared from 3-fluoro-iodobenzene. ESI MS Calc. 457.2; Found: 458.7 (M+H)+.

Example 74

N-{3-(4-fluorophenyl)-1-[(4-methylpiperidin-1-yl)carbonyl]propyl}-1H-indole-4-sulfonamide is prepared from 4-fluoro-iodobenzene. ESI MS Calc. 457.2; Found: 456.5 (M−H)−.

Example 75

N-{3-(3-chlorophenyl)-1-[(4-methylpiperidin-1-yl)carbonyl]propyl}-1H-indole-4-sulfonamide is prepared from 3-chloro-iodobenzene. ESI MS Calc. 473.2; Found: 474.6 (M+H)+.

Example 76

N-{1-[(4-methylpiperidin-1-yl)carbonyl]-3-(3-nitrophenyl)propyl}-1H-indole-4-sulfonamide is prepared from 4-nitro-iodobenzene. ESI MA Calc. 483.2; Found: 485.7 (M+H)+.

Example 77 methyl 3-{3-[(1H-indol-4-ylsulfonyl)amino]-4-(4-methylpiperidin-1-yl)-4-oxobutyl}benzoate is prepared from methyl 3-iodobenzoate. ESI MS Calc. 497.2; Found 498.4 (M+H)+.

Example 78 methyl 4-{3-[(1H-indol-4-ylsulfonyl)amino]-4-(4-methylpiperidin-1-yl)-4-oxobutyl}benzoate is prepared from methyl 4-iodobenzoate. ESI MS Calc. 497.2; Found: 498.7 (M+H)+.

Example 79

N-{3-(3-bromophenyl)-1-[(4-methylpiperidin-1-yl)carbonyl]propyl}-1H-indole-4-sulfonamide is prepared from 3-bromo-iodobenzene. ESI MS Calc. 517.1; Found: 518.5 (M+H)+.

Example 80

N-{3-(3-chloropyridin-2-yl)-1-[(4-methylpiperidin-1-yl)carbonyl]propyl}-1H-indole-4-sulfonamide

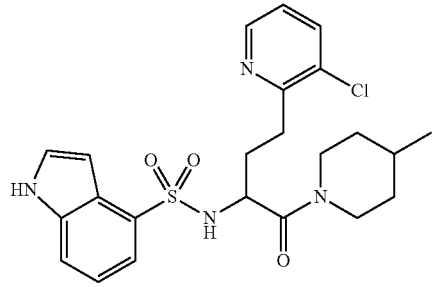 [SMILES: CC1CCN(C(=O)C(CCc2ncccc2Cl)NS(=O)(=O)c2cccc3[nH]ccc23)CC1]

A mixture of 1.1 g (8.0 mmol) of anhydrous CuBr, 30 mL of anhydrous THF, and 16 mL (8.0 mmol) of 0.5 M (1,3-dioxan-2-ylethyl)magnesium bromide in THF is stirred under Ar2 at −78° C. for 20 min. To this is added 0.38 g (2.0 mmol) of 2-bromo-3-chloropyridine bromide and the mixture is stirred for 3 h at −78° C. and then 12 h at rt. Aqueous saturated NH4OH is added and the mixture is extracted with EtOAc. The extracts are washed with brine, dried (MgSO4), and purified by flash chromatography (0-50% EtOAc in hexanes) to provide 0.19 g (42%) of the coupled product. To this material in 10 mL of THF at 0° C. is added 0.5 mL of 70% HClO4 in 15 ml THF. In addition, 5 mL of H2O are added and the mixture is stirred at 80° C. for 1 h, and then at rt for 18 h. The mixture is neutralized with NaHCO3 and extracted with EtOAc. The extract is washed with brine, dried over MgSO4, filtered, and concentrated to provide the 0.11 g (76%) of 3-(3-chloropyridin-2-yl)propanal.

Example 80 is prepared from 3-(3-chloropyridin-2-yl)propanal and indole-4-sulfonyl chloride in the same manner that Example 5 is prepared from 3-(2-chlorophenyl)propanal and benzensulfonyl chloride. ESI MS Calc. 474.2; Found: 475.2 (M+H)+.

Example 81

N-{1-[(4-methylpiperidin-1-yl)carbonyl]-3-(2-prop-1-yn-1-ylphenyl)propyl}-1H-indole-4-sulfonamide

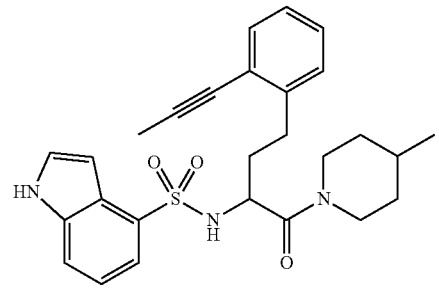 [SMILES: CC#Cc1ccccc1CCC(NS(=O)(=O)c1cccc2[nH]ccc12)C(=O)N1CCC(C)CC1]

A mixture of 30 mg (0.058 mmol) of Example 67, 6.5 μL (0.12 mmol) of propylene, 24 mg (0.029 mmol) of Pd(dppf)Cl2.CH2Cl2, 11 mg (0.058 mmol) of CuI, and 16 μL (0.12 mmol) of iPr2NH in 0.25 mL of DMF is heated to 80° C. for 3 h under Ar2. Preparative HPLC provides 26 mg (94%) of Example 81. ESI MS Calc. 477.2; Found: 478.3 (M+H)+.

Example 82

4-amino-3,5-dichloro-N-{1-[(4-methylidenepiperidin-1-yl)carbonyl]-3-phenylpropyl}benzenesulfonamide

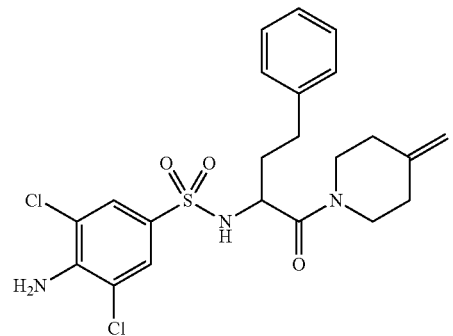 [SMILES: C=C1CCN(C(=O)C(CCc2ccccc2)NS(=O)(=O)c2cc(Cl)c(N)c(Cl)c2)CC1]

A mixture of 0.12 g (0.43 mmol) of Boc-(D/L)-homophenylalanine, 99 mg (0.52 mmol) of EDC, 58 mg (0.43 mmol) of HOBt hydrate, 57 mg (0.43 mmol) of 4-methylene-piperidine hydrochloride, and 0.11 mL (0.64 mmol) of iPr2NEt in 2.5 mL of DMA is heated to 70° C. in a microwave reactor for 10 min. The mixture is diluted in EtOAc, washed with 1M KHSO4, NaHCO3, and brine, and then dried over MgSO4, filtered, and concentrated to provide 0.14 g (90%) of the amide product. This material is stirred in 2 mL of 4 M HCl in 1,4-dioxane for 1 h, and then is concentrated. The residue is stirred in 5 mL of CH2Cl2 with 0.11 g (0.40 mmol) of 4-amino-3,5-dichlorbenzensulfonyl chloride and 0.20 mL (1.2 mmol) of iPr2NEt for 1 h. Additional CH2Cl2 is added, and the mixture is washed with 1M HCl and dried over MgSO$_4$. After being filtered and concentrated, the mixture is purified by flash chromatography (15-50% EtOAc in hexanes) to provide 0.16 g (87%) of Example 82. ESI MS Calc. 481.1; Found: 482.2 (M+H)$^+$.

Example 83

4-amino-3,5-dichloro-N-{(1R)-1-[(4-methylpiperidin-1-yl)carbonyl]-3-phenylpropyl}benzenesulfonamide is prepared from Boc-(D)-homophenylalanine and 4-methylpiperidine in the same manner that Example 82 is synthesized. ESI MS Calc. 483.1; Found: 484.2 (M+H)$^+$.

Example 84

3-{3-[(1H-indol-4-ylsulfonyl)amino]-4-(4-methylpiperidin-1-yl)-4-oxobutyl}benzoic acid

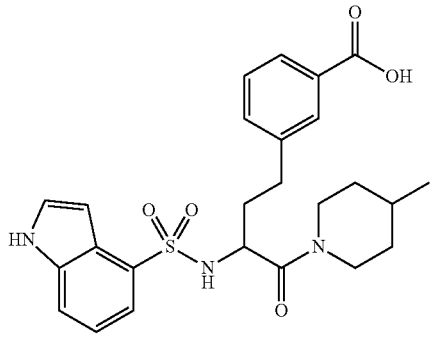 [SMILES: CC1CCN(C(=O)C(CCc2cccc(C(=O)O)c2)NS(=O)(=O)c2cccc3[nH]ccc23)CC1]

A solution of 90 mg (0.22 mmol) of 3-[3-tert-butoxycarbonylamino-4-(4-methyl-piperidin-1-yl)-4-oxo-butyl]-benzoic acid methyl ester (prepared in the synthesis of Example 77) in 1 mL of 1:1 MeOH/1,4-dioxane and 0.5 mL of 1 N NaOH is stirred for 3 h. The organic phase is separated and suspended in 2 mL of water. The pH is adjusted to 2 with HCl, and the resulting precipitate is filtered to provide 85 mg (98%) of 3-[3-tert-butoxycarbonylamino-4-(4-methyl-piperidin-1-yl)-4-oxo-butyl]-benzoic acid.

Example 84 is prepared from 3-[3-tert-butoxycarbonylamino-4-(4-methyl-piperidin-1-yl)-4-oxo-butyl]-benzoic acid and lithum 1-(tert-butoxycarbonyl)-1H-indole-4-sulfinic acid in the same manner as Example 71. ESI MS Calc. 483.2; Found. 484.8 (M+H)$^+$.

Example 85

3-{3-[(1H-indol-4-ylsulfonyl)amino]-4-(4-methylpiperidin-1-yl)-4-oxobutyl}benzamide

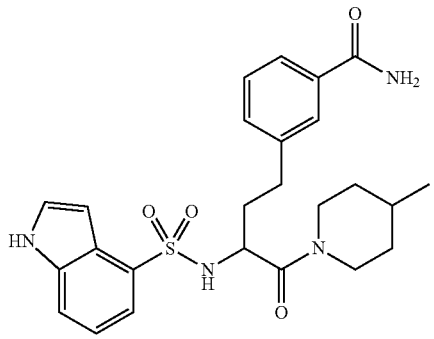 [SMILES: CC1CCN(C(=O)C(CCc2cccc(C(N)=O)c2)NS(=O)(=O)c2cccc3[nH]ccc23)CC1]

A mixture of 85 mg (0.21 mmol) of 3-[3-tert-butoxycarbonylamino-4-(4-methyl-piperidin-1-yl)-4-oxo-butyl]-benzoic acid, 81 mg (0.42 mmol) of EDC, 57 mg (0.42 mmol), and 2.6 mg (0.021 mmol) of DMAP is stirred in DMF for 2 h at rt. After cooling to −40° C. ~0.2 mL of NH$_3$ is condensed into the mixture. The resulting solution is sealed and stirred at rt for 10 h. The mixture is concentrated and purified by preparatory TLC (10% MeOH in CH$_2$Cl$_2$) to provide 66 mg (78%) of [3-(3-carbamoyl-phenyl)-1-(4-methyl-piperidine-1-carbonyl)-propyl]-carbamic acid tert-butyl ester.

Example 85 is prepared from [3-(3-carbamoyl-phenyl)-1-(4-methyl-piperidine-1-carbonyl)-propyl]-carbamic acid tert-butyl ester and lithum 1-(tert-butoxycarbonyl)-1H-indole-4-sulfinic acid in the same manner as Example 71. ESI MS Calc. 482.2; Found. 483.7 (M+H)$^+$.

Example 86

4-amino-3,5-dichloro-N-{2-(4-methylpiperidin-1-yl)-2-oxo-1-[(phenylamino) methyl] ethyl}benzenesulfonamide

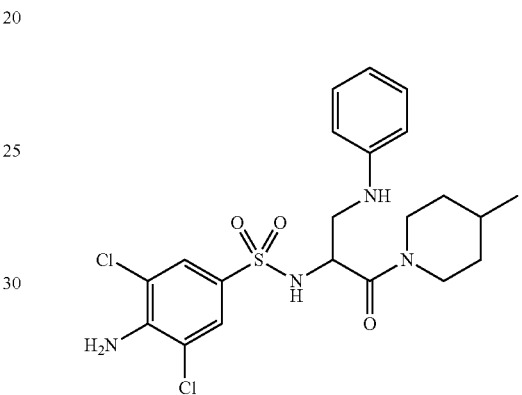

A mixture of 20 g (97 mmol) of Boc-(D/L)-serine, 13 g (97 mmol) of HOBt, 19 g (97 mmol) of EDC, and 11 mL (97 mmol) of 4-methylpiperidine in 40 mL of DMF is stirred at 80° C. for 12 h. The mixture is poured into water and extracted with EtOAc. The extract is washed with water and brine, dried over MgSO$_4$, filtered, and concentrated to provide 24 g (86%) of the amide product. This material (27 g, 94 mmol from multiple experiments) is stirred in CH$_2$Cl$_2$ and 4 M HCl in 1,4-dioxane overnight at 50° C., and then is concentrated to provide 18 g (86%) of the amine hydrochloride product. This material (10 g, 37 mmol), 4-amino-3,5-dichlorobenzenesulfonyl chloride (9.7 g, 37 mmol), and Et$_3$N (16 mL, 110 mmol) are stirred in 40 mL of CH$_2$Cl$_2$ for 12 h. Additional CH$_2$Cl$_2$ is added, and the mixture is washed with 3 N HCl and brine, and then dried with MgSO$_4$, filtered, and concentrated. Chromatography (0-100% EtOAc in hexanes) provides 8.7 g (57%) of the sulfonamide product. This sulfonamide (2.9 g, 7.1 mmol) in 20 mL of THF is added slowly to 0.80 g (18 mmol) of NaH (60% in mineral oil) in 50 mL of THF. After stirring for 10 minutes, 1.3 g (7.0 mmol) of TsCl is added. After stirring for 12 h, water is added, and the mixture is extracted with EtOAc. The extract is washed with saturated NaHCO$_3$ and brine, and dried with MgSO$_4$, filtered, and concentrated. Chromatography (0-5% MeOH in CH$_2$Cl$_2$) provides 2.2 g (79%) of 2,6-dichloro-4-({2-[(4-methylpiperidin-1-yl)carbonyl]aziridin-1-yl}sulfonyl)aniline.

A mixture of 0.15 g (0.38 mmol) of 2,6-dichloro-4-({2-[(4-methylpiperidin-1-yl)carbonyl]aziridin-1-yl}sulfonyl) aniline, 36 mg (0.38 mmol) of aniline, and 0.13 g (0.12 mmol) of β-cyclodextrin in 2 mL of MeOH is heated to 100° C. in a microwave reactor for 30 minutes. The mixture is filtered and purified by preparative HPLC to provide 25 mg (14%) of Example 86. ESI MS Calc. 484.1; Found: 485 (M+H)$^+$.

Examples 87-98 are prepared from 2,6-dichloro-4-({2-[(4-methylpiperidin-1-yl)carbonyl]aziridin-1-yl}sulfonyl)aniline and the appropriate aniline in the same manner that Example 86 is synthesized.

Example 87

4-amino-3,5-dichloro-N-[1-{[(2-methylphenyl)amino]methyl}-2-(4-methyl-piperidin-1-yl)-2-oxoethyl]benzenesulfonamide is prepared from 2-methylaniline. ESI MS Calc. 498.1; Found: 499 (M+H)+.

Example 88

4-amino-3,5-dichloro-N-[1-{[(3-methylphenyl)amino]methyl}-2-(4-methyl-piperidin-1-yl)-2-oxoethyl]benzenesulfonamide is prepared from 3-methylaniline. ESI MS Calc. 498.1; Found: 499.1 (M+H)+.

Example 89

4-amino-3,5-dichloro-N-[1-{[(2-fluorophenyl)amino]methyl}-2-(4-methyl-piperidin-1-yl)-2-oxoethyl]benzenesulfonamide is prepared from 2-fluoroaniline. ESI MS Calc. 502.1; Found: 503 (M+H)+.

Example 90

4-amino-3,5-dichloro-N-[1-{[(3-fluorophenyl)amino]methyl}-2-(4-methyl-piperidin-1-yl-2-oxoethyl]benzenesulfonamide is prepared from 3-fluoroaniline. ESI MS Calc. 502.1; Found: 503 (M+H)+.

Example 91

4-amino-3,5-dichloro-N-[1-{[(4-fluorophenyl)amino]methyl}-2-(4-methyl-piperidin-1-yl)-2-oxoethyl]benzenesulfonamide is prepared from 4-fluoroaniline. ESI MS Calc. 502.1; Found: 503.3 (M+H)+.

Example 92

4-amino-3,5-dichloro-N-[1-{[(2-cyanophenyl)amino]methyl}-2-(4-methyl-piperidin-1-yl)-2-oxoethyl]benzenesulfonamide is prepared from 2-cyanoaniline. ESI MS Calc. 509.1; Found: 510.2 (M+H)+.

Example 93

4-amino-3,5-dichloro-N-[1-{[(2-chlorophenyl)amino]methyl}-2-(4-methyl-piperidin-1-yl-2-oxoethyl]benzenesulfonamide is prepared from 2-chloroaniline. ESI MS Calc. 518.1; Found: 519.2 (M+H)+.

Example 94

4-amino-3,5-dichloro-N-[1-{[(3-chlorophenyl)amino]methyl}-2-(4-methyl-piperidin-1-yl)-2-oxoethyl]benzenesulfonamide is prepared from 3-chloroaniline. ESI MS Calc. 518.1; Found: 519 (M+H)+.

Example 95

4-amino-3,5-dichloro-N-[1-{[(2,4-difluorophenyl)amino]methyl}-2-(4-methylpiperidin-1-yl)-2-oxoethyl]benzenesulfonamide is prepared from 2,4-difluoroaniline. ESI MS Calc. 520.1; Found: 521.1 (M+H)+.

Example 96

4-amino-3,5-dichloro-N-[1-{[(2,6-difluorophenyl)amino]methyl}-2-(4-methylpiperidin-1-yl)-2-oxoethyl]benzenesulfonamide is prepared from 2,6-difluoroaniline. ESI MS Calc. 520.1; Found: 521 (M+H)+.

Example 97

4-amino-3,5-dichloro-N-[1-{[(2-chloro-4-fluorophenyl)amino]methyl}-2-(4-methylpiperidin-1-yl)-2-oxoethyl]benzenesulfonamide is prepared from 2-chloro-4-fluoroaniline. ESI MS Calc. 536.1; Found: 536.1 (M+H)+.

Example 98

4-amino-3,5-dichloro-N-[1-{[(2-sulfamoylphenyl)amino]methyl}-2-(4-methylpiperidin-1-yl)-2-oxoethyl]benzenesulfonamide is prepared from 2-aminobenzensulfonamide. ESI MS Calc. 562.1; Found: 564.2 (M+H)+.

Example 99

4-amino-3,5-dichloro-N-[2-(4-methylpiperidin-1-yl)-2-oxo-1-(phenoxymethyl)ethyl]benzenesulfonamide

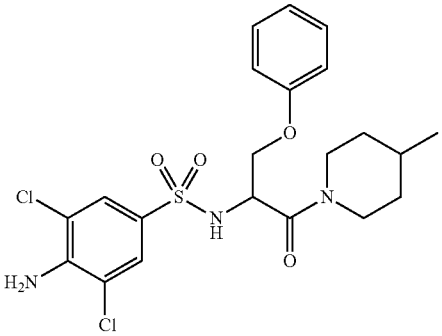

Phenol (36 mg, 0.38 mmol) is stirred in 1 mL of DMF with 0.76 mL (0.76 mmol) of 1.0 M LHMDS in THF for 10 minutes before 0.15 g (0.38 mmol) of 2,6-dichloro-4-({2-[(4-methylpiperidin-1-yl)carbonyl]aziridin-1-yl}sulfonyl)aniline in 1 mL of DMF is added. After heating at 80° C. for 2 h, the mixture is purified by preparative HPLC to provide 32 mg (17%) of Example 99. ESI MS Calc. 485.1; Found: 486 (M+H)+.

Examples 100-105 are prepared from 2,6-dichloro-4-({2-[(4-methylpiperidin-1-yl)carbonyl]aziridin-1-yl}sulfonyl)aniline and the appropriate phenol in the same manner that Example 99 is synthesized.

Example 100

4-amino-3,5-dichloro-N-{2-(4-methylpiperidin-1-yl)-2-oxo-1-[(pyridin-3-yloxy)methyl]ethyl}benzenesulfonamide is prepared from 3-hydroxy-pyridine. ESI MS Calc. 486.1; Found: 487 (M+H)+.

Example 101

4-amino-3,5-dichloro-N-{1-[(2-fluorophenoxy)methyl]-2-(4-methylpiperidin-1-yl)-2- oxoethyl}benzenesulfonamide is prepared from 2-fluorophenol. ESI MS Calc. 503.1; Found: 504.2 (M+H)⁺.

Example 102

4-amino-3,5-dichloro-N-{1-[(2-chlorophenoxy)methyl]-2-(4-methylpiperidin-1-yl)-2-oxoethyl}benzenesulfonamide is prepared from 2-chlorophenol. ESI MS Calc. 519.1; Found: 520.1 (M+H)⁺.

Example 103

4-amino-3,5-dichloro-N-{1-[(3-chlorophenoxy)methyl]-2-(4-methylpiperidin-1-yl)-2-oxoethyl}benzenesulfonamide is prepared from 3-chlorophenol. ESI MS Calc. 519.1; Found: 520.2 (M+H)⁺.

Example 104

4-amino-3,5-dichloro-N-{1-[(isoquinolin-5-yloxy)methyl]-2-(4-methylpiperidin-1-yl)-2-oxoethyl}benzenesulfonamide is prepared from 5-hydroxyisoquinoline. ESI MS Calc. 536.1; Found: 537.2 (M+H)⁺.

Example 105

4-amino-3,5-dichloro-N-[2-(4-methylpiperidin-1-yl)-2-oxo-1-{[2-(trifluoromethyl)phenoxy]methyl}ethyl]benzenesulfonamide is prepared from 2-trifluromethylphenol. ESI MS Calc. 553.1; Found: 554.2 (M+H)⁺.

Example 106

N-[3-(2-chlorophenyl)-1-{[4-(hydroxymethyl)piperidin-1-yl]carbonyl}propyl]-1H-indole-4-sulfonamide

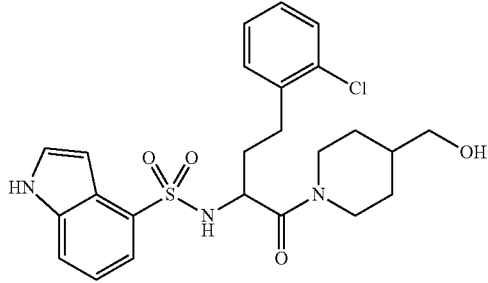 [SMILES: O=C(C(CCc1ccccc1Cl)NS(=O)(=O)c1cccc2[nH]ccc12)N1CCC(CO)CC1]

A mixture of 20 mg (0.051 mmol) of 4-(2-chlorophenyl)-2-[(1H-indol-4-ylsulfonyl)amino]butanoic acid, 7.0 mg (0.061 mmol) of 4-hydroxymethyl-piperidine, 8.2 mg (0.061 mmol) of HOBt, 12 mg (0.061 mmol) of EDC, and ~1 mg of DMAP in 1 mL of DMF is stirred for 4 h. Purification by preparative HPLC provides 25 mg (99%) of Example 106. ESI MS Calc. 489.2; Found: 490.5 (M+H)⁺.

Example 107 methyl 1-{4-(2-chlorophenyl)-2-[(1H-indol-4-ylsulfonyl)amino]butanoyl}piperidine-4-carboxylate is prepared from 4-(2-chlorophenyl)-2-[(1H-indol-4-ylsulfonyl)amino]butanoic acid and methyl piperidine-4-carboxylate in same manner Example 106 is synthesized. ESI MS Calc. 517.1; Found: 518.5 (M+H)⁺.

Example 108

N-{3-(2-chlorophenyl)-1-[(4-methylpiperidin-1-yl)carbonyl]propyl}-2-oxo-2,3-dihydro-1H-indole-4-sulfonamide

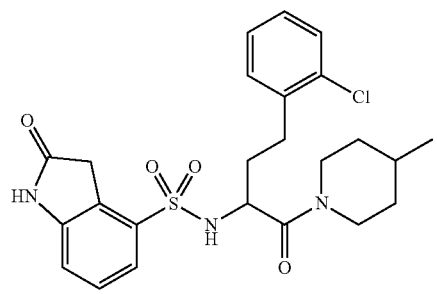 [SMILES: CC1CCN(C(=O)C(CCc2ccccc2Cl)NS(=O)(=O)c2cccc3c2CC(=O)N3)CC1]

To a solution of 50 mg (0.11 mmol) of Example 22 in 1 ml of t-butanol is added 110 mg (0.32 mmol) of pyridium bromide perbromide. The solution is stirred for 2 h, concentrated, and dissolved in 1 mL of HOAc. Zinc powder (65 mg, 1.0 mmol) is added, and the mixture is stirred for 30 minutes. The mixture is diluted with EtOAc and washed with water and brine, and then dried over MgSO₄, filtered, and concentrated. Preparative HPLC provides 22 mg (43%) of Example 108. ESI MS Calc. 489.2; Found: 490.3 (M+H)⁺.

Example 109

N-{3-(2-chlorophenyl)-1-[(4-methylpiperidin-1-yl)carbonyl]propyl}-2-oxo-2,3-dihydro-1H-indole-6-sulfonamide is prepared from Example 23 in the same manner that Example 108 is synthesized. ESI MS Calc. 489.2; Found: 490.3 (M+H)⁺.

Example 110

N-{3-(2-chlorophenyl)-1-[(4-methylpiperidin-1-yl)carbonyl]propyl}-3-cyano-1H-indole-4-sulfonamide

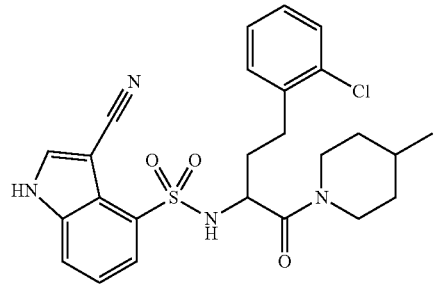 [SMILES: CC1CCN(C(=O)C(CCc2ccccc2Cl)NS(=O)(=O)c2cccc3[nH]cc(C#N)c23)CC1]

Example 22 (20 mg, 0.042 mmol) in 1 mL of dry MeCN at 0° C. is treated with 3.6 μL (0.042 mmol) of chlorosulphonyl isocyanate. After 30 minutes, 3.9 mL (0.050 mmol) of DMF is added and the mixture is stirred for 2 h. Purification by preparative HPLC provides 7.0 mg (33%) of Example 110. ESI MS Calc. 498.2; Found: 499.4 (M+H)⁺.

Example 111
4-amino-3,5-dichloro-N-{2-(4-methylpiperidin-1-yl)-2-oxo-1-[(phenylsulfanyl)methyl]ethyl}benzenesulfonamide

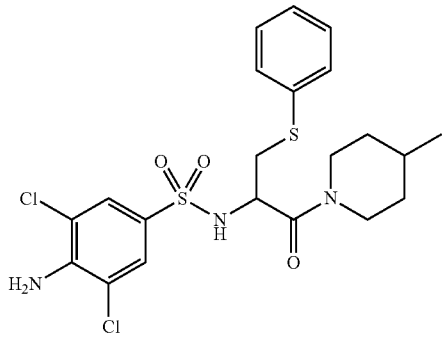 [SMILES: CC1CCN(C(=O)C(CSc2ccccc2)NS(=O)(=O)c2cc(Cl)c(N)c(Cl)c2)CC1]

Thiophenol (26 µL, 0.26 mmol) is stirred in 2 mL of MeOH with 0.10 g (0.26 mmol) of 2,6-dichloro-4-({2-[(4-methylpiperidin-1-yl)carbonyl]aziridin-1-yl}sulfonyl)aniline for 12 h. The mixture is concentrated and purified by flash chromatography (2:1 hexanes/EtOAc) to provide 61 mg (47%) of Example 111. ESI MS Calc. 501.1; Found: 502 (M+H)$^+$.

Example 112
3-chloro-N-{3-(2-chlorophenyl)-1-[(4-methylpiperidin-1-yl)carbonyl]propyl}-1H-indole-4-sulfonamide

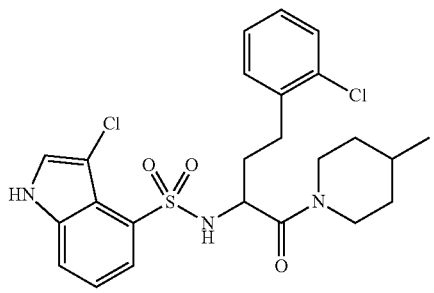 [SMILES: CC1CCN(C(=O)C(CCc2ccccc2Cl)NS(=O)(=O)c2cccc3[nH]cc(Cl)c23)CC1]

A mixture of 20 mg (0.042 mmol) of Example 22 and 5.6 mg (0.042 mmol) of NCS in 1 mL of DMF is stirred for 24 h. The mixture is purified by preparative HPLC to provide 11 mg (51%) of Example 112. ESI MS: Calc: 507.1; Found: 508.4 (M+H)$^+$

Example 113
N-{1-[(4-methylpiperidin-1-yl)carbonyl]-3-[2-(methylsulfonyl)phenyl]propyl}-1H-indole-4-sulfonamide

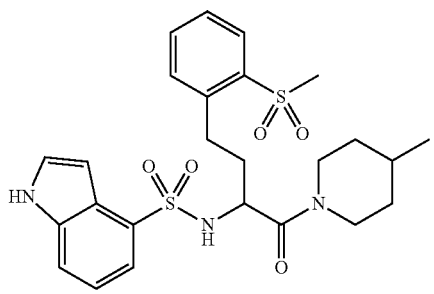 [SMILES: CC1CCN(C(=O)C(CCc2ccccc2S(C)(=O)=O)NS(=O)(=O)c2cccc3[nH]ccc23)CC1]

A mixture of 30 mg (0.058 mmol) of Example 67, 33 mg (0.17 mmol) of CuI, and 17 mg of sodium methylsulfinate in 1 mL of DMSO is heated at 110° C. for 12 h. The mixture is cooled, 10 mL of aq. NH$_4$OH is added and the mixture is extracted with EtOAc. The extract is washed with brine, dried over MgSO$_4$, filtered, concentrated, and purified by preparatory HPLC to provide 10 mg (17%) of Example 113 as a white solid. ESI MS: Calc: 517.2; Found: 518.2 (M+H)$^+$

Example 114
N-{3-[2-(3-hydroxy-3-methylbut-1-yn-1-yl)phenyl]-1-[(4-methylpiperidin-1-yl)carbonyl]propyl}-1H-indole-4-sulfonamide

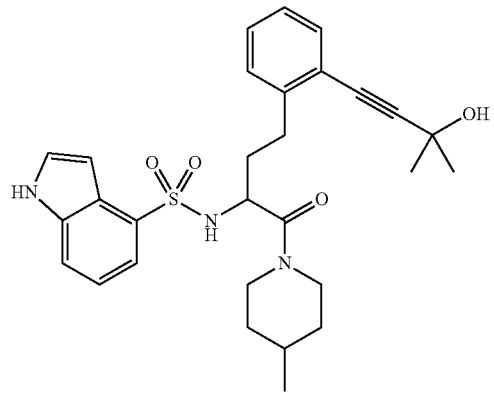 [SMILES: CC1CCN(C(=O)C(CCc2ccccc2C#CC(C)(C)O)NS(=O)(=O)c2cccc3[nH]ccc23)CC1]

To a mixture of 30 mg (0.058 mmol) of Example 67, 24 mg (0.03 mmol) of Pd(dppf)Cl$_2$.CH$_2$Cl$_2$, 1 mg (0.06 mmol) of CuI under Ar is added 11 µL (0.12 mmol) of 3-hydroxy-3-methylbut-1-yne, 16 µL (0.12 mmoL) of iPr$_2$NH, and 0.25 mL of DMF are added. The mixture is heated to 80° C. for 12 h in a sealed pressure tube. The mixture is cooled, filtered, and purified by preparatory HPLC to provide 20 mg (66%) of Example 114 as a yellow solid. ESI MS: Calc: 521.2; Found: 522.4 (M+H)$^+$.

Example 115
4-amino-3,5-dichloro-N-{(1S)-1-[(cis)-octahydroisoquinolin-2(1H)-ylcarbonyl]-3-phenylpropyl}benzenesulfonamide

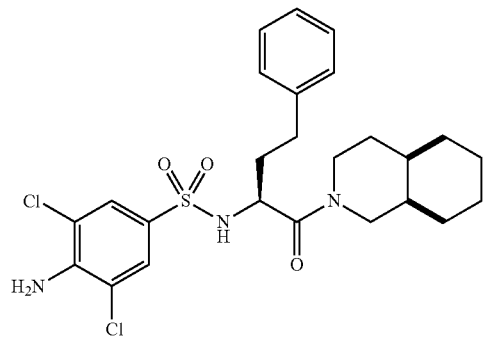

Example 115 is prepared from Boc-(L)-homophenylalanine, (±)-cis-decahydroisoquinoline, and 4-amino-3,5-dichlorobenzenesulfonyl chloride in the same manner that Example 1 is synthesized. ESI MS: Calc: 523.2; Found: 524.3 (M+H)$^+$.

Example 116

4-amino-3,5-dichloro-N-{(1R)-1-[(cis)-octahydroisoquinolin-2(1H)-ylcarbonyl]-3-phenylpropyl}benzenesulfonamide

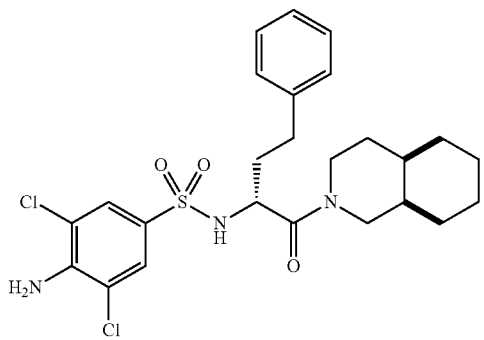

Example 116 is prepared from Boc-(D)-homophenylalanine, (±)-cis-decahydroisoquinoline, and 4-amino-3,5-dichlorobenzenesulfonyl chloride in the same manner that Example 1 is synthesized. ESI MS: Calc: 523.2; Found: 524.3 (M+H)⁺.

Example 117

4-amino-3,5-dichloro-N-{(1R)-1-[(trans)-octahydroisoquinolin-2(1H)-ylcarbonyl]-3-phenylpropyl}benzenesulfonamide is prepared from Boc-(D)-homo-phenylalanine, (±)-trans-decahydroisoquinoline, and 4-amino-3,5dichlorobenzene-sulfonyl chloride in the same manner that Example 1 is synthesized. ESI MS: Calc: 523.2; Found: 524.3 (M+H)⁺.

Example 118

4-amino-3,5-dichloro-N-{(1R)-1-[(trans)-octahydroquinolin-1(2H)-ylcarbonyl]-3-phenylpropyl}benzenesulfonamide is prepared from Boc-(D)-homo-phenylalanine, (±)-trans-decahydroquinoline, and 4-amino-3,5dichlorobenzene-sulfonyl chloride in the same manner that Example 1 is synthesized. ESI MS: Calc: 523.2; Found: 524.3 (M+H)⁺.

Example 119

N-{3-(2-chlorophenyl)-1-[(4-methylpiperidin-1-yl)carbonyl]propyl}-3-[(dimethylamino)methyl]-1H-indole-4-sulfonamide

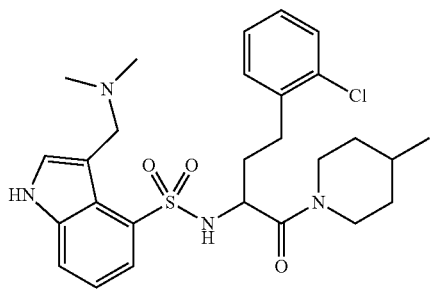 [SMILES: CC1CCN(C(=O)C(CCc2ccccc2Cl)NS(=O)(=O)c2cccc3[nH]cc(CN(C)C)c23)CC1]

To a solution of 0.16 g (0.33 mmol) of Example 22 in 2 mL of DMF is added 0.15 g (1.6 mmol) of N,N-dimethylmethyleneammonium chloride in four portions over the course of 24 h. The mixture is purified by preparative HPLC to provide 97 mg (56%) of Example 119. ESI MS: Calc: 530.2; Found: 531.6 (M+H)⁺.

Example 120

3-(1-{4-(2-chlorophenyl)-2-[(1H-indol-4-ylsulfonyl)amino]butanoyl}piperidin-3-yl)propanoic acid

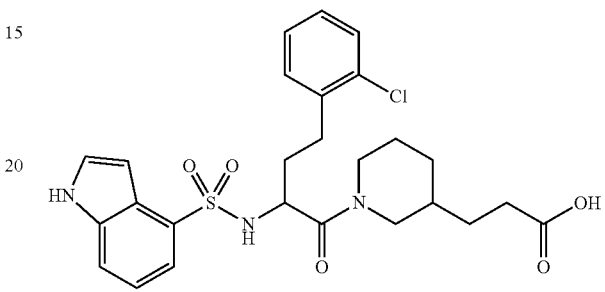

Example 64 (0.1 mmol) in 1 mL of dioxane and 0.2 mL (0.2 mmol) of 1 M NaOH is stirred until consumed. The mixture is concentrated and purified by preparative HPLC to provide 18 mg (34%) of Example 120. ESI MS Calc. 531.2; Found: 532.3 (M+H)⁺.

Example 121

4-(1-{4-(2-chlorophenyl)-2-[(1H-indol-4-ylsulfonyl)amino]butanoyl}piperidin-3-yl)butanoic acid is prepared by saponification of Example 65 in the same manner that Example 120 is synthesized. ESI MS Calc. 545.2; Found: 546.3 (M+H)⁺.

Example 122

4-(1-{4-(2-chlorophenyl)-2-[(1H-indol-4-ylsulfonyl)amino]butanoyl}piperidin-4-yl)butanoic acid is prepared by saponification of Example 66 in the same manner that Example 120 is synthesized. ESI MS Calc. 545.2; Found: 546.3 (M+H)⁺.

Example 123 methyl 1-[2-{[(3-chloro-1H-indol-4-yl)sulfonyl]amino}-4-(2-chlorophenyl)butanoyl]piperidine-4-carboxylate

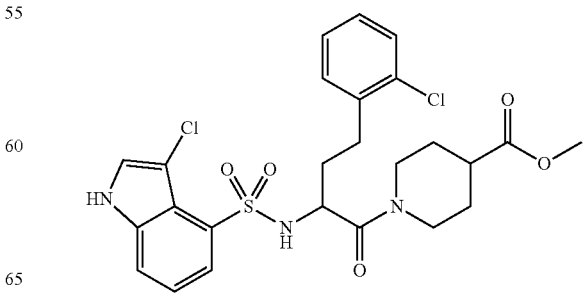

A mixture of 25 mg (0.048 mmol) of Example 107 and 6.4 mg (0.048 mmol) of NCS in 1 mL of DMF is stirred for 18 h. The mixture is purified by preparative HPLC to provide 10 mg (38%) of Example 123. ESI MS: Calc: 551.1; Found: 552.4 (M+H)$^+$.

Procedures for Identification of CCR10 Antagonists

CCR10 FLIPR Assay

Preferred compounds have an IC$_{50}$ of 500 nM or lower in this assay.

To a 1 liter bottle of Hams F12 (Mediatech #10-080-CM) add 100 mL Fetal Bovine Serum (Mediatech #35-015-CV), 10 mL geneticin (Invitrogen #10131-027), and 2 mL Zeocin (Invitrogen #R250-05).

CHO-K1 hCCR10 cells (Euroscreen cat #ES-143-A) are diluted in media to a final concentration of 2.8×10$^5$ cells/mL and 25 µL of this suspension are added to each well of a BD384 well TC treated assay plate (VWR #62406-490). This will yield approximately 7,000 cells/well. The plate is incubated at 37° C./5% CO$_2$ overnight.

The EC$_{50}$ and EC$_{70}$ should be calculated each time the assay is performed. CTACK/CCL27 (R&D Systems #376-CT; 30 µM stock) is diluted to a working concentration of 10 µM (2.5 µM final) in peptide buffer (HBSS/1 mM CaCl/1 mM MgSO$_4$/0.1% BSA). This is serially dilute 1:3 in the same buffer for a total of 11 concentrations of peptide. The assay below is run and the EC$_{50}$ of the CCL27 is calculated. Test compounds are assayed at the EC$_{70}$.

Cell plates are removed from the incubator, inverted to "flick" out media and tapped dry on a paper towel. 25 µL 1× FLUO-4 dye/2 mM probenicid (Molecular probes Fluo-4 kit #F36206) are added to each well. The plates are then incubated 30 minutes at 37° C./5% CO$_2$, then removed and incubated 30 additional minutes at room temperature. 5 µL diluted (see below) test compound (final concentration based on 30 µL) are added to appropriate wells. The wells are mixed and incubated at room temperature for 15 minutes. The plates are then placed on FLIPR and 10 µL CCL27 (30 µM stock diluted to appropriate 4× of final concentration at EC$_{70}$) from a Greiner 384 well polypropylene plate are transferred.

Plate reader data are analyzed using ActivityBase software (ID Business Solutions, Ltd). The RFU signals from the plate reader are converted to percent of control (POC) values using the formula:

POC=100*(Signal−BCTRL)÷(PCTRL−BCTRL)

Where Signal is the test well signal, BCTRL is the average of background (negative control) well signals on the plate and PCTRL is the average of positive control well signals on the plate.

For the concentration responsive compounds, POC as a function of test compound concentration are fitted to a 4-parameter logistic equation of the form:

$Y=A+(B-A)/[1+(x/C)^P]$

Where A, B, C, and D are fitted parameters (parameter B is fixed at zero POC), and x and y are the independent and dependent variables, respectively. The IC$_{50}$ (50% inhibitory concentration) is determined as the inflection point parameter, C.

1× Assay Buffer: 1× HBSS (10×, Invitrogen #14185-027), 10 mM HEPES pH 7.4, 0.35 g/L sodium bicarbonate, 1 mM CaCl$_2$, 1 mM MgSO$_4$ Chemotaxis Assay Test compounds are evaluated for their ability to inhibit chemotaxis of Baf/3 cells expressing human CCR10 (hereinafter Baf/3-hCCR10 cells) in response to CCL27. Preferred compounds have IC$_{50}$<1 µM in this assay.

Test compounds are diluted (2× the final concentration) in CTX media (RPMI 1640 (Gibco-BRL #11875-093) supplemented with 0.1% BSA (Sigma #A3803)). Control solutions contain 1% DMSO in CTX media. Baf/3-hCCR10 cells are re-suspended in CTX media to a concentration of 4×10$^6$ cells/mL In a 96 well plate, 100 µL the Baf/3-hCCR10 cell suspension is combined with 100 µL of the test compound solution and the plate is then incubated for 15 minutes at room temperature.

150 µL of a solution of the chemoattractant (2× the EC$_{70}$ for CCL27) in CTX media is added to appropriate wells of a 96-well chemotaxis chamber (Neuro Probe Cat. #:116-5, 5 µm pore size, 5.7 mm diameter size, 300 µL, 96 well plate). CTX media without chemoattractant is added to control wells. 152µL of 2× compound solution in CTX media is added to appropriate wells. The chamber is assembled according to manufacturer's instructions using the 5 micron pore size PVP-free polycarbonate filter. Care should be taken to avoid bubbles as they will cause variation.

80 µL of the cells plus compound incubation mixture is added to upper wells of the chamber. Care is taken to avoid forming bubbles at the level of the filter. The chamber is then incubated at 37° C. for 3 hours.

The chamber is then disassembled and the filter is removed. 150 µL of media is gently removed from each well of the chemotaxis chamber. The remaining 150 µL is then mixed and 100 µL of the resulting cell suspension is transferred into a 96 well Costar 3917 assay plate (Coming incorporated, cat #3917).

The cells are measured using a CyQUANT® NF Cell Proliferation Assay (Invitrogen, cat #C35006). 11 mL of 1× HBSS buffer is prepared by diluting 2.2 mL of 5× HBSS buffer (Component C) with 8.8 mL of deionized water. 1× dye binding solution is prepared by adding 22 microL of CyQUANT® NF dye reagent (Component A) and 22 microL of Component C to 11 mL of 1× HBSS buffer. 100 microL of 1× dye binding solution is dispensed into wells of the 96 well Costar plate containing the cell suspensions. The plate is covered and incubated at 37° C. for 60 minutes. Fluorescence measurement is quantitated using a multilabel plate reader (Wallac Victor2).

Methods of Therapeutic Use

In accordance with the invention, there are provided novel methods of using the compounds of the present invention. The compounds disclosed herein effectively block the interaction of CCR10 with its ligands CCL27 and CCL28. The inhibition of this interaction is an attractive means for preventing and treating a variety of diseases or conditions associated with entry and activation of T-cells into the skin or other tissues where CCR10 is found to be expressed and associated with inflammatory conditions, such as lung tissue. Thus, the compounds of the present invention are useful for the treatment of diseases and conditions including psoriasis, contact sensitivity, dermatitis, systemic sclerosis, cutaneous systemic lupus erythematosus, and allergic asthma. The compounds of the invention will also be useful for treatment of melanomas that express CCR10.

These disorders have been well characterized in man, but also exist with a similar etiology in other mammals, and can be treated by pharmaceutical compositions of the present invention.

For therapeutic use, the compounds may be administered in a therapeutically effective amount in any conventional dosage form in any conventional manner. Routes of administration include, but are not limited to, intravenously, intramuscularly, subcutaneously, intrasynovially, by infusion, sublingually, transdermally, orally, topically or by inhalation, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). A therapeutically effective amount can be determined by a skilled artisan based upon such factors as weight, metabolism, and severity of the affliction etc. Preferably the active compound is dosed at about 1 mg to about 500 mg per kilogram of body weight on a daily basis. More preferably the active compound is dosed at about 1 mg to about 100 mg per kilogram of body weight on a daily basis.

The compounds may be administered alone or in combination with adjuvants that enhance the stability of the inhibitors, facilitate administration of pharmaceutic compositions containing them in certain embodiments, provide increased dissolution or dispersion, increase inhibitory activity, provide adjunct therapy, and the like. Advantageously, such combinations may utilize lower dosages of the active ingredient, thus reducing possible toxicity and adverse side effects. Pharmaceutically acceptable carriers and adjuvants for use with compounds according to the present invention include, for example, ion exchangers, alumina, aluminum stearate, lecithin, serum proteins, buffer substances, water, salts or electrolytes and cellulose-based substances. This is not a complete list possible pharmaceutically acceptable carriers and adjuvants, and one of ordinary skilled in the art would know other possibilities, which are replete in the art.

We claim:

1. A compound of formula I:

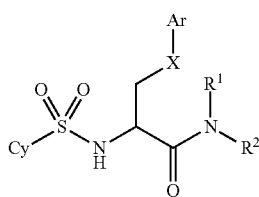

(I)

wherein:
Cy is heteroaryl selected from indolyl, 1,3-dihydro-indol-2-onyl, pyridyl, pyrazolyl, or benzothienyl;
Ar is a phenyl, pyridyl, or isoquinolinyl group optionally substituted by one to two groups independently selected from —Cl, —Br, —F, —CN, —NO$_2$, —CO$_2$Me, -Me, SO$_2$Me, ethynyl, and 1-propynyl;

$R^1$ and $R^2$, together with the N they are bonded to, form a heterocycle selected from piperidine, piperazine, azepane, [1,4]-diazepane, [1,4]-oxazepane, and 5,6,7,8-tetrahydro-[1,2,4]triazolo[4,3-a]pyrazine, wherein said heterocycle is optionally substituted by one to two groups selected from $C_{1-6}$alkyl, $C_{1-4}$alkylOH, C(O)$C_{1-4}$alkyl, CO$_2$Me, and oxo; and
X is CH$_2$, O, NH, or S;
or a pharmaceutically acceptable salt thereof.

2. A compound selected from the group consisting of:
N-{3-(2-chlorophenyl)-1-[(4-methylpiperidin-1-yl)carbonyl]propyl}-2-methylbenzenesulfonamide, N-{3-(2-chlorophenyl)-1-[(4-methylpiperidin-1-yl)carbonyl]propyl}-3-methylbenzenesulfonamide, N-{3-(2-chlorophenyl)-1-[(4-methylpiperidin-1-yl)carbonyl]propyl}-2,4-dimethylbenzenesulfonamide, N-{3-(2-chlorophenyl)-1-[(4-methylpiperidin-1-yl)carbonyl]propyl}-2,5-dimethylbenzenesulfonamide, N-{3-(2-chlorophenyl)-1-[(4-methylpiperidin-1-yl)carbonyl]propyl}-3,5-dimethylbenzenesulfonamide, N-{3-(2-chlorophenyl)-1-[(4-methylpiperidin-1-yl)carbonyl]propyl}-2-methoxybenzenesulfonamide, N-{3-(2-chlorophenyl)-1-[(4-methylpiperidin-1-yl)carbonyl]propyl}-4-fluoro-2-methylbenzenesulfonamide, 2-chloro-N-{3-(2-chlorophenyl)-1-[(4-methylpiperidin-1-yl)carbonyl]propyl}benzenesulfonamide, 2-chloro-N-{3-(2-chlorophenyl)-1-[(4-methylpiperidin-1-yl)carbonyl]propyl}pyridine-3-sulfonamide, N-{3-(2-chlorophenyl)-1-[(4-methylpiperidin-1-yl)carbonyl]propyl}-1H-indole-3-sulfonamide, N-{3-(2-chlorophenyl)-1-[(4-methylpiperidin-1-yl)carbonyl]propyl}-1H-indole-4-sulfonamide, N-{3-(2-chlorophenyl)-1-[(4-methylpiperidin-1-yl)carbonyl]propyl}-1H-indole-6-sulfonamide, N-{3-(2-chlorophenyl)-1-[(4-methylpiperidin-1-yl)carbonyl]propyl}-2-methoxy-5-methylbenzenesulfonamide, 5-chloro-N-{3-(2-chlorophenyl)-1-[(4-methylpiperidin-1-yl)carbonyl]propyl}-1,3-dimethyl-1H-pyrazole-4-sulfonamide, N-{3-(2-chlorophenyl)-1-[(4-methylpiperidin-1-yl)carbonyl]propyl}-1-methyl-1H-indole-4-sulfonamide, N-{3-(2-chlorophenyl)-1-[(4-methylpiperidin-1-yl)carbonyl]propyl}-2-oxo-2,3-dihydro-1H-indole-5-sulfonamide, and a pharmaceutically acceptable salt thereof.

3. A pharmaceutical composition comprising a compound of claim 1, or a pharmaceutically acceptable salt thereof.

4. A pharmaceutical composition comprising a compound of claim 2 or a pharmaceutically acceptable salt thereof.

* * * * *